US011679160B2

(12) United States Patent
Pombo-Villar et al.

(10) Patent No.: US 11,679,160 B2
(45) Date of Patent: Jun. 20, 2023

(54) CASTRATION RESISTANT PROSTATE CANCER

(71) Applicant: TARGIMMUNE THERAPEUTICS AG, Basel (CH)

(72) Inventors: Esteban Pombo-Villar, Binningen (CH); Alexander Levitzki, Jerusalem (IL); Yael Langut, Haifa (IL); Maya Zigler, Basel (CH); Alexei Shir, Jerusalem (IL); Eric Kitas, Aesch (CH)

(73) Assignee: TARGIMMUNE THERAPEUTICS AG, Basel (CH)

( * ) Notice: Subject to any disclaimer, the term of this patent is extended or adjusted under 35 U.S.C. 154(b) by 347 days.

(21) Appl. No.: 16/650,980

(22) PCT Filed: Sep. 27, 2018

(86) PCT No.: PCT/EP2018/076293
§ 371 (c)(1),
(2) Date: Mar. 26, 2020

(87) PCT Pub. No.: WO2019/063705
PCT Pub. Date: Apr. 4, 2019

(65) Prior Publication Data
US 2020/0230248 A1 Jul. 23, 2020

(30) Foreign Application Priority Data

Sep. 27, 2017 (EP) .................................... 17193577
Nov. 14, 2017 (EP) .................................... 17201728

(51) Int. Cl.
| | | |
|---|---|---|
| *A61K 47/54* | (2017.01) | |
| *A61K 47/65* | (2017.01) | |
| *A61K 47/60* | (2017.01) | |
| *A61K 47/59* | (2017.01) | |
| *C07K 7/02* | (2006.01) | |
| *C07K 7/06* | (2006.01) | |

(52) U.S. Cl.
CPC ............ *A61K 47/549* (2017.08); *A61K 47/59* (2017.08); *A61K 47/60* (2017.08); *A61K 47/65* (2017.08); *C07K 7/02* (2013.01); *C07K 7/06* (2013.01)

(58) Field of Classification Search
CPC ........... C25B 9/65; C25B 9/77; A61K 47/542; A61K 47/549; A61K 47/59; A61K 47/60; A61K 47/65; A61P 35/00; C07K 7/02; C07K 7/06; C12N 15/88
See application file for complete search history.

(56) References Cited

U.S. PATENT DOCUMENTS

| | | | | |
|---|---|---|---|---|
| 10,029,023 | B2 * | 7/2018 | Pomper | A61K 31/513 |
| 10,278,991 | B2 * | 5/2019 | Levitzki | A61K 47/60 |
| 10,543,232 | B2 * | 1/2020 | Levitzki | C12N 15/117 |
| 11,298,376 | B2 * | 4/2022 | Levitzki | C12N 15/117 |

FOREIGN PATENT DOCUMENTS

| | | |
|---|---|---|
| WO | 2004/045491 A2 | 6/2004 |
| WO | 2015/173824 A1 | 11/2015 |

OTHER PUBLICATIONS

Kulkarni et al. PSMA-Based Radioligand Therapy for Metastatic Castration-Resistant Prostate Cancer: The Bad Berka Experience Since 2013. J Nucl Med, vol. 57, pp. 97S-104S. (Year: 2016).*
Saad et al. Guidelines for the management of castrate-resistant prostate cancer. Can Urol Assoc J 2010, vol. 4, No. 6, pp. 380-384. (Year: 2010).*
Joubran et al., "Optimization of Liganded Polyethylenimine Polyethylene Glycol Vector for Nucleic Acid Delivery," Bioconjugate Chem. 25:1644-1654 (2015).
Wu et al., "Delivery of EZH2-shRNA with mPEG-PEI nanoparticles for the treatment of prostate cancer in vitro," Int. J. of Mol. Med. 33:1563-1569 (2014).
The International Search Report in International Application No. PCT/EP2018/076293, dated Dec. 7, 2018.

* cited by examiner

*Primary Examiner* — Marcela M Cordero Garcia
(74) *Attorney, Agent, or Firm* — Medler Ferro Woodhouse & Mills PLLC

(57) ABSTRACT

The present invention relates to a polyplex for use in the treatment of castration resistant prostate cancer (CRPC) comprising a double stranded RNA (dsRNA) and a polymeric conjugate, wherein said polymeric conjugate consists of a linear polyethyleneimine (LPEI), one or more polyethylene glycol (PEG) moieties, one or more linkers and one or more targeting moieties, wherein said LPEI is covalently bound to one or more PEG moieties and each of said one or more PEG moieties is conjugated via one of the one or more linkers to one of the one or more targeting moieties, wherein each of said one or more targeting moieties is capable of binding to a cancer antigen, and wherein said cancer antigen is prostate surface membrane antigen (PSMA). Further, the invention relates to a pharmaceutical composition for use in the treatment of CRPC.

20 Claims, 10 Drawing Sheets
Specification includes a Sequence Listing.

RANTES

IP-10

CASTRATION RESISTANT PROSTATE CANCER

REFERENCE TO AN ELECTRONIC SEQUENCE LISTING

The contents of the electronic sequence listing (0192_0104US1_SL.txt; Size: 11,064 bytes; and Date of Creation: Jan. 23, 2023) is herein incorporated by reference in its entirety.

The present invention relates to the field of prostate cancer treatment. In particular, the present invention relates to a polyplex and a pharmaceutical composition comprising said polyplex, both for use in the treatment of castration resistant prostate cancer (CRPC). Said polyplex comprises a double stranded RNA (dsRNA) and a polymeric conjugate, wherein said polymeric conjugate consists of a linear polyethyleneimine (LPEI), one or more polyethylene glycol (PEG) moieties, one or more linkers and one or more targeting moieties, wherein said LPEI is covalently bound to said one or more PEG moieties and each said one or more PEG moieties is conjugated via one of said one or more linkers to one of said one or more targeting moieties, wherein each of said one or more targeting moieties is capable of binding to a cancer antigen, and wherein said cancer antigen is prostate surface membrane antigen (PSMA).

RELATED ART

Prostate cancer is considered to be the second most commonly diagnosed type of cancer in men worldwide. If a biochemical relapse is diagnosed after therapy by radiation or surgery, either observation or androgen deprivation therapy (ADT) is the standard treatment. While therapy by androgen deprivation is very effective at achieving short-term remission, most patients get resistant to this treatment and the disease progress with developing castration resistant prostate cancer (CRPC) (Luo et al., Treatment of Nonmetastatic Castration-Resistant Prostate Cancer, Oncology 2016, 30(4):336-44; Kumar et al., Design of a Small-Molecule Drug Conjugate for Prostate Cancer Targeted Theranostics, Bioconjugate Chem. 2016, 27:1681-1689).

For the palliative management of men with metastatic castration resistant prostate cancer, docetaxel and prednisone were approved by the United States Food and Drug Administration (FDA) in 2004, based on prolonged survival, tumor response, reduction in pain and improved quality-of-life, in addition to tolerability (Tannock et al., Docetaxel plus prednisone or mitoxantrone plus prednisone for advanced prostate cancer, N Engl J Med. 2004, 351(15):1502-12). Despite docetaxel's approval, median progression-free survival remains about 6 months and overall survival remains less than 2 years with that chemotherapy (Bellmunt et al., Castration-resistant prostate cancer: new science and therapeutic prospects, Ther Adv Med Oncol 2010, 2(3):189-207).

Further advances have been seen as the FDA approved cabazitaxel in 2010 as a second-line treatment of metastatic castration resistant prostate cancer patients. However, due to the multidrug resistance and safety concerns of cytotoxic drugs, chemotherapy of prostate cancer is still deemed less favorable (Kumar et al., 2016, op. cit.).

Efforts in the area of salvage chemotherapy have been focused on several classes of cytotoxic agents, including platinum agents and novel microtubule-targeting agents. However, the lack of statistically significant benefit with initially promising agents like the platinum agent satraplatin has generated a decrease of enthusiasm for chemotherapy alone in this disease. This forms the rationale for moving towards targeted agents alone or in combination with chemotherapy (Bellmunt et al., 2010, op. cit.).

Several investigational agents target pathways in pathogenesis, maintenance, and progression of prostate cancer. These include therapies that target the human epidermal growth factor receptor 2 (HER2), the phosphatidylinositol-3 kinase (PI3K)/Akt, the mammalian target of rapamycin (mTOR), and the insulin-like growth factor (IGF)-1 pathways. Even though preclinical evidence supports the importance of these molecular pathways, clinical testing of most of these agents remains immature (Bellmunt et al., 2010, op. cit.).

Several small-molecule drug conjugates have been reported some of which target prostate specific membrane antigen (PSMA). PSMA is a cell surface glycoprotein expressed by a very high proportion by prostate cancer cells as compared to normal prostate (Silver et al., 1997, Prostate-specific membrane antigen expression in normal and malignant human tissues, Clin. Cancer Res. 3, 81-85)

A theranostic design of small-molecule drug conjugates (T-SMDCs) for targeted imaging and chemotherapy of prostate cancer was developed. The structure of T-SMDCs built upon a polyethylene glycol (PEG) scaffold consists of (i) a chelating moiety for positron emission tomography (PET) imaging when labeled with 68Ga, a positron-emitting radioisotope; (ii) a prostate specific membrane antigen (PSMA) specific ligand for prostate cancer targeting; and (iii) a cytotoxic drug (DM1) for chemotherapy. For proof-of-concept, such a T-SMDC, NO3A-DM1-Lys-Urea-Glu, was synthesized and evaluated (Kumar et al., 2016, op. cit.).

Targeted delivery of dsRNA using polyplexes of PEI, PEG and a targeting moiety (PEI-PEG-targeting moiety/dsRNA polyplex) was developed. The targeting moieties of these conjugates bind to a cancer antigen which may be an epidermal growth factor receptor (EGFR), human epidermal growth factor receptor 2 (HER2), prostate surface membrane antigen (PSMA), an insulin-like growth factor 1 receptor (IGF1R), a vascular endothelial growth factor receptor (VEGFR), a platelet-derived growth factor receptor (PDGFR) or a fibroblast growth factor receptor (FGFR)(WO 2015/173824).

Thus, there is a high need for effective therapies for castration resistant prostate cancer.

SUMMARY OF THE INVENTION

The invention presents herein a new approach to meet this requirement and provides for a treatment of castration resistant prostate cancer (CRPC).

In a first aspect, the invention relates to a polyplex for use in the treatment of castration resistant prostate cancer (CRPC) comprising a double stranded RNA (dsRNA) and a polymeric conjugate, wherein said polymeric conjugate consists of a linear polyethyleneimine (LPEI), one or more polyethylene glycol (PEG) moieties, one or more linkers and one or more targeting moieties, wherein said LPEI is covalently bound to said one or more PEG moieties and each of said one or more PEG moieties is conjugated via one of said one or more linkers to one of said one or more targeting moieties, wherein each of said one or more targeting moieties is capable of binding to a cancer antigen, and wherein said cancer antigen is prostate surface membrane antigen (PSMA).

In a second aspect, the invention relates to a pharmaceutical composition for use in the treatment of castration resistant prostate cancer (CRPC), wherein said pharmaceutical composition comprises a pharmaceutically acceptable carrier and the polyplex of the invention comprising a double stranded RNA (dsRNA) and a polymeric conjugate, wherein said polymeric conjugate consists of a linear polyethyleneimine (LPEI), one or more polyethylene glycol (PEG) moieties, one or more linkers and one or more targeting moieties, wherein said LPEI is covalently bound to said one or more PEG moieties and each of said one or more PEG moieties is conjugated via one of said one or more linkers to one of said one or more targeting moieties, wherein each of said one or more targeting moieties is capable of binding to a cancer antigen, and wherein said cancer antigen is prostate surface membrane antigen (PSMA).

The inventors surprisingly found that the polyplex of the invention is an effective treatment for CRPC.

The targeted polyplex allows selective delivery of dsRNA, such as polyIC to PSMA overexpressing cells included the tissue of CRPC. DsRNA, especially polyinosine-polycytosine (polyinosinic-polycytidylic acid double stranded RNA; polyIC) activates multiple death pathways in cell systems. Following uptake into cancer cells, polyIC induces apoptosis and leads to rapid and efficient clearance of targeted cancer cells. Additionally, polyIC induces "bystander effects" that activates the immune system to against the tumor, killing not only targeted tumor cells but also non-targeted neighboring tumor cells.

The combination of both effects provides a potent treatment of patients with CRPC that leads to the regression of heterogeneous tumors and prevents the development of drug resistance. However, naked dsRNA and in particular polyIC is highly toxic and per se not suitable for systemic use.

Therefore, the inventors developed a targeted polyplex for selective delivery of dsRNA, such as polyIC to PSMA overexpressing cells. Using PSMA as CRPC target, the polyplex of the invention including dsRNA is directly and selectively delivered to CRPC cells and tissue which highly overexpress PSMA. Compared to early stages of prostate cancer, PSMA expression is further increased in higher-grade cancers, metastatic disease and hormone-refractory prostate cancer. Moreover, PSMA expression is modulated inversely by androgen levels (Liu et al., Constitutive and Antibody-induced Internalization of Prostate-specific Membrane Antigen, Cancer Research 1998, 58, 4055-4060). Thus, using PSMA as target allows selective delivery of the polyplex of the invention to CRPC cells.

Since polyIC is very toxic when administered systemically, its use is limited to a narrow therapeutic window. By targeting dsRNA selectively to CRPC cells, advantage of its potency can be taken while avoiding the toxicity typically incurred in systemic use. Moreover, targeted delivery provides the advantage that very low doses can be used which also improves tolerability of polyIC.

The polyplex of the invention allows selective delivery and internalization of polyIC into CRPC cells, inducing apoptosis, cytokine secretion and recruitment of immune cells (human peripheral blood mononuclear cells, PBMCs). In an in vivo tumor model for androgen-resistant prostate cancer, NOD-SCID mice with partially reconstituted immune systems harboring tumors over-expressing PSMA were treated with the PSMA targeted polyplex according to the invention including polyIC. Tumor growth was impeded or even regressed following administration of the polyplex of the invention. The inventors thus showed that the polyplex of the invention has remarkable efficacy in the treatment of CRPC.

The demonstrated in vivo and in vitro effects lead to the conclusion that the polyplex of the invention is not only delivered to CRPC tissue but also that the design of the polyplex of the invention is such that it penetrates CRPC tissue, is internalized into CRPC cells and has an anti-tumor effect on CRPC cells.

Figure 1A:
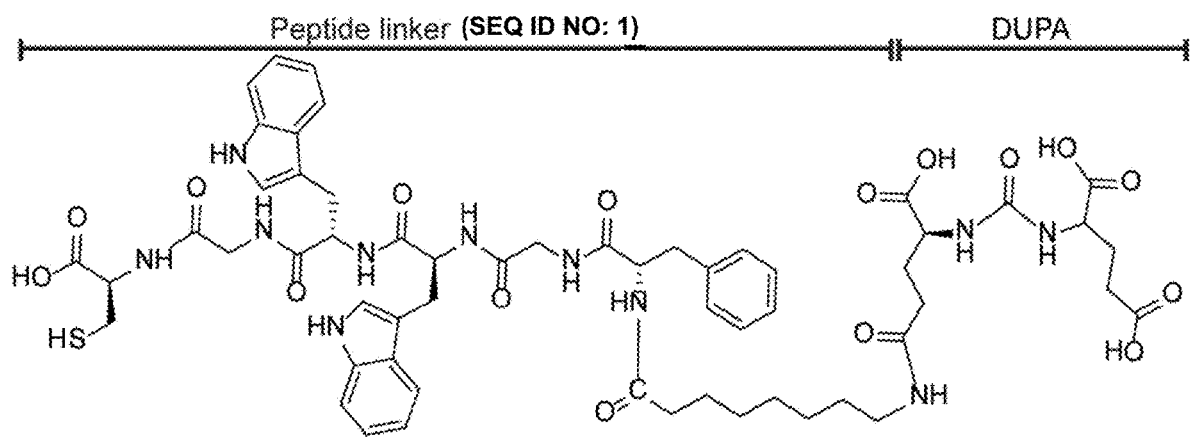
FIG. 1: A. Structure of the DUPA-peptide linker; B. Selective uptake of the conjugate DUPA-peptide linker-Dylight680 into PSMA over-expressing cells. Microscopic images of cultured PC3-PSMA and LNCaP cells or control cells MCF7 after treatment with DUPA-peptide linker-Dylight680 (visualization via laser scanning confocal fluorescence microscopy). Signal of the fluorescent Dylight680 are depicted in white.

A. LNCaP, VCaP, PC3-PSMA, PC3 and MCF7 cells were treated with 0.1 µg/ml, 0.25 µg/ml, 0.5 µg/ml or 1 µg/ml of polyIC included in PPD/polyIC. Controls: Treatment with PPD/polyI or polyIC alone or untreated (UT). Measurement of cell viability 96 h after initiation of the treatment via the CellTiter-Glo Luminescent Cell Viability Assay (Promega). (*$P \leq 0.001$ LNCaP or VCaP or PC3-PSMA vs MCF7 or PC3, **$P \leq 0.001$ µg/ml PPD/polyIC vs 1 µg/ml PPD/polyI or 1 µg/ml polyIC alone).

B. LNCaP cells were treated with PPD/polyIC. The indicated concentrations refer to the polyIC included in PPD/polyIC. Measurement of cell viability via the CellTiter-Glo Luminescent Cell Viability Assay (Promega).

C. Activation of apoptotic signaling pathways by treatment with PPD/polyIC. Whole cell lysates from LNCaP cells were treated with PPD/polyIC (2 µg/ml polyIC) and expression levels of cleaved/full length caspase 3, cleaved/full length PARP 3 and GAPDH were detected by western blots.

FIG. 3: Secretion of pro-inflammatory and cytotoxic cytokines by treatment with PPD/polyIC. Treatment of LNCaP and PC3-PSMA cells with PPD/polyIC for 48 h and 72 h (A), (B) or 4 h and 8 h (C). Concentrations as indicated refer to polyIC included in PPD/polyIC. Measurement of protein levels of RANTES (Regulated on Activation, Normal T cell Expressed and Secreted) (A) and IL-10 by ELISA assays (B) and of IFN-β mRNA by qRT-PCR (C).

FIG. 4: Chemotaxis and activation of human PBMCs by treatment with PPD/polyIC. The indicated concentrations refer to the polyIC included in PPD/polyIC. A. Chemotactic index: Ratio of (i) the number of cells that migrated in the presence of conditioned medium from treated cells to (ii) the number that migrated in the presence of conditioned medium from untreated cells. B. Measurement of IL 2, TNF-α and INF-γ mRNA expression in PBMCs after incubation with conditioned medium from treated LNCaP cells. Isolation of total cellular RNA from PBMCs after 24 h incubation with conditioned medium from LNCaP cells treated with PPD/polyIC for 48 h. RNA quantification via qRT-PCR. Normalization to mRNA levels of HUPO.

FIG. 5: Bystander effects caused by treatment with PPD/polyIC. Cells were treated with PPD/polyIC, wherein the indicated concentrations refer to polyIC included in PPD/polyIC at the indicated concentrations of polyIC. Measurement of cell survival via Luciferase assay (Promega).

A. Clearance of LNCaP cells by low doses of PPD/polyIC. 24 h after starting the treatment, PBMCs or only cell medium was added to the culture for additional 48 h or 72 h.

B and C. Death of untargeted cells induced by treatment with PPD/polyIC via direct and PBMC-mediated bystander effects. Treatment of cultured LNCaP cells or PC3-PSMA cells with PPD/polyIC. 24 h after starting the treatment, PC3-Luc cells or MCF7-Luc cells were added to the culture, and PBMCs or only cell medium was added 6 h later. The co-culture was incubated for further 72 h.

Figure 6:
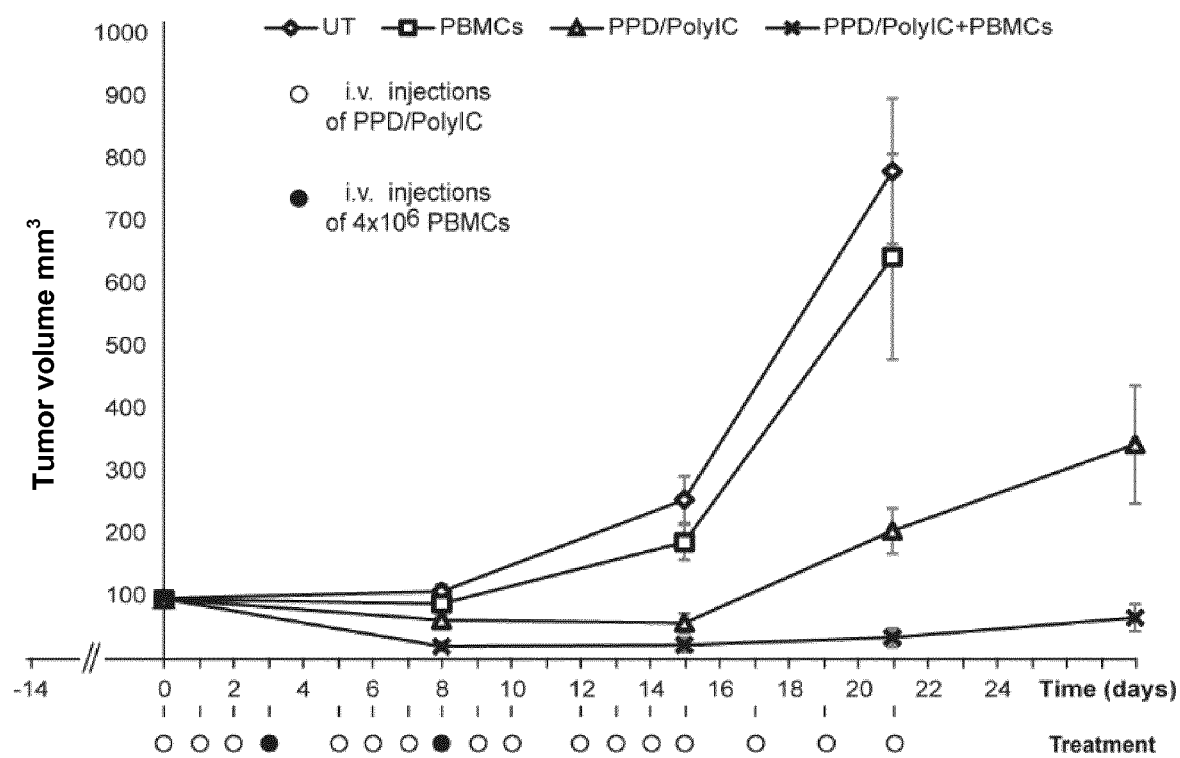

FIG. 6: Regression of PSMA-overexpressing tumors in an androgen-resistant prostate cancer in vivo model by PPD/polyIC treatment. Tumors bearing mice were injected with PPD/polyIC alone, PBMCs alone or PPD/polyIC and PBMCs (*P≤0.001, PPD/polyIC+PBMC treatment vs untreated mice. P≤0.01, PPD/polyIC+PBMC treatment vs PPD/polyIC alone).

DETAILED DESCRIPTION OF THE INVENTION

In a first aspect, the invention relates to a polyplex for use in the treatment of castration resistant prostate cancer (CRPC) comprising a double stranded RNA (dsRNA) and a polymeric conjugate, wherein said polymeric conjugate consists of a linear polyethyleneimine (LPEI), one or more polyethylene glycol (PEG) moieties, one or more linkers and one or more targeting moieties, wherein said LPEI is covalently bound to said one or more PEG moieties and each of said one or more PEG moieties is conjugated via one of said one or more linkers to one of said one or more targeting moieties, wherein each of said one or more targeting moieties is capable of binding to a cancer antigen, and wherein said cancer antigen is prostate surface membrane antigen (PSMA).

The polyplex of the invention is for use in a method of treating castration resistant prostate cancer (CRPC), wherein said polyplex comprises a double stranded RNA (dsRNA) and a polymeric conjugate, wherein said polymeric conjugate consists of a linear polyethyleneimine (LPEI), one or more polyethylene glycol (PEG) moieties, one or more linkers and one or more targeting moieties, wherein said LPEI is covalently bound to said one or more PEG moieties and each of said one or more PEG moieties is conjugated via one of said one or more linkers to one of said one or more targeting moieties, wherein each of said one or more targeting moieties is capable of binding to a cancer antigen, and wherein said cancer antigen is prostate surface membrane antigen (PSMA).

If biochemical recurrence, i.e. rising level of prostate specific antigen (PSA), occurs after an attempt at cure with radiation or surgery, either observation or androgen deprivation therapy (ADT) is the standard of care. Prostate cancer was first shown to be androgen-dependent in seminal work in the 1940s, and since then, ADT, which results in apoptosis and growth inhibition of prostate cancer cells, has become essential to treating advanced prostate cancer. Castration, either surgical or medical, results in a serum testosterone level of <50 ng/dL. Prostate cancer eventually becomes resistant to ADT in nearly all patients, at which point serum PSA levels begin to rise and/or metastases emerge, despite a serum testosterone level of <50 ng/dL (Luo et al., 2016, op. cit.).

As used herein, the term "castration resistant prostate cancer" (CRPC) is typically and preferably defined by a serum testosterone level of <50 ng/dL and the presence of a rising prostate specific antigen (PSA) level and/or detectable metastasis or metastases.

Detectable metastasis or metastases are preferably detected clinically or by imaging techniques. Preferred imaging techniques are radiography, computerized tomography (CT) or Magnetic Resonance Imaging (MRI).

PSA level is preferably tested based on patient's blood or serum samples, wherein preferably total PSA which is the sum of the free and the bound PSA is detected. Measurement of PSA level is typically and preferably carried out using standard PSA tests which are well known to those skilled in the art. Preferably, such a standard PSA test is an immunoassay, more preferably a chemiluminescence immunoassay, again more preferably an electro-chemiluminescence immunoassay, performed for example by employing Roche MODULAR E170. The definition of a rising PSA used herein is from the Prostate Cancer Working Group 2 (PCWG2) and refers to an increase of 25% from the nadir, with a minimum rise of 2 ng/mL, wherein the value is measured twice; the first value needs to be confirmed by a second value, which is typically and preferably obtained 1 to 3 weeks after the first value.

Serum testosterone level is preferably tested based on patient's blood or serum samples, wherein preferably total testosterone level is detected. Measurement of testosterone level is typically and preferably carried out using standard tests which are well known to those skilled in the art. Preferably, such a standard test is ELISA, chemiluminescence immunoassay, liquid chromatography-mass spectrometry (LC-MS) or LC-MS/MS.

In a preferred embodiment, said CRPC is defined by a serum testosterone level of <50 ng/dL and detectable metastasis or metastases. In a more preferred embodiment, CRPC is defined by a serum testosterone level of <50 ng/dL and the presence of a rising prostate specific antigen (PSA) level.

If no metastatic lesions can be detected by imaging studies in patients with CRPC, this disease state is preferably and typically defined herein as "non-metastatic castration-resistant prostate cancer" (nmCRPC). If metastases can be detected by imaging studies in patients with CRPC, this disease state is preferably and typically defined herein as "metastatic castration-resistant prostate cancer" (nmCRPC). Imaging studies are typically and preferably nuclear medicine technetium-99m scintigraphy (bone scan) as well as computed tomography (CT) of the chest, abdomen, and pelvis (Luo et al., 2016, op. cit.). nmCRPC includes hormone-sensitive nmCRPC responding to secondary hormonal manipulations and hormone refractory nmCRPC being resistant to hormonal treatments.

In a preferred embodiment, said CRPC is non-metastatic CRPC or metastatic CRPC. Preferably said CRPC is metastatic CRPC. In another embodiment, said CRPC is non-metastatic CRPC.

In a preferred embodiment, said CRPC is androgen receptor (AR) independent (also called AR resistant) CRPC or AR dependent CRPC. More preferably, said CRPC is AR independent CRPC, such as such as neuroendocrine prostate cancer.

AR dependent CRPC is preferably defined as androgen-sensitive CRPC. AR dependent CRPC preferably continues to be dependent on the AR signaling axis despite systemic depletion of androgens.

AR independent CRPC is preferably defined as resistant (i.e. insensitive) to androgen treatment.

The polyplex for use according to the invention includes linear polyethyleneimine (LPEI) which is a linear polycation with the capacity to condense and associate non-covalently with nucleic acid molecules due to the polyanionic nature of the latter. In a preferred embodiment, LPEI includes a hydroxyl group located at one or either end of LPEI. Preferably, said hydroxyl group is instead of the terminal —NH$_2$ group of LPEI.

In a preferred embodiment of the invention, LPEI has a molecular weight from about 10-30 kDa. More preferably, LPEI has a molecular weight of about 22 kDa.

The polyplex for use according to the invention includes one or more polyethylene glycol (PEG) moieties. PEG moieties according to the invention are also known as polyethylene oxide (PEO) or polyoxyethylene (POE) moieties, depending on its molecular weight. As used herein the term "polyethylene glycol moiety" (PEG moiety) typically and preferably refers to a PEG moiety comprising two functionalities located on either end of polyethylene glycol (PEG). Said functionalities are capable of reacting with either said LPEI or said targeting moiety.

In one embodiment of the invention, each of said at least one said PEG moiety has a molecular weight from about 2-8 kDa, preferably 2 kDa.

In a preferred embodiment, LPEI has a molecular weight of about 10-30 kDa, and said at least one PEG moiety has a molecular weight of about 2-8 kDa. In a more preferred embodiment, LPEI has a molecular weight of 22 kDa (LPEI$_{22k}$), and said at least one PEG moiety has a molecular weight of 2 kDa (PEG$_{2K}$).

In a preferred embodiment, LPEI$_{22k}$ is covalently linked to one PEG$_{2K}$ moiety or three PEG$_{2K}$ moieties. In another preferred embodiment, LPEI$_{22k}$ is covalently linked to one PEG$_{2K}$. In a further preferred embodiment, LPEI$_{22k}$ is covalently linked to three PEG$_{2K}$ moieties.

The term "dsRNA" typically and preferably refers to double stranded ribonucleotide polymers of any length in which one or more ribonucleotides can be chemical analogues or modified derivatives of a corresponding naturally-occurring ribonucleotide. The term "dsRNA" typically and preferably also includes mismatched dsRNA.

In the most preferred embodiment, said dsRNA is polyinosinic-polycytidylic acid double stranded RNA (polyIC). PolyIC is a double-stranded RNA with one strand being a polymer of inosinic acid, the other a polymer of cytidylic acid.

The polyIC of the polyplex for use according to the invention may be composed of dsRNA, wherein each strand consists of at least 22, preferably at least 45 ribonucleotides. In a certain embodiment, each strand consists of 20 to 8000 ribonucleotides. In a more preferred embodiment each strand consists of 200 to 1000 ribonucleotides. In a preferred embodiment, said polyIC has a molecular weight from 0.2 kb to 1 kb.

As used herein, the term "LPEI-PEG 1:1" or "LPEI [ . . . ] covalently linked to one PEG moiety", which both are used interchangeably herein, refers to the molar ratio of LPEI to PEG, wherein LPEI-PEG 1:1 typically and preferably means that approximately one mole PEG per one mole LPEI is included in the polymeric conjugate. As used herein, the term "LPEI-PEG 1:3" or "LPEI [ . . . ] covalently linked to three PEG moieties" typically and preferably means that approximately three moles PEG per one mole LPEI are included in the polymeric conjugate. The values are preferably determined by $^1$H-NMR analysis. Preferably using the relative integral values of the hydrogen atoms on PEG (—CH$_2$—CH$_2$—O—) and the integral values of the hydrogen atoms on LPEI (—CH$_2$—CH$_2$—NH—) are used for determining the values via $^1$H-NMR. The term "approximately" herein refers to a deviation of about 0%-10%, more preferably 0%-5%, again more preferably 0%-2%.

In a preferred embodiment, said dsRNA of the polyplex is polyIC and said LPEI of the polymeric conjugate of the polyplex for use according to the invention is covalently linked to one PEG moiety (LPEI-PEG 1:1) or to three PEG moieties (LPEI-PEG 1:3).

In a preferred embodiment, said dsRNA is polyIC and said LPEI is covalently linked to one PEG moiety (LPEI-PEG 1:1). In this embodiment, said one or more PEG moieties of the polyplex of the invention is one PEG moiety. Thus, said LPEI is covalently bound to one PEG moiety and said one PEG moiety is conjugated via one linker to one targeting moiety.

In another preferred embodiment, said dsRNA is polyIC and said LPEI is covalently linked to three PEG moieties (LPEI-PEG 1:3). In this embodiment, said one or more PEG moieties of the polyplex of the invention are three PEG moieties. Thus, said LPEI is covalently bound to three PEG moieties and each of said three PEG moiety is conjugated via one linker to one targeting moiety.

In a preferred embodiment, said dsRNA of the polyplex is polyIC and said LPEI of the polymeric conjugate of the polyplex for use according to the invention is LPEI$_{22k}$. In a preferred embodiment, said dsRNA of the polyplex is polyIC and said LPEI of the polymeric conjugate of the polyplex for use according to the invention is LPEI$_{22k}$ and is covalently linked to one PEG moiety (LPEI-PEG 1:1) or three PEG moieties (LPEI-PEG 1:3). In a preferred embodiment, said dsRNA is polyIC and said LPEI is LPEI$_{22k}$ and is covalently linked to three PEG moieties (LPEI-PEG 1:3). In a preferred embodiment, said dsRNA is polyIC and said LPEI is LPEI$_{22k}$ and is covalently linked to one PEG moiety (LPEI-PEG 1:1).

In a preferred embodiment, said dsRNA is polyIC and said one or more PEG moieties of the polymeric conjugate are PEG$_{2K}$. In a preferred embodiment, said dsRNA is polyIC and said LPEI is covalently linked to one PEG$_{2K}$ moiety (LPEI-PEG 1:1) or three PEG$_{2K}$ moieties (LPEI-PEG 1:3). In a preferred embodiment, said dsRNA is polyIC and said LPEI is covalently linked to one PEG$_{2K}$ moieties (LPEI-PEG 1:1). In a preferred embodiment, said dsRNA is polyIC and said LPEI is covalently linked to three PEG$_{2K}$ moieties (LPEI-PEG 1:3). In a preferred embodiment, said dsRNA of the polyplex is polyIC, said LPEI of the polymeric conjugate is LPEI$_{22k}$ and said one or more PEG moieties are PEG$_{2K}$ moiety. In a preferred embodiment, said dsRNA of the polyplex is polyIC and said LPEI is LPEI$_{22k}$ and is covalently linked to one PEG$_{2K}$ moiety (LPEI-PEG 1:1) or three PEG$_{2K}$ moieties (LPEI-PEG 1:3). In a preferred embodiment, said dsRNA of the polyplex is polyIC and said LPEI is LPEI$_{22k}$ and is covalently linked to one PEG$_{2K}$ moiety (LPEI-PEG 1:1). In a preferred embodiment, said dsRNA of the polyplex is polyIC and said LPEI is LPEI$_{22k}$ and is covalently linked to three PEG$_{2K}$ moieties (LPEI-PEG 1:3).

PolyIC is bound to the polymeric conjugate via non-covalent or covalent bonds, wherein non-covalent binding is preferred. In a preferred embodiment, said polyIC is non-covalently bound to LPEI, preferably by ionic bonds.

Said LPEI of the polymeric conjugate of the polyplex for use according to the invention is covalently linked to one or more PEG moieties. In a preferred embodiment, said LPEI of the polymeric conjugate of the polyplex for use according to the invention is covalently linked to one PEG moiety (LPEI-PEG 1:1) or three PEG moieties (LPEI-PEG 1:3). In a more preferred embodiment, said LPEI of the polymeric conjugate of the polyplex for use according to the invention is covalently linked to one PEG moiety (LPEI-PEG 1:1).

In a preferred embodiment, said one or more PEG moieties each independently forms —NH—CO— bond with said LPEI.

In a preferred embodiment, said one or more PEG moieties each independently forms a bond selected from —NH—CO—, —CO—NH—, —S—C—, —S—S—, —O—CO— or —CO—O— with said linker.

In a more preferred embodiment, said one or more PEG moieties each independently forms a bond disulfide bond with said linker. In a more preferred embodiment, said one or more PEG moieties each independently forms a bond disulfide bond with said linker via —NH—CO—CH$_2$—S—S.

In a preferred embodiment, said one or more PEG moieties each independently forms —N—CO— or —NH—CO— bond with said LPEI.

In a preferred embodiment, said one or more PEG moieties each independently forms —N—CO— or —NH—CO— bond with said LPEI and a bond selected from —NH—CO—, —CO—NH—, —S—C—, —S—S—, —O—CO— or —CO—O— with said linker. In a preferred embodiment, said one or more PEG moieties each independently forms —N—CO— or —NH—CO— bond with said LPEI and —S—S-bond with said linker. In a preferred embodiment, each one of said one or more PEG moieties forms —NH—CO— or —N—CO— bonds with said LPEI and said linker.

In a preferred embodiment, said linker of the polyplex for use according to the invention is a peptide moiety (also referred to herein as peptide linker). The terms "peptide" and "peptide moiety" are used herein interchangeably and typically and preferably refer to a polymer of amino acid residues. The term "peptide moiety" typically and preferably includes also an amino acid polymer in which one or more amino acids are chemical analogues or modified derivatives of a corresponding naturally occurring amino acid.

In a preferred embodiment, said linker of the polyplex of the invention is a peptide moiety consisting 3 to 7 amino acid residues.

In a preferred embodiment, said dsRNA of the polyplex is polyIC, said LPEI of the polymeric conjugate is covalently linked to one PEG$_{2K}$ moiety (LPEI-PEG 1:1) or three PEG$_{2K}$ moieties (LPEI-PEG 1:3) and said linker is a peptide moiety, wherein preferably said peptide moiety consists of 3 to 7 amino acid residues. In a preferred embodiment, said dsRNA of the polyplex is polyIC, said LPEI of the polymeric conjugate is covalently linked to one PEG$_{2K}$ moiety (LPEI-PEG 1:1) and said linker is a peptide moiety, wherein preferably said peptide moiety consists of 3 to 7 amino acid residues. In a preferred embodiment, said dsRNA of the polyplex is polyIC, said LPEI of the polymeric conjugate is covalently linked to three PEG$_{2K}$ moieties (LPEI-PEG 1:3) and said linker is a peptide moiety, wherein preferably said peptide moiety consists of 3 to 7 amino acid residues.

In a preferred embodiment, said dsRNA of the polyplex is polyIC, said LPEI of the polymeric conjugate is LPEI$_{22k}$ and is covalently linked to one PEG moiety (LPEI-PEG 1:1) or three PEG moieties (LPEI-PEG 1:3) and said linker is a peptide moiety, wherein preferably said peptide moiety consists of 3 to 7 amino acid residues. In a preferred embodiment, said dsRNA of the polyplex is polyIC, said LPEI of the polymeric conjugate is LPEI$_{22k}$ and is covalently linked to three PEG moieties (LPEI-PEG 1:3) and said linker is a peptide moiety, wherein preferably said peptide moiety consists of 3 to 7 amino acid residues.

In a preferred embodiment, said dsRNA of the polyplex is polyIC, said LPEI of the polymeric conjugate is LPEI$_{22k}$ and is covalently linked to one PEG moiety (LPEI-PEG 1:1) or three PEG$_{2K}$ moieties (LPEI-PEG 1:3) and said linker is a peptide moiety, wherein preferably said peptide moiety consists of 3 to 7 amino acid residues. In a preferred embodiment, said dsRNA of the polyplex is polyIC, said LPEI of the polymeric conjugate is LPEI$_{22k}$ and is covalently linked to one PEG moiety (LPEI-PEG 1:1) and said linker is a peptide moiety, wherein preferably said peptide moiety consists of 3 to 7 amino acid residues. In a preferred embodiment, said dsRNA of the polyplex is polyIC, said LPEI of the polymeric conjugate is LPEI$_{22k}$ and is covalently linked to three PEG$_{2K}$ moieties (LPEI-PEG 1:3) and said linker is a peptide moiety, wherein preferably said peptide moiety consists of 3 to 7 amino acid residues.

In a preferred embodiment, said linker of the polyplex of the invention is a peptide moiety consisting 6 or 7 amino acid residues.

In a preferred embodiment, said dsRNA of the polyplex is polyIC, said LPEI of the polymeric conjugate is covalently linked to one PEG$_{2K}$ moiety (LPEI-PEG 1:1) or three PEG$_{2K}$ moieties (LPEI-PEG 1:3) and said linker is a peptide moiety, wherein preferably said peptide moiety consists of 6 or 7 amino acid residues. In a preferred embodiment, said dsRNA of the polyplex is polyIC, said LPEI of the polymeric conjugate is covalently linked to one PEG$_{2K}$ moiety (LPEI-PEG 1:1) and said linker is a peptide moiety, wherein preferably said peptide moiety consists of 6 or 7 amino acid residues. In a preferred embodiment, said dsRNA of the polyplex is polyIC, said LPEI of the polymeric conjugate is covalently linked to three PEG$_{2K}$ moieties (LPEI-PEG 1:3) and said linker is a peptide moiety, wherein preferably said peptide moiety consists of 6 or 7 amino acid residues.

In a preferred embodiment, said dsRNA of the polyplex is polyIC, said LPEI of the polymeric conjugate is LPEI$_{22k}$ and is covalently linked to one PEG moiety (LPEI-PEG 1:1) or three PEG moieties (LPEI-PEG 1:3) and said linker is a peptide moiety, wherein preferably said peptide moiety consists of 6 or 7 amino acid residues. In a preferred embodiment, said dsRNA of the polyplex is polyIC, said LPEI of the polymeric conjugate is LPEI$_{22k}$ and is covalently linked to one PEG moiety (LPEI-PEG 1:1) and said linker is a peptide moiety, wherein preferably said peptide moiety consists of 6 or 7 amino acid residues. In a preferred embodiment, said dsRNA of the polyplex is polyIC, said LPEI of the polymeric conjugate is LPEI$_{22k}$ and is covalently linked to three PEG moieties (LPEI-PEG 1:3) and said linker is a peptide moiety, wherein preferably said peptide moiety consists of 6 or 7 amino acid residues.

In a preferred embodiment, said dsRNA of the polyplex is polyIC, said LPEI of the polymeric conjugate is LPEI$_{22k}$ and is covalently linked to one PEG moiety (LPEI-PEG 1:1) or three PEG$_{2K}$ moieties (LPEI-PEG 1:3) and said linker is a peptide moiety, wherein preferably said peptide moiety consists of 6 or 7 amino acid residues. In a preferred embodiment, said dsRNA of the polyplex is polyIC, said LPEI of the polymeric conjugate is LPEI$_{22k}$ and is covalently linked to one PEG moiety (LPEI-PEG 1:1) and said linker is a peptide moiety, wherein preferably said peptide moiety consists of 6 or 7 amino acid residues. In a preferred embodiment, said dsRNA of the polyplex is polyIC, said LPEI of the polymeric conjugate is LPEI$_{22k}$ and is covalently linked to three PEG$_{2K}$ moieties (LPEI-PEG 1:3) and said linker is a peptide moiety, wherein preferably said peptide moiety consists of 6 or 7 amino acid residues.

The term "amino acid residue" or "amino acid" used interchangeable herein, refers to any natural or synthetic (i.e. non-natural) amino acid residue in its L- or D-stereoisomer. The term "amino acid residue" covers a separate amino acid; an amino acid attached to the end of a different moiety, such as a peptide moiety; or an amino acid attached to two different moieties, such as an amino acid included within a peptide chain. While a natural amino acid is any one of the twenty amino acid residues naturally occurring in proteins, the term synthetic/non-natural amino acid typically and preferably refers to any amino acid, modified amino acid and/or an analog thereof, that is not one of the twenty natural amino acids. Examples of non-natural amino acid include and are preferably ornithine, homolysine, 2,4-diaminobutyric acid (DABA), 2,3-diaminopropionic acid (DAP), 8-aminooctanoic acid (EAO), homophenylalanine, homo valine, or homoleucine.

In a certain embodiments, said linker is a peptide moiety comprising at least one, in particular two or three aromatic amino acid residues, such as phenylalanine, tryptophan, tyrosine or homophenylalanine.

In a preferred embodiment, said linker is a peptide moiety, wherein said peptide moiety includes —(NH—(CH$_2$)$_7$—CO)—. In a more preferred embodiment, said peptide moiety consists of 3 to 7 amino acid residues, wherein one amino acid residue is —(NH—(CH$_2$)$_7$—CO)—. In a preferred embodiment, said dsRNA of the polyplex is polyIC, said LPEI of the polymeric conjugate is preferably LPEI$_{22k}$ and is covalently linked to one PEG moiety (LPEI-PEG 1:1) or three PEG moieties (LPEI-PEG 1:3), wherein said PEG is preferably PEG$_{2K}$; and said peptide moiety consists of 3 to 7 amino acid residues, wherein one amino acid residue is —(NH—(CH$_2$)$_7$—CO)—. In a preferred embodiment, said dsRNA of the polyplex is polyIC, said LPEI of the polymeric conjugate is preferably LPEI$_{22k}$ and is covalently linked to one PEG moiety (LPEI-PEG 1:1), wherein said PEG is preferably PEG$_{2K}$; and said peptide moiety consists of 3 to 7 amino acid residues, wherein one amino acid residue is —(NH—(CH$_2$)$_7$—CO)—. In another preferred embodiment, said dsRNA of the polyplex is polyIC, said LPEI of the polymeric conjugate is preferably LPEI$_{22k}$ and is covalently linked to three PEG moieties (LPEI-PEG 1:3), wherein said PEG is preferably PEG$_{2K}$; and said peptide moiety consists of 3 to 7 amino acid residues, wherein one amino acid residue is —(NH—(CH$_2$)$_7$—CO)—.

In a preferred embodiment, said linker is a peptide moiety, wherein said peptide moiety includes —(NH—(CH$_2$)$_7$—CO)—. In a more preferred embodiment, said peptide moiety consists of 6 or 7 amino acid residues, wherein one amino acid residue is —(NH—(CH$_2$)$_7$—CO)—.

In a preferred embodiment, said dsRNA of the polyplex is polyIC, said LPEI of the polymeric conjugate is preferably LPEI$_{22k}$ and is covalently linked to one PEG moiety (LPEI-PEG 1:1) or three PEG moieties (LPEI-PEG 1:3), wherein said PEG is preferably PEG$_{2K}$; and said peptide moiety consists of 6 or 7 amino acid residues, wherein one amino acid residue is —(NH—(CH$_2$)$_7$—CO)—. In a preferred embodiment, said dsRNA of the polyplex is polyIC, said LPEI of the polymeric conjugate is preferably LPEI$_{22k}$ and is covalently linked to one PEG moiety (LPEI-PEG 1:1), wherein said PEG is preferably PEG$_{2K}$; and said peptide moiety consists of 6 or 7 amino acid residues, wherein one amino acid residue is —(NH—(CH$_2$)$_7$—CO)—.

In another preferred embodiment, said dsRNA of the polyplex is polyIC, said LPEI of the polymeric conjugate is preferably LPEI$_{22k}$ and is covalently linked to three PEG moieties (LPEI-PEG 1:3), wherein said PEG is preferably PEG$_{2K}$; and said peptide moiety consists of 6 or 7 amino acid residues, wherein one amino acid residue is —(NH—(CH$_2$)$_7$—CO)—.

In a preferred embodiment, said peptide moiety is —(NH—(CH$_2$)$_7$—CO)-Phe-Gly-Trp-Trp-Gly-Cys-(SEQ ID NO: 1) or —(NH—(CH$_2$)$_7$—CO)-Phe-Phe-(NH—CH$_2$—CH(NH$_2$)—CO)-Asp-Cys-(SEQ ID NO: 2). In a preferred embodiment, said peptide moiety is —(NH—(CH$_2$)$_7$—CO)-Phe-Gly-Trp-Trp-Gly-Cys-(SEQ ID NO: 1). In a preferred embodiment, said peptide moiety is —(NH—(CH$_2$)$_7$—CO)-Phe-Phe-(NH—CH$_2$—CH(NH$_2$)—CO)-Asp-Cys- (SEQ ID NO: 2).

In a preferred embodiment, said peptide moiety is —(NH—(CH$_2$)$_7$—CO)-Phe-Gly-Trp-Trp-Gly-Cys-(SEQ ID NO: 1) or —(NH—(CH$_2$)$_7$—CO)-Phe-Phe-(NH—CH$_2$—CH(NH$_2$)—CO)-Asp-Cys-(SEQ ID NO: 2), and said peptide moiety of SEQ ID NO: 1 or 2 is linked via the mercapto group of its Cys residue to said targeting moiety or said one or more PEG moieties. In a preferred embodiment, said peptide moiety is —(NH—(CH$_2$)$_7$—CO)-Phe-Gly-Trp-Trp-Gly-Cys-(SEQ ID NO: 1) or —(NH—(CH$_2$)$_7$—CO)-Phe-Phe-(NH—CH$_2$—CH(NH$_2$)—CO)-Asp-Cys-(SEQ ID NO: 2) and said peptide moiety of SEQ ID NO: 1 or 2 is linked via the mercapto group of its Cys residue to the targeting moiety. In a preferred embodiment, said peptide moiety is —(NH—(CH$_2$)$_7$—CO)-Phe-Gly-Trp-Trp-Gly-Cys- (SEQ ID NO: 1) or —(NH—(CH$_2$)$_7$—CO)-Phe-Phe-(NH—CH$_2$—CH(NH$_2$)—CO)-Asp-Cys- (SEQ ID NO: 2) and said peptide moiety of SEQ ID NO: 1 or 2 is linked via the mercapto group of its Cys residue to said one or more PEG moieties. In a preferred embodiment, said peptide moiety is —(NH—(CH$_2$)$_7$—CO)-Phe-Gly-Trp-Trp-Gly-Cys- (SEQ ID NO: 1) and said peptide moiety of SEQ ID NO: 1 is linked via the mercapto group of its Cys residue to said one or more PEG moieties. In a preferred embodiment, said peptide moiety is —(NH—(CH$_2$)$_7$—CO)-Phe-Phe-(NH—CH$_2$—CH(NH$_2$)—CO)-Asp-Cys-(SEQ ID NO: 2) and said peptide moiety of SEQ ID NO: 2 is linked via the mercapto group of its Cys residue to said one or more PEG moieties.

In a preferred embodiment, said dsRNA of the polyplex is polyIC, said LPEI of the polymeric conjugate is covalently linked to one PEG$_{2K}$ moiety (LPEI-PEG 1:1) and said peptide moiety is —(NH—(CH$_2$)$_7$—CO)-Phe-Gly-Trp-Trp-Gly-Cys- (SEQ ID NO: 1), and preferably said peptide moiety of SEQ ID NO: 1 is linked via the mercapto group of its Cys residue to said one or more PEG moieties. In a preferred embodiment, said dsRNA of the polyplex is polyIC, said LPEI of the polymeric conjugate is covalently linked to one PEG$_{2K}$ moiety (LPEI-PEG 1:1) and said peptide moiety is —(NH—(CH$_2$)$_7$—CO)-Phe-Phe-(NH—CH$_2$—CH(NH$_2$)—CO)-Asp-Cys- (SEQ ID NO: 2), and preferably said peptide moiety of SEQ ID NO: 2 is linked via the mercapto group of its Cys residue to said one or more PEG moieties. In a preferred embodiment, said dsRNA of the polyplex is polyIC, said LPEI of the polymeric conjugate is covalently linked to three PEG$_{2K}$ moieties (LPEI-PEG 1:3) and said peptide moiety is —(NH—(CH$_2$)$_7$—CO)-Phe-Gly-Trp-Trp-Gly-Cys- (SEQ ID NO: 1), and preferably said peptide moiety of SEQ ID NO: 1 is linked via the mercapto group of its Cys residue to said one or more PEG moieties. In a preferred embodiment, said dsRNA of the polyplex is polyIC, said LPEI of the polymeric conjugate is covalently linked to three PEG$_{2K}$ moiety (LPEI-PEG 1:3) and said peptide moiety is —(NH—(CH$_2$)$_7$—CO)-Phe-Phe-(NH—CH$_2$—CH(NH$_2$)—CO)-Asp-Cys- (SEQ ID NO: 2), and preferably said peptide moiety of SEQ ID NO: 2 is linked via the mercapto group of its Cys residue to said one or more PEG moieties.

In a preferred embodiment, said dsRNA of the polyplex is polyIC, said LPEI of the polymeric conjugate is LPEI$_{22k}$ and is covalently linked to one PEG moiety (LPEI-PEG 1:1) and said peptide moiety is —(NH—(CH$_2$)$_7$—CO)-Phe-Gly-Trp-Trp-Gly-Cys- (SEQ ID NO: 1), and preferably said peptide moiety of SEQ ID NO: 1 is linked via the mercapto group of its Cys residue to said one or more PEG moieties. In a preferred embodiment, said dsRNA of the polyplex is polyIC, said LPEI of the polymeric conjugate is LPEI$_{22k}$ and is covalently linked to one PEG moiety (LPEI-PEG 1:1) and said peptide moiety is —(NH—(CH$_2$)$_7$—CO)-Phe-Phe-(NH—CH$_2$—CH(NH$_2$)—CO)-Asp-Cys- (SEQ ID NO: 2), and preferably said peptide moiety of SEQ ID NO: 2 is linked via the mercapto group of its Cys residue to said one or more PEG moieties.

In a preferred embodiment, said dsRNA of the polyplex is polyIC, said LPEI of the polymeric conjugate is LPEI$_{22k}$ and is covalently linked to three PEG moiety (LPEI-PEG 1:3) and said peptide moiety is —(NH—(CH$_2$)$_7$—CO)-Phe-Gly-Trp-Trp-Gly-Cys- (SEQ ID NO: 1), and preferably said peptide moiety of SEQ ID NO: 1 is linked via the mercapto group of its Cys residue to said one or more PEG moieties. In a preferred embodiment, said dsRNA of the polyplex is polyIC, said LPEI of the polymeric conjugate is LPEI$_{22k}$ and is covalently linked to three PEG moiety (LPEI-PEG 1:3) and said peptide moiety is —(NH—(CH$_2$)$_7$—CO)-Phe-Phe-(NH—CH$_2$—CH(NH$_2$)—CO)-Asp-Cys- (SEQ ID NO: 2), and preferably said peptide moiety of SEQ ID NO: 2 is linked via the mercapto group of its Cys residue to said one or more PEG moieties.

In a preferred embodiment, said dsRNA of the polyplex is polyIC, said LPEI of the polymeric conjugate is LPEI$_{22k}$ and is covalently linked to one PEG$_{2K}$ moiety (LPEI-PEG 1:1) and said peptide moiety is —(NH—(CH$_2$)$_7$—CO)-Phe-Gly-Trp-Trp-Gly-Cys- (SEQ ID NO: 1), and preferably said peptide moiety of SEQ ID NO: 1 is linked via the mercapto group of its Cys residue to said one or more PEG moieties. In a preferred embodiment, said dsRNA of the polyplex is polyIC, said LPEI of the polymeric conjugate is LPEI$_{22k}$ and is covalently linked to one PEG$_{2K}$ moiety (LPEI-PEG 1:1) and said peptide moiety is —(NH—(CH$_2$)$_7$—CO)-Phe-Phe-(NH—CH$_2$—CH(NH$_2$)—CO)-Asp-Cys- (SEQ ID NO: 2), and preferably said peptide moiety of SEQ ID NO: 2 is linked via the mercapto group of its Cys residue to said one or more PEG moieties.

In a preferred embodiment, said dsRNA of the polyplex is polyIC, said LPEI of the polymeric conjugate is LPEI$_{22k}$ and is covalently linked to three PEG$_{2K}$ moieties (LPEI-PEG 1:3) and said peptide moiety is —(NH—(CH$_2$)$_7$—CO)-Phe-Gly-Trp-Trp-Gly-Cys- (SEQ ID NO: 1). In a preferred embodiment, said dsRNA of the polyplex is polyIC, said LPEI of the polymeric conjugate is LPEI$_{22k}$ and is covalently linked to three PEG$_{2K}$ moiety (LPEI-PEG 1:3) and said peptide moiety is —(NH—(CH$_2$)$_7$—CO)-Phe-Phe-(NH—CH$_2$—CH(NH$_2$)—CO)-Asp-Cys-(SEQ ID NO: 2).

The polyplex for use according to the invention, wherein said polymeric conjugate is selected from formula (a), (b), (c) or (d):
(a) T-(NH—(CH$_2$)$_7$—CO)-Phe-Phe-(NH—CH$_2$—CH(NH$_2$)—CO)-Asp-Cys-PEG-LPEI (SEQ ID NO: 17);
(b) T-(NH—(CH$_2$)$_7$—CO)-Phe-Gly-Trp-Trp-Gly-Cys-PEG-LPEI (SEQ ID NO: 18);
(c) [T-(NH—(CH$_2$)$_7$—CO)-Phe-Phe-(NH—CH$_2$—CH(NH$_2$)—CO)-Asp-Cys-PEG (SEQ ID NO: 19)]$_3$-LPEI; or
(d) [T-(NH—(CH$_2$)$_7$—CO)-Phe-Gly-Trp-Trp-Gly-Cys-PEG (SEQ ID NO: 20)]$_3$-LPEI;
and wherein said T represents said targeting moiety.

In a preferred embodiment, said polymeric conjugate is (a) T-(NH—(CH$_2$)$_7$—CO)-Phe-Phe-(NH—CH$_2$—CH(NH$_2$)—CO)-Asp-Cys-PEG-LPEI (SEQ ID NO: 17), wherein said T represents said targeting moiety; and wherein preferably said dsRNA is polyIC. In a preferred embodiment, said polymeric conjugate is (b) T-(NH—(CH$_2$)$_7$—CO)-Phe-Gly-Trp-Trp-Gly-Cys-PEG-LPEI (SEQ ID NO: 18), wherein said T represents said targeting moiety; and wherein preferably said dsRNA is polyIC. In a preferred embodiment, said polymeric conjugate is (c) [T-(NH—(CH$_2$)$_7$—CO)-Phe-Phe-(NH—CH$_2$—CH(NH$_2$)—CO)-Asp-Cys-PEG (SEQ ID NO: 19)]$_3$-LPEI, wherein said T represents said targeting moiety; and wherein preferably said dsRNA is polyIC. In a preferred embodiment, said polymeric conjugate is (d) [T-(NH—(CH$_2$)$_7$—CO)-Phe-Gly-Trp-Trp-Gly-Cys-PEG (SEQ ID NO: 20)]$_3$-LPEI, wherein said T represents said targeting moiety; and wherein preferably said dsRNA is polyIC.

In a preferred embodiment, said polymeric conjugate is (a) T-(NH—(CH$_2$)$_7$—CO)-Phe-Phe-(NH—CH$_2$—CH(NH$_2$)—CO)-Asp-Cys-PEG-LPEI$_{22k}$ (SEQ ID NO: 21), wherein said T represents said targeting moiety; and wherein preferably said dsRNA is polyIC. In a preferred embodiment, said polymeric conjugate is (b) T-(NH—(CH$_2$)$_7$—CO)-Phe-Gly-Trp-Trp-Gly-Cys-PEG-LPEI$_{22k}$ (SEQ ID NO: 22), wherein said T represents said targeting moiety; and wherein preferably said dsRNA is polyIC. In a preferred embodiment, said polymeric conjugate is (c) [T-(NH—(CH$_2$)$_7$—CO)-Phe-Phe-(NH—CH$_2$—CH(NH$_2$)—CO)-Asp-Cys-PEG (SEQ ID NO: 19)]$_3$-LPEI$_{22k}$, wherein said T represents said targeting moiety; and wherein preferably said dsRNA is polyIC. In a preferred embodiment, said polymeric conjugate is (d) [T-(NH—(CH$_2$)$_7$—CO)-Phe-Gly-Trp-Trp-Gly-Cys-PEG (SEQ ID NO: 20)]$_3$-LPEI$_{22k}$, wherein said T represents said targeting moiety; and wherein preferably said dsRNA is polyIC.

In a preferred embodiment, said polymeric conjugate is (a) T-(NH—(CH$_2$)$_7$—CO)-Phe-Phe-(NH—CH$_2$—CH(NH$_2$)—CO)-Asp-Cys-PEG$_{2k}$-LPEI (SEQ ID NO: 23), wherein said T represents said targeting moiety; and wherein preferably said dsRNA is polyIC. In a preferred embodiment, said polymeric conjugate is (b) T-(NH—(CH$_2$)$_7$—CO)-Phe-Gly-Trp-Trp-Gly-Cys-PEG$_{2k}$-LPEI (SEQ ID NO: 24), wherein said T represents said targeting moiety; and wherein preferably said dsRNA is polyIC. In a preferred embodiment, said polymeric conjugate is (c) [T-(NH—(CH$_2$)$_7$—CO)-Phe-Phe-(NH—CH$_2$—CH(NH$_2$)—CO)-Asp-Cys-PEG$_{2k}$ (SEQ ID NO: 25)]$_3$-LPEI, wherein said T represents said targeting moiety; and wherein preferably said dsRNA is polyIC. In a preferred embodiment, said polymeric conjugate is (d) [T-(NH—(CH$_2$)$_7$—CO)-Phe-Gly-Trp-Trp-Gly-Cys-PEG$_{2k}$ (SEQ ID NO: 26)]$_3$-LPEI linked to said targeting moieties, wherein said T represents said targeting moiety; and wherein preferably said dsRNA is polyIC.

In a preferred embodiment, said polymeric conjugate is (a) T-(NH—(CH$_2$)$_7$—CO)-Phe-Phe-(NH—CH$_2$—CH(NH$_2$)—CO)-Asp-Cys-PEG$_{2k}$-LPEI$_{22k}$ (SEQ ID NO: 27), wherein said T represents said targeting moiety; and wherein preferably said dsRNA is polyIC. In a preferred embodiment, said polymeric conjugate is (b) T-(NH—(CH$_2$)$_7$—CO)-Phe-Gly-Trp-Trp-Gly-Cys-PEG$_{2k}$-LPEI$_{22k}$ (SEQ ID NO: 28), wherein said T represents said targeting moiety; and wherein preferably said dsRNA is polyIC. In a preferred embodiment, said polymeric conjugate is (c) [T-(NH—(CH$_2$)$_7$—CO)-Phe-Phe-(NH—CH$_2$—CH(NH$_2$)—CO)-Asp-Cys-PEG$_{2k}$ (SEQ ID NO: 25)]$_3$-LPEI$_{22k}$, wherein said T represents said targeting moiety; and wherein preferably said dsRNA is polyIC. In a preferred embodiment, said polymeric conjugate is (d) [T-(NH—(CH$_2$)$_7$—CO)-Phe-Gly-Trp-Trp-Gly-Cys-PEG$_{2k}$ (SEQ ID NO: 26)]$_3$-LPEI$_{22k}$, wherein said T represents said targeting moiety; and wherein preferably said dsRNA is polyIC.

The polyplex for use according to the invention, wherein said polymeric conjugate is selected from formula (a), (b), (c) or (d):

(a) T-(NH—(CH$_2$)$_7$—CO)-Phe-Phe-(NH—CH$_2$—CH(NH$_2$)—CO)-Asp-Cys-PEG-LPEI (SEQ ID NO: 17);

(b) T-(NH—(CH$_2$)$_7$—CO)-Phe-Gly-Trp-Trp-Gly-Cys-PEG-LPEI (SEQ ID NO: 18);

(c) [T-(NH—(CH$_2$)$_7$—CO)-Phe-Phe-(NH—CH$_2$—CH(NH$_2$)—CO)-Asp-Cys-PEG (SEQ ID NO: 19)]$_3$-LPEI; or (d) [T-(NH—(CH$_2$)$_7$—CO)-Phe-Gly-Trp-Trp-Gly-Cys-PEG (SEQ ID NO: 20)]$_3$-LPEI;

wherein said T represents said targeting moiety, and wherein said PEG moiety is of formula (v)

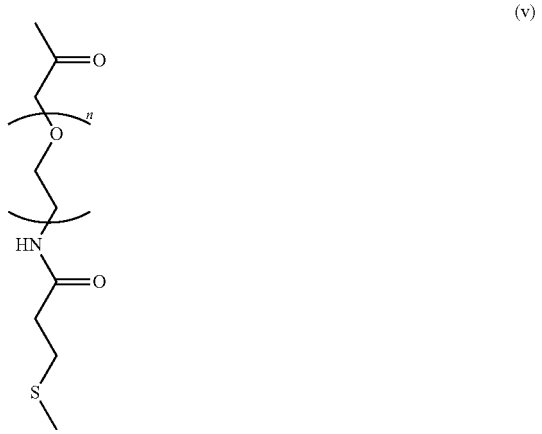

(v)

wherein n is 40-45, and wherein said PEG moiety of formula (v) is linked to the Cys residue via a disulfide bond.

In a preferred embodiment, said polymeric conjugate is (a) T-(NH—(CH$_2$)$_7$—CO)-Phe-Phe-(NH—CH$_2$—CH(NH$_2$)—CO)-Asp-Cys-PEG-LPEI (SEQ ID NO: 17), wherein said T represents said targeting moiety, and wherein said PEG moiety is of formula (v), n is 40-45 and said PEG moiety of formula (v) is linked to the Cys residue via a disulfide bond; and wherein preferably said dsRNA is polyIC. In a preferred embodiment, said polymeric conjugate is (b) T-(NH—(CH$_2$)$_7$—CO)-Phe-Gly-Trp-Trp-Gly-Cys-PEG-LPEI (SEQ ID NO: 18), wherein said T represents said targeting moiety, and wherein said PEG moiety is of formula (v), n is 40-45 and said PEG moiety of formula (v) is linked to the Cys residue via a disulfide bond; and wherein preferably said dsRNA is polyIC. In a preferred embodiment, said polymeric conjugate is (c) [T-(NH—(CH$_2$)$_7$—CO)-Phe-Phe-(NH—CH$_2$—CH(NH$_2$)—CO)-Asp-Cys-PEG (SEQ ID NO: 19)]$_3$-LPEI, wherein said T represents said targeting moiety, and wherein said PEG moiety is of formula (v), n is 40-45 and said PEG moiety of formula (v) is linked to the Cys residue via a disulfide bond; and wherein preferably said dsRNA is polyIC. In a preferred embodiment, said polymeric conjugate is (d) [T-(NH—(CH$_2$)$_7$—CO)-Phe-Gly-Trp-Trp-Gly-Cys-PEG (SEQ ID NO: 20)]$_3$-LPEI, wherein said T represents said targeting moiety, and wherein said PEG moiety is of formula (v), wherein n is 40-45 and said PEG moiety of formula (v) is linked to the Cys residue via a disulfide bond; and wherein preferably said dsRNA is polyIC.

In a preferred embodiment, said polymeric conjugate is (a) T-(NH—(CH$_2$)$_7$—CO)-Phe-Phe-(NH—CH$_2$—CH(NH$_2$)—CO)-Asp-Cys-PEG-LPEI$_{22k}$ (SEQ ID NO: 21), wherein said T represents said targeting moiety; wherein said PEG moiety is of formula (v), n is 40-45 and said PEG moiety of formula (v) is linked to the Cys residue via a disulfide bond; and wherein preferably said dsRNA is polyIC. In a preferred embodiment, said polymeric conjugate is (b) T-(NH—(CH$_2$)$_7$—CO)-Phe-Gly-Trp-Trp-Gly-Cys-PEG-LPEI$_{22k}$ (SEQ ID NO: 22), wherein said T represents said targeting moiety; wherein said PEG moiety is of formula (v), n is 40-45 and said PEG moiety of formula (v) is linked to the Cys residue via a disulfide bond; and wherein preferably said dsRNA is polyIC. In a preferred embodiment, said polymeric conjugate is (c) [T-(NH—(CH$_2$)$_7$—CO)-Phe-Phe-(NH—CH$_2$—CH(NH$_2$)—CO)-Asp-Cys-PEG (SEQ ID NO: 17)]$_3$-LPEI$_{22k}$, wherein said T represents said targeting moiety; wherein said PEG moiety is of formula (v), n is 40-45 and said PEG moiety of formula (v) is linked to the Cys residue via a disulfide bond; and wherein preferably said dsRNA is polyIC. In a preferred embodiment, said polymeric conjugate is (d) [T-(NH—(CH$_2$)$_7$—CO)-Phe-Gly-Trp-Trp-Gly-Cys-PEG (SEQ ID NO: 18)]$_3$-LPEI$_{22k}$, wherein said T represents said targeting moiety; wherein said PEG moiety is of formula (v), n is 40-45 and said PEG moiety of formula (v) is linked to the Cys residue via a disulfide bond; and wherein preferably said dsRNA is polyIC.

In a preferred embodiment, said polymeric conjugate is (a) T-(NH—(CH$_2$)$_7$—CO)-Phe-Phe-(NH—CH$_2$—CH(NH$_2$)—CO)-Asp-Cys-PEG$_{2k}$-LPEI (SEQ ID NO: 23), wherein said T represents said targeting moiety; wherein said PEG moiety is of formula (v), n is 40-45 and said PEG moiety of formula (v) is linked to the Cys residue via a disulfide bond; and wherein preferably said dsRNA is polyIC. In a preferred embodiment, said polymeric conjugate is (b) T-(NH—(CH$_2$)$_7$—CO)-Phe-Gly-Trp-Trp-Gly-Cys-PEG$_{2k}$-LPEI (SEQ ID NO: 24), wherein said T represents said targeting moiety; wherein said PEG moiety is of formula (v), n is 40-45 and said PEG moiety of formula (v) is linked to the Cys residue via a disulfide bond; and wherein preferably said dsRNA is polyIC. In a preferred embodiment, said polymeric conjugate is (c) [T-(NH—(CH$_2$)$_7$—CO)-Phe-Phe-(NH—CH$_2$—CH(NH$_2$)—CO)-Asp-Cys-PEG$_{2k}$ (SEQ ID NO: 25)]$_3$-LPEI, wherein said T represents said targeting moiety; wherein said PEG moiety is of formula (v), n is 40-45 and said PEG moiety of formula (v) is linked to the Cys residue via a disulfide bond; and wherein preferably said dsRNA is polyIC. In a preferred embodiment, said polymeric conjugate is (d) [T-(NH—(CH$_2$)$_7$—CO)-Phe-Gly-Trp-Trp-Gly-Cys-PEG$_{2k}$ (SEQ ID NO: 26)]$_3$-LPEI linked to said targeting moieties, wherein said T represents said targeting moiety; wherein said PEG moiety is of formula (v), n is 40-45 and said PEG moiety of formula (v) is linked to the Cys residue via a disulfide bond; and wherein preferably said dsRNA is polyIC.

In a preferred embodiment, said polymeric conjugate is (a) T-(NH—(CH$_2$)$_7$—CO)-Phe-Phe-(NH—CH$_2$—CH(NH$_2$)—CO)-Asp-Cys-PEG$_{2k}$-LPEI$_{22k}$ (SEQ ID NO: 27), wherein said T represents said targeting moiety; wherein said PEG moiety is of formula (v), n is 40-45 and said PEG moiety of formula (v) is linked to the Cys residue via a disulfide bond; and wherein preferably said dsRNA is polyIC. In a preferred embodiment, said polymeric conjugate is (b) T-(NH—(CH$_2$)$_7$—CO)-Phe-Gly-Trp-Trp-Gly-Cys-PEG$_{2k}$-LPEI$_{22k}$ (SEQ ID NO: 28), wherein said T represents said targeting moiety; wherein said PEG moiety is of formula (v), n is 40-45 and said PEG moiety of formula (v) is linked to the Cys residue via a disulfide bond; and wherein preferably said dsRNA is polyIC. In a preferred embodiment, said polymeric conjugate is (c) [T-(NH—(CH$_2$)$_7$—CO)-Phe-Phe-(NH—CH$_2$—CH(NH$_2$)—CO)-Asp-Cys-PEG$_{2k}$ (SEQ ID NO: 25)]3-LPEI$_{22k}$, wherein said T represents said targeting moiety; wherein said PEG moiety is of formula (v), n is 40-45 and said PEG moiety of formula (v) is linked to the Cys residue via a disulfide bond; and wherein preferably said dsRNA is polyIC. In a preferred embodiment, said polymeric conjugate is (d) [T-(NH—(CH$_2$)$_7$—CO)-Phe-Gly-Trp-Trp-Gly-Cys-PEG$_{2k}$ (SEQ ID NO: 26)]$_3$-LPEI$_{22k}$, wherein said T represents said targeting moiety; wherein said PEG moiety is of formula (v), n is 40-45 and said PEG moiety of formula (v) is linked to the Cys residue via a disulfide bond; and wherein preferably said dsRNA is polyIC.

In a preferred embodiment, said polymeric conjugate is selected from formula (i), (ii), (iii) or (iv):

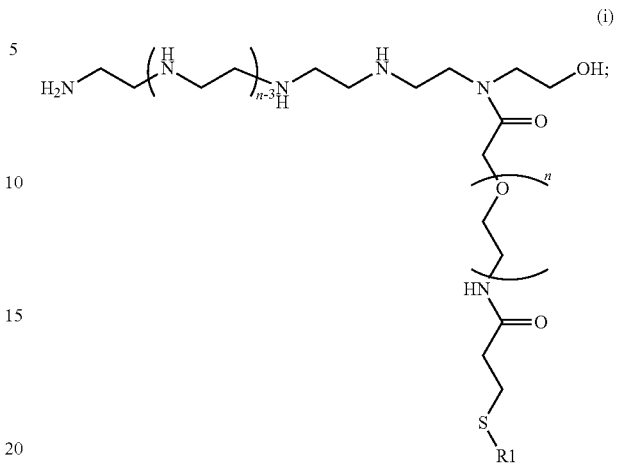

(i)

wherein R1 is

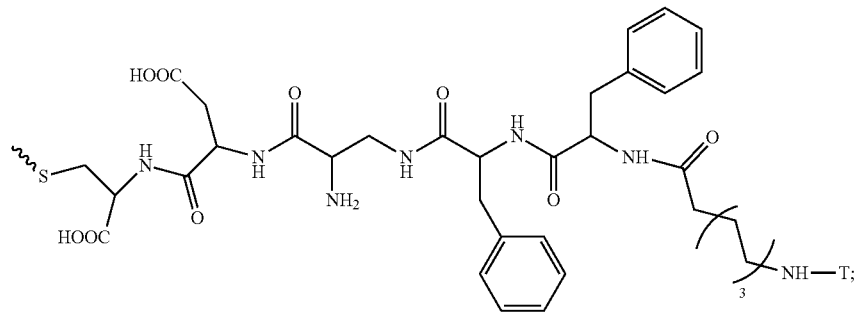

(SEQ ID NO: 29)

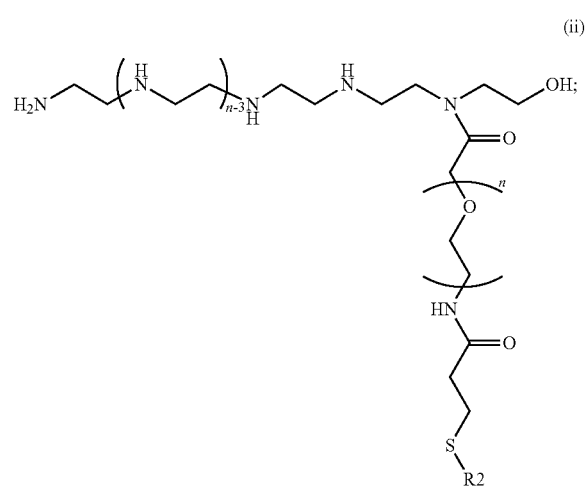

(ii)

wherein R2 is
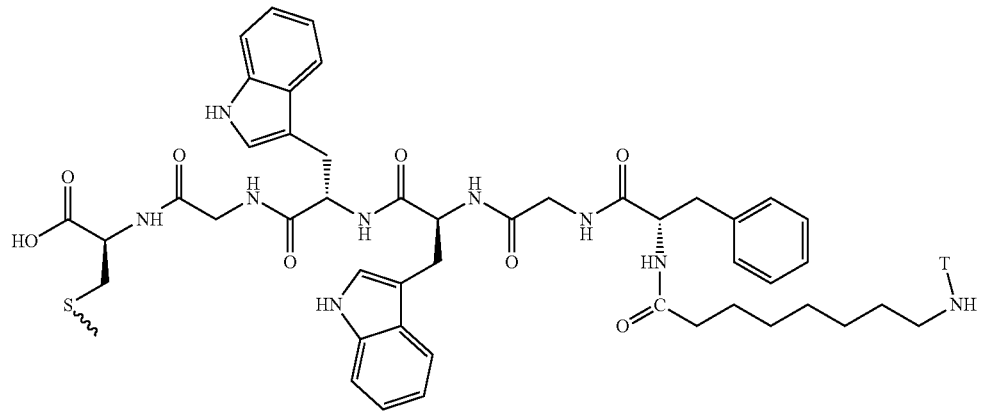
(SEQ ID NO: 30)
(iii) (iv)
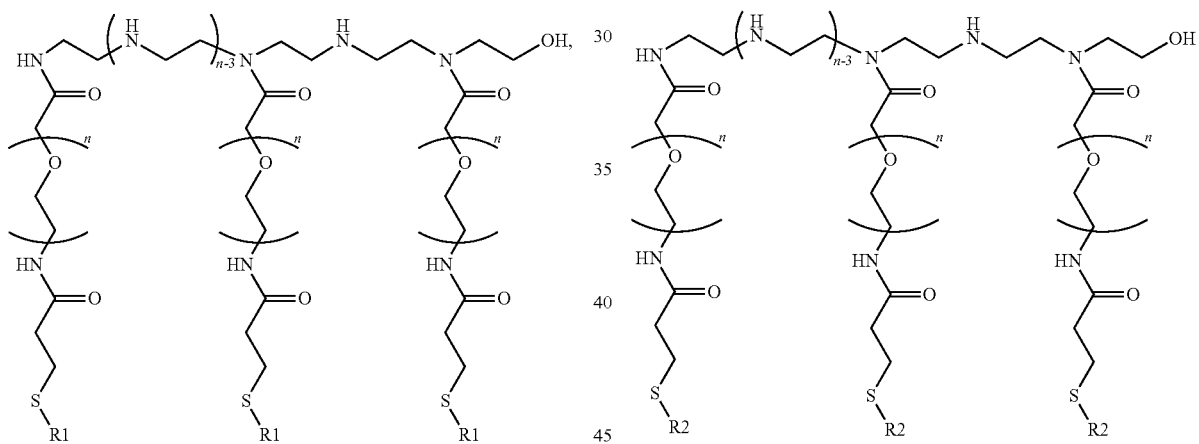
wherein R1 is
(SEQ ID NO: 29)
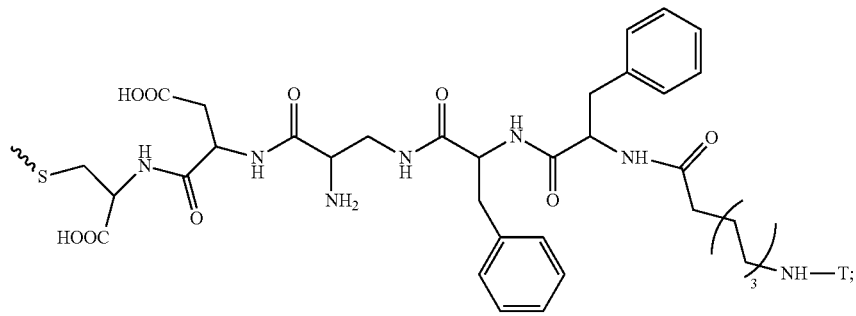

wherein R2 is (SEQ ID NO: 30)

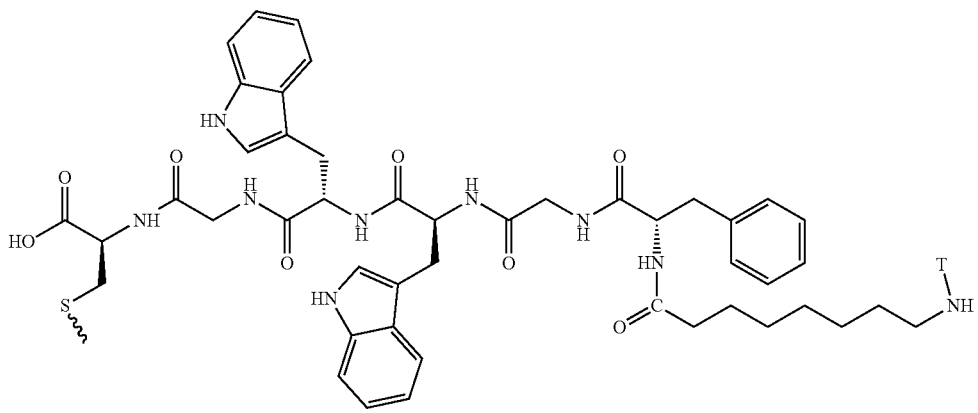

wherein said T represents said targeting moiety and wherein n is 40-45.

In the polyplex for use according to the invention, the targeting moiety is capable of binding to a cancer antigen, and the cancer antigen is prostate surface membrane antigen (PSMA). The targeting moiety may be a native, natural or modified ligand or a paralog thereof, or a non-native ligand such as an antibody, a single-chain variable fragment (scFv), or an antibody mimetic such as an affibody, to any one of the cancer antigens.

In a preferred embodiment, said targeting moiety is HOOC(CH$_2$)$_2$—CH(COOH)—NH—CO—NH—CH(COOH)—(CH$_2$)$_2$—CO— referred herein as DUPA residue.

In a preferred embodiment, said targeting moiety is HOOC(CH$_2$)$_2$—CH(COOH)—NH—CO—NH—CH(COOH)—(CH$_2$)$_2$—CO— (DUPA residue) and said linker is the peptide moiety —(NH—(CH$_2$)$_7$—CO)-Phe-Gly-Trp-Trp-Gly-Cys- (SEQ ID NO: 1) or —(NH—(CH$_2$)$_7$—CO)-Phe-Phe-(NH—CH$_2$—CH(NH$_2$)—CO)-Asp-Cys- (SEQ ID NO: 2). In a preferred embodiment, said targeting moiety is HOOC(CH$_2$)$_2$—CH(COOH)—NH—CO—NH—CH(COOH)—(CH$_2$)$_2$—CO— (DUPA residue) and said linker is the peptide moiety —(NH—(CH$_2$)$_7$—CO)-Phe-Gly-Trp-Trp-Gly-Cys- (SEQ ID NO: 1). In a preferred embodiment, said targeting moiety is HOOC(CH$_2$)$_2$—CH(COOH)—NH—CO—NH—CH(COOH)—(CH$_2$)$_2$—CO— (DUPA residue) and said linker is the peptide moiety —(NH—(CH$_2$)$_7$—CO)-Phe-Phe-(NH—CH$_2$—CH(NH$_2$)—CO)-Asp-Cys- (SEQ ID NO: 2).

Figure 2A:
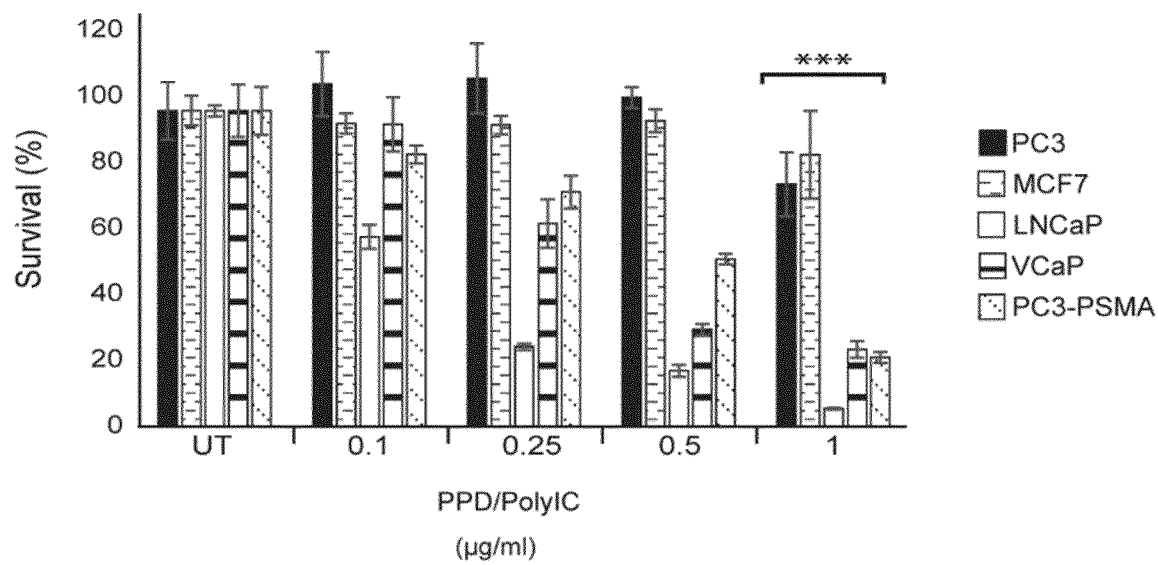
FIG. 2: Selective cell death and apoptosis in PSMA-overexpressing cells caused by treatment with PPD/polyIC.
Figure 2A:
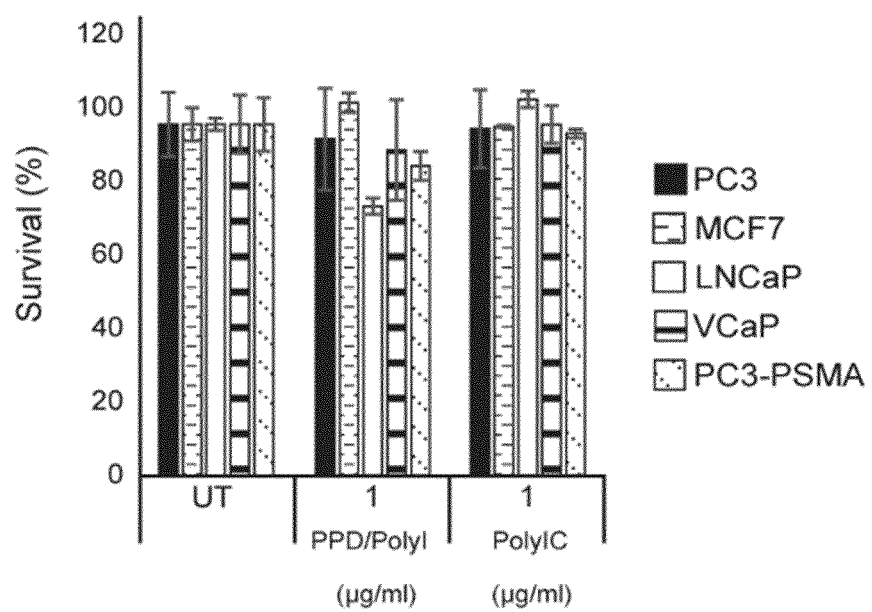
Figure 2B:
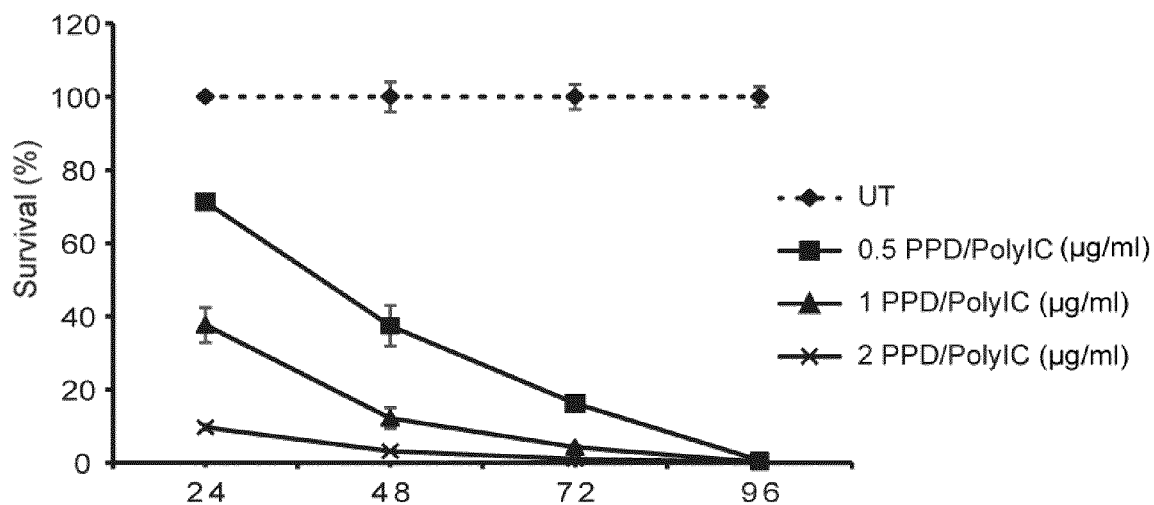

Access of DUPA to its PSMA binding site is through a deep, gradually narrowing channel with two hydrophobic cavities (Kularatne S A, et al. (2009) Design, synthesis, and preclinical evaluation of prostate-specific membrane antigen targeted (99m)Tc-radioimaging agents. Mol Pharm 6(3): 790-800). The linker of the invention, especially the peptide linker, such as SEQ ID NO: 1 and 2 fit to the structure and chemistry of the entry tunnel. The polyplex of the invention thus successfully led to selective delivery and internalization of polyIC to PSMA overexpressing cells and especially to CRPC cells (FIGS. 2A and 6). Following internalization, polyIC activated apoptotic pathways within 8 h and induced to complete cell eradication after 96 h (FIG. 2B, C). The polyplex of the invention combines high selectivity and rapid killing and is thus expected to eliminate tumor cells before they are able to develop resistance, while toxic side effects are substantially reduced.

In a more preferred embodiment, said targeting moiety is HOOC(CH$_2$)$_2$—CH(COOH)—NH—CO—NH—CH(COOH)—(CH$_2$)$_2$—CO— (DUPA residue), and said polymeric conjugate is selected from formula (i), (ii), (iii) or (iv). In another preferred embodiment, said dsRNA is polyIC, said targeting moiety is HOOC(CH$_2$)$_2$—CH(COOH)—NH—CO—NH—CH(COOH)—(CH$_2$)$_2$—CO— (DUPA residue), and said polymeric conjugate is selected from formula (i), (ii), (iii) or (iv).

In a preferred embodiment, said targeting moiety is HOOC(CH$_2$)$_2$—CH(COOH)—NH—CO—NH—CH(COOH)—(CH$_2$)$_2$—CO— (DUPA residue), and said polymeric conjugate is selected from formula (i) or (ii). In another preferred embodiment, said targeting moiety is HOOC(CH$_2$)$_2$—CH(COOH)—NH—CO—NH—CH(COOH)—(CH$_2$)$_2$—CO— (DUPA residue), and said polymeric conjugate is selected from formula (iii) or (iv).

In a preferred embodiment, said targeting moiety is said DUPA residue and said polymeric conjugate is the diconjugate of formula (i) linked to said DUPA residue. In a preferred embodiment, said targeting moiety is said DUPA residue and said polymeric conjugate is the diconjugate of formula (ii) linked to said DUPA residue. In a preferred embodiment, said targeting moiety is said DUPA residue and said polymeric conjugate is the diconjugate of formula (iii) linked to said DUPA residues. In a preferred embodiment, said targeting moiety is said DUPA residue and said polymeric conjugate is the diconjugate of formula (iv) linked to said DUPA residues.

In a preferred embodiment, said targeting moiety is HOOC(CH$_2$)$_2$—CH(COOH)—NH—CO—NH—CH(COOH)—(CH$_2$)$_2$—CO— (DUPA residue), and said polymeric conjugate is formula (i). In a preferred embodiment, said targeting moiety is HOOC(CH$_2$)$_2$—CH(COOH)—NH—CO—NH—CH(COOH)—(CH$_2$)$_2$—CO— (DUPA residue), and said polymeric conjugate is formula (ii). In a preferred embodiment, said targeting moiety is HOOC(CH$_2$)$_2$—CH(COOH)—NH—CO—NH—CH(COOH)—(CH$_2$)$_2$—CO— (DUPA residue), and said polymeric conjugate is formula (iii). In a preferred embodiment, said targeting moiety is HOOC(CH$_2$)$_2$—CH(COOH)—NH—CO—NH—CH(COOH)—(CH$_2$)$_2$—CO— (DUPA residue), and said polymeric conjugate is formula (iv).

In a preferred embodiment, said dsRNA of the polyplex is polyIC, said targeting moiety is HOOC(CH$_2$)$_2$—CH(COOH)—NH—CO—NH—CH(COOH)—(CH$_2$)$_2$—CO—

(DUPA residue), and said polymeric conjugate is selected from formula (i) or (ii). In another preferred embodiment, said dsRNA of the polyplex is polyIC, said targeting moiety is HOOC(CH$_2$)$_2$—CH(COOH)—NH—CO—NH—CH(COOH)—(CH$_2$)$_2$—CO— (DUPA residue), and said polymeric conjugate is selected from formula (iii) or (iv).

In a preferred embodiment, said dsRNA of the polyplex is polyIC, said targeting moiety is said DUPA residue and said polymeric conjugate is the diconjugate of formula (i) linked to said DUPA residue. In a preferred embodiment, said dsRNA of the polyplex is polyIC, said targeting moiety is said DUPA residue and said polymeric conjugate is the diconjugate of formula (ii) linked to said DUPA residue. In a preferred embodiment, said dsRNA of the polyplex is polyIC, said targeting moiety is said DUPA residue and said polymeric conjugate is the diconjugate of formula (iii) linked to said DUPA residues. In a preferred embodiment, said dsRNA of the polyplex is polyIC, said targeting moiety is said DUPA residue and said polymeric conjugate is the diconjugate of formula (iv) linked to said DUPA residues.

In a preferred embodiment, said dsRNA of the polyplex is polyIC, said targeting moiety is HOOC(CH$_2$)$_2$—CH(COOH)—NH—CO—NH—CH(COOH)—(CH$_2$)$_2$—CO— (DUPA residue), and said polymeric conjugate is formula (i). In a preferred embodiment, said dsRNA of the polyplex is polyIC, said targeting moiety is HOOC(CH$_2$)$_2$—CH(COOH)—NH—CO—NH—CH(COOH)—(CH$_2$)$_2$—CO— (DUPA residue), and said polymeric conjugate is formula (ii). In a preferred embodiment, said dsRNA of the polyplex is polyIC, said targeting moiety is HOOC(CH$_2$)$_2$—CH(COOH)—NH—CO—NH—CH(COOH)—(CH$_2$)$_2$—CO— (DUPA residue), and said polymeric conjugate is formula (iii). In a preferred embodiment, said dsRNA of the polyplex is polyIC, said targeting moiety is HOOC(CH$_2$)$_2$—CH(COOH)—NH—CO—NH—CH(COOH)—(CH$_2$)$_2$—CO— (DUPA residue), and said polymeric conjugate is formula (iv).

In a preferred embodiment, said dsRNA of the polyplex is polyIC, said LPEI of the polymeric conjugate is covalently linked to one PEG$_{2K}$ moiety (LPEI-PEG 1:1), said linker is the peptide moiety —(NH—(CH$_2$)$_7$—CO)-Phe-Gly-Trp-Trp-Gly-Cys- (SEQ ID NO: 1) and said targeting moiety is HOOC(CH$_2$)$_2$—CH(COOH)—NH—CO—NH—CH(COOH)—(CH$_2$)$_2$—CO— (DUPA residue). In a preferred embodiment, said dsRNA of the polyplex is polyIC, said LPEI of the polymeric conjugate is covalently linked to one PEG$_{2K}$ moiety (LPEI-PEG 1:1), said linker is the peptide moiety —(NH—(CH$_2$)$_7$—CO)-Phe-Phe-(NH—CH$_2$—CH(NH$_2$)—CO)-Asp-Cys- (SEQ ID NO: 2) and said targeting moiety is HOOC(CH$_2$)$_2$—CH(COOH)—NH—CO—NH—CH(COOH)—(CH$_2$)$_2$—CO— (DUPA residue).

In a preferred embodiment, said dsRNA of the polyplex is polyIC, said LPEI of the polymeric conjugate is covalently linked to three PEG$_{2K}$ moieties (LPEI-PEG 1:3), said linker is the peptide moiety —(NH—(CH$_2$)$_7$—CO)-Phe-Gly-Trp-Trp-Gly-Cys- (SEQ ID NO: 1) and said targeting moiety is HOOC(CH$_2$)$_2$—CH(COOH)—NH—CO—NH—CH(COOH)—(CH$_2$)$_2$—CO— (DUPA residue). In a preferred embodiment, said dsRNA of the polyplex is polyIC, said LPEI of the polymeric conjugate is covalently linked to three PEG$_{2K}$ moiety (LPEI-PEG 1:3), said linker is the peptide moiety —(NH—(CH$_2$)$_7$—CO)-Phe-Phe-(NH—CH$_2$—CH(NH$_2$)—CO)-Asp-Cys- (SEQ ID NO: 2) and said targeting moiety is HOOC(CH$_2$)$_2$—CH(COOH)—NH—CO—NH—CH(COOH)—(CH$_2$)$_2$—CO— (DUPA residue). In a preferred embodiment, said dsRNA of the polyplex is polyIC, said LPEI of the polymeric conjugate is LPEI$_{22k}$ and is covalently linked to one PEG moiety (LPEI-PEG 1:1), said linker is the peptide moiety —(NH—(CH$_2$)$_7$—CO)-Phe-Gly-Trp-Trp-Gly-Cys- (SEQ ID NO: 1) and said targeting moiety is HOOC(CH$_2$)$_2$—CH(COOH)—NH—CO—NH—CH(COOH)—(CH$_2$)$_2$—CO— (DUPA residue). In a preferred embodiment, said dsRNA of the polyplex is polyIC, said LPEI of the polymeric conjugate is LPEI$_{22k}$ and is covalently linked to one PEG moiety (LPEI-PEG 1:1), said linker is the peptide moiety —(NH—(CH$_2$)$_7$—CO)-Phe-Phe-(NH—CH$_2$—CH(NH$_2$)—CO)-Asp-Cys- (SEQ ID NO: 2) and said targeting moiety is HOOC(CH$_2$)$_2$—CH(COOH)—NH—CO—NH—CH(COOH)—(CH$_2$)$_2$—CO— (DUPA residue).

In a preferred embodiment, said dsRNA of the polyplex is polyIC, said LPEI of the polymeric conjugate is LPEI$_{22k}$ and is covalently linked to three PEG moiety (LPEI-PEG 1:3), said linker is the peptide moiety —(NH—(CH$_2$)$_7$—CO)-Phe-Gly-Trp-Trp-Gly-Cys- (SEQ ID NO: 1) and said targeting moiety is HOOC(CH$_2$)$_2$—CH(COOH)—NH—CO—NH—CH(COOH)—(CH$_2$)$_2$—CO— (DUPA residue). In a preferred embodiment, said dsRNA of the polyplex is polyIC, said LPEI of the polymeric conjugate is LPEI$_{22k}$ and is covalently linked to three PEG moiety (LPEI-PEG 1:3), said linker is the peptide moiety —(NH—(CH$_2$)$_7$—CO)-Phe-Phe-(NH—CH$_2$—CH(NH$_2$)—CO)-Asp-Cys- (SEQ ID NO: 2) and said targeting moiety is HOOC(CH$_2$)$_2$—CH(COOH)—NH—CO—NH—CH(COOH)—(CH$_2$)$_2$—CO— (DUPA residue).

In a preferred embodiment, said dsRNA of the polyplex is polyIC, said LPEI of the polymeric conjugate is LPEI$_{22k}$ and is covalently linked to one PEG$_{2K}$ moiety (LPEI-PEG 1:1), said linker is the peptide moiety —(NH—(CH$_2$)$_7$—CO)-Phe-Gly-Trp-Trp-Gly-Cys- (SEQ ID NO: 1) and said targeting moiety is HOOC(CH$_2$)$_2$—CH(COOH)—NH—CO—NH—CH(COOH)—(CH$_2$)$_2$—CO— (DUPA residue). In a preferred embodiment, said dsRNA of the polyplex is polyIC, said LPEI of the polymeric conjugate is LPEI$_{22k}$ and is covalently linked to one PEG$_{2K}$ moiety (LPEI-PEG 1:1), said linker is the peptide moiety —(NH—(CH$_2$)$_7$—CO)-Phe-Phe-(NH—CH$_2$—CH(NH$_2$)—CO)-Asp-Cys- (SEQ ID NO: 2) and said targeting moiety is HOOC(CH$_2$)$_2$—CH(COOH)—NH—CO—NH—CH(COOH)—(CH$_2$)$_2$—CO— (DUPA residue).

In a preferred embodiment, said dsRNA of the polyplex is polyIC, said LPEI of the polymeric conjugate is LPEI$_{22k}$ and is covalently linked to three PEG$_{2K}$ moieties (LPEI-PEG 1:3), said linker is the peptide moiety —(NH—(CH$_2$)$_7$—CO)-Phe-Gly-Trp-Trp-Gly-Cys- (SEQ ID NO: 1) and said targeting moiety is HOOC(CH$_2$)$_2$—CH(COOH)—NH—CO—NH—CH(COOH)—(CH$_2$)$_2$—CO— (DUPA residue). In a preferred embodiment, said dsRNA of the polyplex is polyIC, said LPEI of the polymeric conjugate is LPEI$_{22k}$ and is covalently linked to three PEG$_{2K}$ moiety (LPEI-PEG 1:3), said linker is the peptide moiety —(NH—(CH$_2$)$_7$—CO)-Phe-Phe-(NH—CH$_2$—CH(NH$_2$)—CO)-Asp-Cys- (SEQ ID NO: 2) and said targeting moiety is HOOC(CH$_2$)$_2$—CH(COOH)—NH—CO—NH—CH(COOH)—(CH$_2$)$_2$—CO— (DUPA residue).

In a preferred embodiment, said CRPC is metastatic CRPC. In a preferred embodiment, said dsRNA of the polyplex is polyIC, said LPEI of the polymeric conjugate is covalently linked to three PEG moiety (LPEI-PEG 1:3), said linker is the peptide moiety —(NH—(CH$_2$)$_7$—CO)-Phe-Gly-Trp-Trp-Gly-Cys- (SEQ ID NO: 1), said targeting moiety is HOOC(CH$_2$)$_2$—CH(COOH)—NH—CO—NH—CH(COOH)—(CH$_2$)$_2$—CO— (DUPA residue), and said CRPC is metastatic CRPC. In a preferred embodiment, said dsRNA of the polyplex is polyIC, said LPEI of the polymeric conjugate is covalently linked to three PEG moiety (LPEI-PEG 1:3), said linker is the peptide moiety —(NH—(CH$_2$)$_7$—CO)-Phe-Phe-(NH—CH$_2$—CH(NH$_2$)—CO)-Asp-Cys-(SEQ ID NO: 2), said targeting moiety is HOOC(CH$_2$)$_2$—CH(COOH)—NH—CO—NH—CH(COOH)—(CH$_2$)$_2$—CO— (DUPA residue), and said CRPC is metastatic CRPC.

In a preferred embodiment, said dsRNA of the polyplex is polyIC, said LPEI of the polymeric conjugate is LPEI$_{22k}$ and is covalently linked to three PEG moiety (LPEI-PEG 1:3), said linker is the peptide moiety —(NH—(CH$_2$)$_7$—CO)-Phe-Gly-Trp-Trp-Gly-Cys- (SEQ ID NO: 1) and said targeting moiety is HOOC(CH$_2$)$_2$—CH(COOH)—NH—CO—NH—CH(COOH)—(CH$_2$)$_2$—CO— (DUPA residue), and said CRPC is metastatic CRPC. In a preferred embodiment, said dsRNA of the polyplex is polyIC, said LPEI of the polymeric conjugate is LPEI$_{22k}$ and is covalently linked to three PEG moiety (LPEI-PEG 1:3), said linker is the peptide moiety —(NH—(CH$_2$)$_7$—CO)-Phe-Phe-(NH—CH$_2$—CH(NH$_2$)—CO)-Asp-Cys- (SEQ ID NO: 2), said targeting moiety is HOOC(CH$_2$)$_2$—CH(COOH)—NH—CO—NH—CH(COOH)—(CH$_2$)$_2$—CO— (DUPA residue), and said CRPC is metastatic CRPC.

In a preferred embodiment, said dsRNA of the polyplex is polyIC, said LPEI of the polymeric conjugate is LPEI$_{22k}$ and is covalently linked to one PEG$_{2K}$ moiety (LPEI-PEG 1:1), said linker is the peptide moiety —(NH—(CH$_2$)$_7$—CO)-Phe-Gly-Trp-Trp-Gly-Cys- (SEQ ID NO: 1), said targeting moiety is HOOC(CH$_2$)$_2$—CH(COOH)—NH—CO—NH—CH(COOH)—(CH$_2$)$_2$—CO— (DUPA residue), and said CRPC is metastatic CRPC. In a preferred embodiment, said dsRNA of the polyplex is polyIC, said LPEI of the polymeric conjugate is LPEI$_{22k}$ and is covalently linked to one PEG$_{2K}$ moiety (LPEI-PEG 1:1), said linker is the peptide moiety —(NH—(CH$_2$)$_7$—CO)-Phe-Phe-(NH—CH$_2$—CH(NH$_2$)—CO)-Asp-Cys- (SEQ ID NO: 2) and said targeting moiety is HOOC(CH$_2$)$_2$—CH(COOH)—NH—CO—NH—CH(COOH)—(CH$_2$)$_2$—CO— (DUPA residue), and said CRPC is metastatic CRPC.

In a preferred embodiment, said dsRNA of the polyplex is polyIC, said LPEI of the polymeric conjugate is LPEI$_{22k}$ and is covalently linked to three PEG$_{2K}$ moieties (LPEI-PEG 1:3), said linker is the peptide moiety —(NH—(CH$_2$)$_7$—CO)-Phe-Gly-Trp-Trp-Gly-Cys- (SEQ ID NO: 1), said targeting moiety is HOOC(CH$_2$)$_2$—CH(COOH)—NH—CO—NH—CH(COOH)—(CH$_2$)$_2$—CO— (DUPA residue), and said CRPC is metastatic CRPC. In a preferred embodiment, said dsRNA of the polyplex is polyIC, said LPEI of the polymeric conjugate is LPEI$_{22k}$ and is covalently linked to three PEG$_{2K}$ moiety (LPEI-PEG 1:3), said linker is the peptide moiety —(NH—(CH$_2$)$_7$—CO)-Phe-Phe-(NH—CH$_2$—CH(NH$_2$)—CO)-Asp-Cys- (SEQ ID NO: 2), said targeting moiety is HOOC(CH$_2$)$_2$—CH(COOH)—NH—CO—NH—CH(COOH)—(CH$_2$)$_2$—CO— (DUPA residue), and said CRPC is metastatic CRPC.

In a preferred embodiment, the polyplex for use according to the invention is used in combination with immune cells. Preferably, said immune cells are, tumor-infiltrating T-cells (T-TILs), tumor specific engineered T-cells or peripheral blood mononuclear cells (PBMCs). Preferably, said immune cells are tumor-infiltrating T-cells (T-TILs) or tumor specific engineered T-cells. In a more preferred embodiment, said immune cells are peripheral blood mononuclear cells (PBMCs). In a more preferred embodiment, said immune cells are tumor-infiltrating T-cells (T-TILs). In a more preferred embodiment, said immune cells are tumor specific engineered T-cells.

In a further aspect, the invention relates to a pharmaceutical composition for use in the treatment of castration resistant prostate cancer (CRPC), said pharmaceutical composition comprises a pharmaceutically acceptable carrier and polyplex comprising a double stranded ribonucleic acid (dsRNA) and a polymeric conjugate, wherein said polymeric conjugate consists of a linear polyethyleneimine (LPEI), one or more polyethylene glycol (PEG) moieties, one or more linkers and one or more targeting moieties, wherein said LPEI is covalently bound to said one or more PEG moieties and each of said one or more PEG moieties is conjugated via one of said one or more linkers to one of said one or more targeting moiety, wherein said targeting moiety is capable of binding to a cancer antigen, and wherein said cancer antigen is prostate surface membrane antigen (PSMA).

In a preferred embodiment, the pharmaceutical composition for use according to the invention further comprises immune cells. Preferably, said immune cells are tumor-infiltrating T-cells (T-TILs), tumor specific engineered T-cells, or peripheral blood mononuclear cells (PBMCs). Preferably, said immune cells are tumor-infiltrating T-cells (T-TILs) or tumor specific engineered T-cells. In a more preferred embodiment, said immune cells are peripheral blood mononuclear cells (PBMCs). In a more preferred embodiment, said immune cells are tumor-infiltrating T-cells (T-TILs). In a more preferred embodiment, said immune cells are tumor specific engineered T-cells.

In a further aspect, the invention relates to a method for treating of castration resistant prostate cancer, said method comprises administering to a patient in need a polyplex comprising a double stranded ribonucleic acid (dsRNA) and a polymeric conjugate, wherein said polymeric conjugate consists of a linear polyethyleneimine (LPEI), one or more polyethylene glycol (PEG) moieties, a linker and a targeting moiety, wherein the LPEI is covalently bound to the one or more PEG moieties and each PEG moiety is conjugated via the linker to the targeting moiety, wherein the targeting moiety is capable of binding to a cancer antigen, and wherein the cancer antigen is prostate surface membrane antigen (PSMA). The term "patient" is used interchangeably and refers to either a human or a non-human animal, preferably to a human.

Methods of administering, e.g. the polyplex or pharmaceutical composition include, but are not limited to, parenteral, e.g., intravenous, intraperitoneal, intramuscular, subcutaneous, mucosal (e.g., oral, intranasal, buccal, vaginal, rectal, intraocular), intrathecal, topical and intradermal routes. Administration can be systemic or local. In a certain embodiment, the pharmaceutical composition is adapted for intra-brain administration. In a preferred embodiment, the polyplex or pharmaceutical composition is administered systemically by injection.

Suitable carriers, modes of administration, dosage forms, etc., are well-known to the skilled person. The term "carrier" refers to a diluent, adjuvant, excipient, or vehicle with which the active agent is administered. The carriers in the pharmaceutical composition may comprise a binder, such as microcrystalline cellulose, polyvinylpyrrolidone (polyvidone or povidone), gum tragacanth, gelatin, starch, lactose or lactose monohydrate; a disintegrating agent, such as alginic acid, maize starch and the like; a lubricant or surfactant, such as magnesium stearate, or sodium lauryl sulphate; and a glidant, such as colloidal silicon dioxide.

The compositions may be formulated for parenteral administration by injection, e.g., by bolus injection or continuous infusion. Formulations for injection may be presented in unit dosage form, e.g., in ampoules or in multidose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen free water, before use.

For administration by inhalation, for example for nasal administration, the compositions according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin, for use in an inhaler or insufflator may be formulated containing a powder mix of the compound and a suitable powder base such as lactose or starch.

In certain embodiments the pharmaceutical composition is formulated for administration by any known method as described above. Particular methods of administration contemplated here are intravenous and intra-brain (intracerebral) administration.

The pharmaceutical composition according to any one of the embodiments defined above may be formulated for intravenous, intra-brain (intracerebral), oral, intradermal, intramuscular, subcutaneous, transdermal, transmucosal, intranasal or intraocular administration.

In a further aspect, the present invention provides a polyplex comprising a double stranded RNA (dsRNA) and a polymeric conjugate, wherein said polymeric conjugate consists of a linear polyethyleneimine (LPEI), three polyethylene glycol (PEG) moieties, three linkers and three targeting moieties, wherein said LPEI is covalently bound to each of said three PEG moieties and each of said three PEG moieties is conjugated via one of said three linkers to one of said three targeting moieties, wherein each of said three targeting moieties is capable of binding to a cancer antigen, wherein said cancer antigen is prostate surface membrane antigen (PSMA), and wherein said polymeric conjugate is formula (d):

(d) [T-(NH—(CH$_2$)$_7$—CO)-Phe-Gly-Trp-Trp-Gly-Cys-PEG (SEQ ID NO: 20)]3-LPEI;

and wherein said T represents said targeting moiety.

In a preferred embodiment of said inventive polyplex, said dsRNA is polyinosinic-polycytidylic acid double stranded RNA (polyIC).

In a preferred embodiment of said inventive polyplex, said polymeric conjugate is (d) [T-(NH—(CH$_2$)$_7$—CO)-Phe-Gly-Trp-Trp-Gly-Cys-PEG (SEQ ID NO: 20)]$_3$-LPEI, wherein said T represent said targeting moiety, and wherein said PEG moiety has a molecular weight of 2 kD. In a preferred embodiment of said inventive polyplex, said polymeric conjugate is (d) [T-(NH—(CH$_2$)$_7$—CO)-Phe-Gly-Trp-Trp-Gly-Cys-PEG (SEQ ID NO: 20)]$_3$-LPEI, wherein said T represent said targeting moiety, and wherein said LPEI has a molecular weight of 22 kD. In a preferred embodiment of said inventive polyplex, said polymeric conjugate is (d) [T-(NH—(CH$_2$)$_7$—CO)-Phe-Gly-Trp-Trp-Gly-Cys-PEG (SEQ ID NO: 20)]$_3$-LPEI, wherein said T represent said targeting moiety, and wherein said PEG moiety has a molecular weight of 2 kD and said LPEI has a molecular weight of 22 kD.

In a preferred embodiment of said inventive polyplex, said polymeric conjugate is (d) [T-(NH—(CH$_2$)$_7$—CO)-Phe-Gly-Trp-Trp-Gly-Cys-PEG (SEQ ID NO: 20)]$_3$-LPEI, wherein said T represent said targeting moiety, and wherein said PEG moiety has a molecular weight of 2 kD and said dsRNA is polyinosinic-polycytidylic acid double stranded RNA (polyIC). In a preferred embodiment of said inventive polyplex, said polymeric conjugate is (d) [T-(NH—(CH$_2$)$_7$—CO)-Phe-Gly-Trp-Trp-Gly-Cys-PEG (SEQ ID NO: 20)]$_3$-LPEI, wherein said T represent said targeting moiety, and wherein said LPEI has a molecular weight of 22 kD and said dsRNA is polyinosinic-polycytidylic acid double stranded RNA (polyIC). In a preferred embodiment of said inventive polyplex, said polymeric conjugate is (d) [T-(NH—(CH$_2$)$_7$—CO)-Phe-Gly-Trp-Trp-Gly-Cys-PEG (SEQ ID NO: 20)]$_3$-LPEI, wherein said T represent said targeting moiety, and wherein said PEG moiety has a molecular weight of 2 kD and said LPEI has a molecular weight of 22 kD and said dsRNA is polyinosinic-polycytidylic acid double stranded RNA (polyIC).

In a preferred embodiment of said inventive polyplex, said polymeric conjugate is formula (d):
(d) [T-(NH—(CH$_2$)$_7$—CO)-Phe-Gly-Trp-Trp-Gly-Cys-PEG (SEQ ID NO: 20)]$_3$-LPEI;
wherein said T represents said targeting moiety, and wherein said PEG moiety is of formula (v)

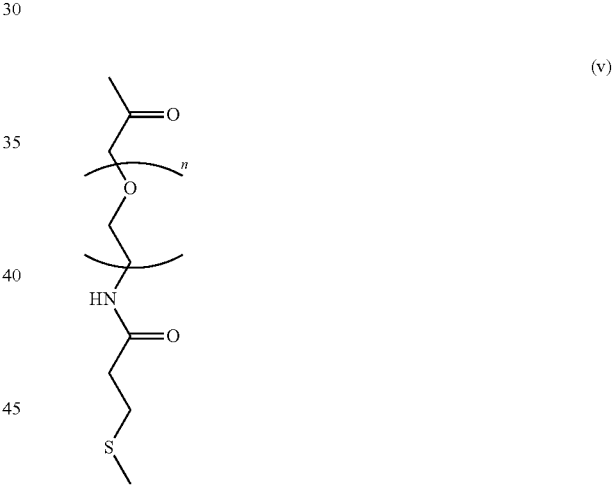

(v)

wherein n is 40-45, and wherein said PEG moiety of formula (v) is linked to the Cys residue of (d) via a disulfide bond.

In a preferred embodiment of the inventive polyplex, said polymeric conjugate is (d) [T-(NH—(CH$_2$)$_7$—CO)-Phe-Gly-Trp-Trp-Gly-Cys-PEG (SEQ ID NO: 20)]$_3$-LPEI, wherein said T represent said targeting moiety, and wherein said PEG moiety is of formula (v), wherein n is 40-45 and said PEG moiety of formula (v) is linked to the Cys residue of (d) via a disulfide bond; and wherein preferably said dsRNA is polyIC.

In a preferred embodiment of said inventive polyplex, said polymeric conjugate is (d) [T-(NH—(CH$_2$)$_7$—CO)-Phe-Gly-Trp-Trp-Gly-Cys-PEG (SEQ ID NO: 20)]$_3$-LPEI$_{22k}$, wherein said T represent said targeting moiety; wherein said PEG moiety is of formula (v), n is 40-45 and said PEG moiety of formula (v) is linked to the Cys residue of (d) via a disulfide bond; and wherein preferably said dsRNA is polyIC.

In a preferred embodiment of said inventive polyplex, said polymeric conjugate is (d) [T-(NH—(CH$_2$)$_7$—CO)-Phe-Gly-Trp-Trp-Gly-Cys-PEG$_{2k}$ (SEQ ID NO: 26)]$_3$-LPEI linked to said targeting moieties, wherein said T represent said targeting moiety; wherein said PEG moiety is of formula (v), n is 40-45 and said PEG moiety of formula (v) is linked to the Cys residue of (d) via a disulfide bond; and wherein preferably said dsRNA is polyIC.

In a preferred embodiment of said inventive polyplex, said polymeric conjugate is (d) [T-(NH—(CH$_2$)$_7$—CO)-Phe-Gly-Trp-Trp-Gly-Cys-PEG$_{2k}$ (SEQ ID NO: 26)]$_3$-LPEI$_{22k}$, wherein said T represent said targeting moiety; wherein said PEG moiety is of formula (v), n is 40-45 and said PEG moiety of formula (v) is linked to the Cys residue of (d) via a disulfide bond; and wherein preferably said dsRNA is polyIC.

In a preferred embodiment of said inventive polyplex, said polymeric conjugate of the polyplex according to the invention is formula (iv)

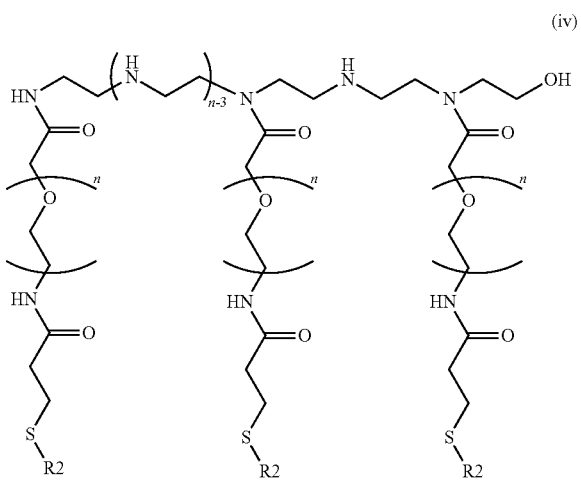

(iv)

wherein R2 is wherein said T represents said targeting moiety; and wherein n is 40-45.

The targeting moiety of the polyplex of the invention may be a native, natural or modified ligand or a paralog thereof, or a non-native ligand such as an antibody, a single-chain variable fragment (scFv), or an antibody mimetic such as an affibody, to any one of the cancer antigens.

In a preferred embodiment of said inventive polyplex, said targeting moiety is HOOC(CH$_2$)$_2$—CH(COOH)—NH—CO—NH—CH(COOH)—(CH$_2$)$_2$—CO— referred herein as DUPA residue.

In a preferred embodiment of said inventive polyplex, said polymeric conjugate is formula (d):

(d)  [T-(NH—(CH$_2$)$_7$—CO)-Phe-Gly-Trp-Trp-Gly-Cys-PEG (SEQ ID NO: 20)]3-LPEI;

and wherein said T represents said targeting moiety HOOC(CH$_2$)$_2$—CH(COOH)—NH—CO—NH—CH(COOH)—(CH$_2$)$_2$—CO— (DUPA residue). In a preferred embodiment, said polymeric conjugate is said formula (d), wherein said T represents said targeting moiety HOOC(CH$_2$)$_2$—CH(COOH)—NH—CO—NH—CH(COOH)—(CH$_2$)$_2$—CO— (DUPA residue), and said dsRNA is polyIC.

In a more preferred embodiment of said inventive polyplex, said targeting moiety is HOOC(CH$_2$)$_2$—CH(COOH)—NH—CO—NH—CH(COOH)—(CH$_2$)$_2$—CO— (DUPA residue), and said polymeric conjugate has formula (iv). In another preferred embodiment, said dsRNA is polyIC, said targeting moiety is HOOC(CH$_2$)$_2$—CH(COOH)—NH—CO—NH—CH(COOH)—(CH$_2$)$_2$—CO— (DUPA residue), and said polymeric conjugate is formula (iv).

In a preferred embodiment of said inventive polyplex, said polymeric conjugate is (d) [T-(NH—(CH$_2$)$_7$—CO)-Phe-Gly-Trp-Trp-Gly-Cys-PEG (SEQ ID NO: 20)]$_3$-LPEI, wherein said T represent the targeting moiety DUPA residue, and wherein said PEG moiety has a molecular weight of 2 kD. In a preferred embodiment, said polymeric conjugate is (d) [T-(NH—(CH$_2$)$_7$—CO)-Phe-Gly-Trp-Trp-Gly-Cys-PEG (SEQ ID NO: 20)]$_3$-LPEI, wherein said T represent the targeting moiety DUPA residue, and wherein said LPEI has a molecular weight of 22 kD. In a preferred embodiment, said polymeric conjugate is (d) [T-(NH—(CH$_2$)$_7$—CO)-Phe-Gly-Trp-Trp-Gly-Cys-PEG (SEQ ID NO: 20)]$_3$-LPEI, (SEQ ID NO: 30)

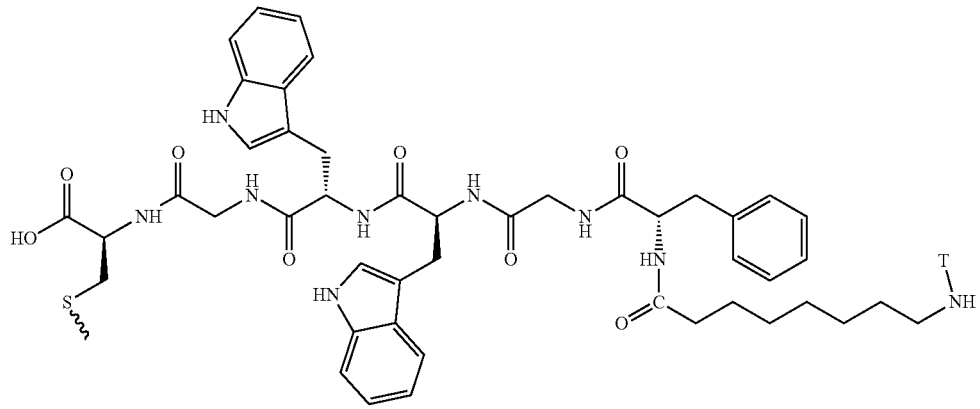

wherein said T represent the targeting moiety DUPA residue, and wherein said PEG moiety has a molecular weight of 2 kD and said LPEI has a molecular weight of 22 kD.

In a preferred embodiment of said inventive polyplex, said polymeric conjugate is (d) [T-(NH—(CH$_2$)$_7$—CO)-Phe-Gly-Trp-Trp-Gly-Cys-PEG (SEQ ID NO: 20)]$_3$-LPEI, wherein said T represent the targeting moiety DUPA residue, and wherein said PEG moiety has a molecular weight of 2 kD and said dsRNA is polyinosinic-polycytidylic acid double stranded RNA (polyIC). In a preferred embodiment of said inventive polyplex, said polymeric conjugate is (d) [T-(NH—(CH$_2$)$_7$—CO)-Phe-Gly-Trp-Trp-Gly-Cys-PEG (SEQ ID NO: 20)]$_3$-LPEI, wherein said T represent the targeting moiety DUPA residue, and wherein said LPEI has a molecular weight of 22 kD and said dsRNA is polyinosinic-polycytidylic acid double stranded RNA (polyIC). In a preferred embodiment of said inventive polyplex, said polymeric conjugate is (d) [T-(NH—(CH$_2$)$_7$—CO)-Phe-Gly-Trp-Trp-Gly-Cys-PEG (SEQ ID NO: 20)]$_3$-LPEI, wherein said T represent the targeting moiety DUPA residue, and wherein said PEG moiety has a molecular weight of 2 kD and said LPEI has a molecular weight of 22 kD and said dsRNA is polyinosinic-polycytidylic acid double stranded RNA (polyIC).

In a preferred embodiment of said inventive polyplex, said polymeric conjugate is (d) [T-(NH—(CH$_2$)$_7$—CO)-Phe-Gly-Trp-Trp-Gly-Cys-PEG (SEQ ID NO: 20)]$_3$-LPEI, wherein said T represent the targeting moiety DUPA residue, and wherein said PEG moiety is of formula (v), wherein n is 40-45 and said PEG moiety of formula (v) is linked to the Cys residue of (d) via a disulfide bond; and wherein preferably said dsRNA is polyIC.

In a preferred embodiment of said inventive polyplex, said polymeric conjugate is (d) [T-(NH—(CH$_2$)$_7$—CO)-Phe-Gly-Trp-Trp-Gly-Cys-PEG (SEQ ID NO: 20)]3-LPEI$_{22k}$, wherein said T represent the targeting moiety DUPA residue; wherein said PEG moiety is of formula (v), n is 40-45 and said PEG moiety of formula (v) is linked to the Cys of (d) residue via a disulfide bond; and wherein preferably said dsRNA is polyIC.

In a preferred embodiment of said inventive polyplex, said polymeric conjugate is (d) [T-(NH—(CH$_2$)$_7$—CO)-Phe-Gly-Trp-Trp-Gly-Cys-PEG$_{2k}$ (SEQ ID NO: 26)]$_3$-LPEI linked to said targeting moieties, wherein said T represent the targeting moiety DUPA residue; wherein said PEG moiety is of formula (v), n is 40-45 and said PEG moiety of formula (v) is linked to the Cys residue of (d) via a disulfide bond; and wherein preferably said dsRNA is polyIC.

In a preferred embodiment of said inventive polyplex, said polymeric conjugate is (d) [T-(NH—(CH$_2$)$_7$—CO)-Phe-Gly-Trp-Trp-Gly-Cys-PEG$_{2k}$ (SEQ ID NO: 26)]$_3$-LPEI$_{22k}$, wherein said T represent the targeting moiety DUPA residue; wherein said PEG moiety is of formula (v), n is 40-45 and said PEG moiety of formula (v) is linked to the Cys residue of (d) via a disulfide bond; and wherein preferably said dsRNA is polyIC.

In a preferred embodiment of said inventive polyplex, said polymeric conjugate has formula (d):

(d) [T-(NH—(CH$_2$)$_7$—CO)-Phe-Gly-Trp-Trp-Gly-Cys-PEG (SEQ ID NO: 20)]3-LPEI;

wherein said T represents the targeting moiety DUPA residue, and wherein said PEG moiety is of formula (v)

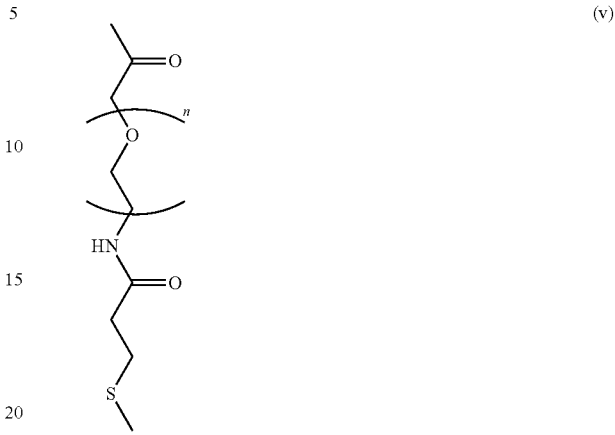

wherein n is 40-45, and wherein said PEG moiety of formula (v) is linked to the Cys residue of (d) via a disulfide bond.

In a preferred embodiment of said inventive polyplex, said polymeric conjugate is (d) [T-(NH—(CH$_2$)$_7$—CO)-Phe-Gly-Trp-Trp-Gly-Cys-PEG]$_3$-LPEI, wherein said T represent the targeting moiety DUPA residue, and wherein said PEG moiety is of formula (v), wherein n is 40-45 and said PEG moiety of formula (v) is linked to the Cys residue of (d) via a disulfide bond; and wherein preferably said dsRNA is polyIC.

In a preferred embodiment of said inventive polyplex, said polymeric conjugate is (d) [T-(NH—(CH$_2$)$_7$—CO)-Phe-Gly-Trp-Trp-Gly-Cys-PEG (SEQ ID NO: 20)]$_3$-LPEI$_{22k}$, wherein said T represent the targeting moiety DUPA residue; wherein said PEG moiety is of formula (v), n is 40-45 and said PEG moiety of formula (v) is linked to the Cys residue of (d) via a disulfide bond; and wherein preferably said dsRNA is polyIC.

In a preferred embodiment of said inventive polyplex, said polymeric conjugate is (d) [T-(NH—(CH$_2$)$_7$—CO)-Phe-Gly-Trp-Trp-Gly-Cys-PEG$_{2k}$ (SEQ ID NO: 26)]$_3$-LPEI linked to said targeting moieties, wherein said T represent the targeting moiety DUPA residue; wherein said PEG moiety is of formula (v), n is 40-45 and said PEG moiety of formula (v) is linked to the Cys residue of (d) via a disulfide bond; and wherein preferably said dsRNA is polyIC.

In a preferred embodiment of said inventive polyplex, said polymeric conjugate is (d) [T-(NH—(CH$_2$)$_7$—CO)-Phe-Gly-Trp-Trp-Gly-Cys-PEG$_{2k}$ (SEQ ID NO: 26)]$_3$-LPEI$_{22k}$, wherein said T the targeting moiety DUPA residue; wherein said PEG moiety is of formula (v), n is 40-45 and said PEG moiety of formula (v) is linked to the Cys residue of (d) via a disulfide bond; and wherein preferably said dsRNA is polyIC.

The invention will now be illustrated by the following non-limiting Examples.

EXAMPLES

Example 1—Preparation of the Polyplex

Chemicals for Synthesis of LPEI and PEGylation

NHS-PEG-OPSS (ortho-pyridyldisulfide-poly-ethyene glycol-N-hydroxylsuccinimide ester), also named PDP-PEG-NHS (PDP: pyridyl dithio propionate), with molecular weight of ~2 kDa, was purchased from Creative PEGworks (Winston, USA). Poly(2-ethyl-2-oxazoline), average molecular weight (Mn) ~50 kDa, and anhydrous dimethyl sulfoxide (DMSO) were purchased from Sigma-Aldrich (Israel). Absolute ethanol was purchased from Romical (Israel). All solvents were used without further purification.

Synthesis of LPEI (Free Base Form)

Synthesis of LPEI and PEGylation of LPEI was carried out as previously described (WO 2015/173824; Joubran, et al., 2014, Optimization of liganded polyethylenimine polyethylene glycol vector for nucleic acid delivery, Bioconjug Chem 2014, 25(9):1644-1654).

In brief, 8.0 g (0.16 mmol) of poly(2-ethyl-2-oxazoline) were hydrolyzed with 100 mL of concentrated HCl (37%) and refluxed for 48 h, yielding a white precipitate. The solid was filtered by vacuum through as inter glass and washed several times with water. The resulting LPEI hydrochloride salt was air-dried overnight, dissolved in 50 mL of water, and freeze-dried (5 g, 78%, $^1$H-NMR, D20, 400 MHz: singlet 3.5 ppm). The resulting LPEI salt (4.5 g) was made alkaline by adding aqueous NaOH (3 M) and the resulting white precipitate was filtered and washed with water until neutral. The solid was then dissolved in water and further lyophilized to give a white solid (2 g, 81%).

Synthesis of LPEI-PEG$_{2k}$-OPSS Diconjugates (Diconjugate 1:1 and 1:3)

To generate differentially PEGylated copolymers, the secondary amines on LPEI were conjugated to the terminal NHS ester orthogonal protecting group on PEG. The N-hydroxysuccinimide (NHS) ester is spontaneously reactive with the secondary backbone amines of LPEI, providing efficient PEGylation of LPEI. Furthermore, the reaction of the NHS-PEG-OPSS with the amines of PEI results in formation of stable, irreversible amide bonds.

174 mg (8 µmol) of LPEI were dissolved in 2.7 mL of absolute EtOH and agitated at room temperature for 15 min. A 5-fold molar excess of OPPS-PEG$_{2k}$-CONHS (79 mg, 39.5 µmol) was dissolved in 500 µL of anhydrous DMSO and introduced in small portions into the LPEI mixture. The reaction mix was agitated at ~800 rpm on a vortex stirrer at ambient temperature for 3 h. Different PEG-substituted LPEIs were separated by cation-exchange chromatography, using anHR10/10 column filled with MacroPrep High S resin (BioRad). The purity of the eluted fractions of the diconjugates was assessed using reverse phase HPLC equipped with analytical Vydac C-8 monomeric 5 µm column (300 Å, 4.6×150 mm), using a linear gradient of 5-95% acetonitrile over 25 min at 1 mL/min flow. Fractions with 95% purity or higher were combined. The combined fractions were further dialyzed against 20 mM HEPES pH 7.4. The ratio of PEG$_{2k}$ groups conjugated to LPEI in the diconjugates was determined by $^1$H NMR. The integral values of the hydrogens from the PEG —(CH$_2$—CH$_2$—O)— and from the LPEI —(CH$_2$—CH$_2$—NH)— were used to determine the ratio between the two conjugated copolymers. Of the various products obtained from the cation-exchange, two products, LPEI-PEG$_{2k}$-OPSS (diconjugate 1:1, with molar ration of LPEI to PEG ~1:1) and LPEI-(PEG$_{2k}$)$_3$-(OPSS)$_3$ (diconjugate 1:3, with molar ratio of ~1:3), were chosen for the generation of triconjugates. A copper assay was used to evaluate the copolymer concentration. Briefly, the copolymers were incubated with CuSO4 (23 mg dissolved in100 mL of acetate buffer) for 20 min and their absorbance at 285 nm was measured.

Synthesis of the DUPA-peptide Linker

Preparation of the DUPA moiety: The DUPA moiety was synthesized according to Kularatne S A, et al. (2009) (Design, synthesis, and preclinical evaluation of prostate-specific membrane antigen targeted (99m)Tc-radioimaging agents. Mol Pharm 6(3):790-800). Synthesis of the peptide linker: Fmoc-Cys(trt)-wang resin (commercially available) was used as solid support, and the peptide was synthesized via standard Fmoc SPPS procedures (loading 0.47 mmol/gm; scale of the synthesis 0.25 mmol). The Fmoc-Cys(trt)-wang resin was swollen in dichloromethane (DCM) for 2 h and in dimethylformamide (DMF) for 20 minutes. Removal of Fmoc: In order to remove Fmoc, the Fmoc-peptidyl-resin was incubated twice with 20% piperidine in DMF (10 mL) (10 min and 15 min at RT). Using the Kaiser Test, complete removal of Fmoc was verified, before rinsing the solid support with DMF (5×5 mL). Coupling of amino acids to the peptide linker: 5 equivalents of Fmoc-protected amino acid, 4.5 equivalents HATU and 8 equivalents DIPEA were dissolved in DMF (6 mL). The reaction mixture was activated for 5 min at 0° C. and then added to the peptide resin with free amine. The resin was mixed for ca. 45 min. Then the solid support was rinsed with DMF (4×5 mL). For verifying that coupling was completed, Kaiser Test was used again. Capping via acetic anhydride: For blocking the unreacted free amine functional group, the resin was incubated with acetic anhydride after the first amino acid coupling. The resin was treated with a solution of acetic anhydride (10 equivalents) and DIPEA (8 equivalents) in DMF for 20 min and rinsed with DMF (5×5 mL) and DCM (3×5 mL). Coupling of the DUPA moiety to the peptide linker: The fully protected DUPA moiety with free acid (5 equivalents), HATU (4.5 equivalents) and DIPEA (8 equivalents) were dissolved in DMF (6 mL). The combined reaction mixture was activated for 5 min at 0° C. The pre-activated DUPA moiety was then admixed to the peptide resin bearing N-terminal free amine. The solution was mixed for about 60 min and rinsed with DMF (5×5 mL). Coupling of the DUPA moiety was verified by the Kaiser Test. Release of the DUPA-peptide linker from the resin: A freshly prepared solution (5 mL) of trifluoroacetic acid (TFA)/triisopropylsilane (TIS)/TDW (95:2.5:2.5) was cooled to 0° C. and then added to 200 mg resin-bound peptide-DUPA. The solution was mixed at RT for 4 h, filtered and rinsed with 3 mL concentrated TFA. The resulting DUPA-peptide linker was precipitated by slowly admixing cold ether to the solution, which was then centrifuged and rinsed twice with cold ether. A minimal volume of a 1:1 ACN/TDW solution was used to dissolve the crude DUPA-peptide linker, which was then lyophilized and finally purified by RP-HPLC. The formation of the DUPA-peptide linker was verified by LC-MS. Dylight680 conjugation was carried out using the reported procedure (Kelderhouse et al., Development of tumor-targeted near infrared probes for fluorescence guided surgery, Bioconjug Chem 2013, 24(6): 1075-1080).

Synthesis of PEI-PEG-DUPA (PPD)

4.37 mg (1.2×10-4 mmol) PEI-PEG (1:1) were dissolved in 940 µl of 20 mM HEPES (pH 7.4). 1 mg (9.1×10-4 mmol, about 5 equivalents) of the DUPA-peptide linker was dissolved in 2 ml of 1:1 ACN (HPLC grade)/(20 mM HEPES, pH 7.4) and added dropwise to the PEI-PEG solution. 4 mL of 20 mM HEPES pH 7.4 were added to the solution for achieving a total concentration of ~10% ACN. The further reaction was carried out as described by Joubran et al., 2014 (op. cit.).

Formation of PPD/polyIC complex

PPD was complexed with polyIC (low molecular weight (LMW) polyIC for example by InvivoGen) at a nitrogen (from PPD)/phosphate (from polyIC) ratio (N/P ratio) of 8. LMW is from 0.2 kb to 1 kb. For in vivo experiments, HBG buffer (20 mM HEPES, pH 7.4, 5% glucose, w/v) was used. For in vitro experiments, HBS buffer (20 mM HEPES, 150 mM NaCl, pH 7.4) was used. PPD was added to and incubated with polyIC for 45 minutes at RT. The size of the PPD/polyIC complex was measured by dynamic light scattering as described in Joubran, et al., 2014 (op. cit.). Complex size was found to be 105±16.7 nm.

Example 2—Assays

Confocal Microscopy

Using DUPA-peptide linker-Dylight 680, selectivity of DUPA moiety for PSMA-overexpressing cells was verified. Uptake of DUPA-linker-Dylight 680 was monitored using confocal fluorescence microscopy (FLUOVIEW FV-1000, Olympus, Japan). First, cells were seeded (8000 cells/well) in 8-well µ-slides (Ibidi, cat no 80826) and grown for 72 h. Then, the fresh medium with the DUPA-peptide linker-Dylight 680 (70 nM) and sulforhodamine (green) was added. Cells were monitored by time-lapse microscopy for 5 h.

Cell Survival

PC3-PSMA, LNCaP, VCaP, MCF7 and PC3 cells were seeded (96-well plates, 5000 cells/well, in triplicate) and grown for one day and then incubated with PPD/polyIC, PPD/polyI, or polyIC alone. After incubation, cell survival was quantified (CellTiter-Glo Luminescent Cell Viability Assay, Promega).

Western Blot Analysis

LNCaP cells (6-well plates, $1 \times 10^6$ cells/well) were seeded and grown for one day and then incubated with PPD/polyIC as indicated, lysed with steaming hot Laemmli sample buffer and analyzed by western blot for investigation of cleavage activity of caspase-3 and PARP using primary antibodies anti-caspase3 (Cell Signaling Technology, cat #96625), anti-cleaved caspase-3 (Cell Signaling Technology, cat #96615) and anti-PARP (Cell Signaling Technology, cat #95425). Anti-GAPDH was used to normalize caspase-3 and PARP expression levels to GAPDH expression (Santa Cruz, sc-25778).

Quantification of IP-10 and RANTES Cytokines by ELISA

PC3-PSMA and LNCaP cells were seeded (96-well plates, triplicates, PC3-PSMA: 2,000 cells/well, LNCaP: 10,000 cells/well for) and grown for one day and then incubated with PPD/polyIC. After 48 h or 72 h, samples were taken from the medium, and secreted cytokine concentrations of IP-10 and RANTES were detected via ELISA (PeproTech).

Quantification of IFN-β, IFN-γ, IL-2 and TNF-α by qRT-PCR

Total RNA extraction from PC3-PSMA and LNCaP cells: PC3-PSMA (100,000 cells/well) and LNCaP cells (500,000 cells/well) were seeded and grown for one day and then incubated with PPD/polyIC. After 4 or 8 h total RNA was isolated (EZ-10 DNA Away RNA-Miniprep Kit, Bio Basic). Total RNA Extraction from stimulated PBMCs: LNCaP cells were seeded ($1 \times 10^6$ cells/well, poly-lysine pre-coated 6-well plates) and grown for one day and then incubated with PPD/polyIC. After 48 h, samples from the conditioned medium were used for seeding (6-well plates, $1 \times 10^7$ cells/well) and growing freshly isolated PBMCs, which were incubated for 24 h. Then total RNA was isolated from the PBMCs (EZ-10 DNA Away RNA-Miniprep Kit, Bio Basic).

The RNA was reversely transcribed (High Capacity cDNA Reverse Transcription Kit, Applied Biosystems), and qRT-PCR was carried out (Fast SYBR Green, Applied Biosystems) using the primers as listed in Tab. 1. Relative quantities of cytokine transcripts were normalized to GAPDH or HUPO transcripts and compared to untreated cells (AA CT method).

TABLE 1 qRT-PCR primer sequences

| Gene | SEQ ID NO: | Primer sequences (from 5' to 3') |
|---|---|---|
| IFN-β | 5 | F: ATGACCAACAAGTGTCTCCTCC |
|  | 6 | R: GCTCATGGAAAGAGCTGTAGTG |
| GAPDH | 7 | F: GAGCCACATCGCTCAGAC |
|  | 8 | R: CTTCTCATGGTTCACACCC |
| IFN-γ | 9 | F: GCTGTTACTGCCAGGACCCATA |
|  | 10 | R: TCCGCTACATCTGAATGACCTG |
| IL-2 | 11 | F: AGACCCAGGGACTTAATCAGCAA |
|  | 12 | R: CAATGGTTGCTGTCTCATCAG |
| TNF-α | 13 | F: GTGCTTGTTCCTCAGCCTCTTC |
|  | 14 | R: GGCCAGAGGGCTGATTAGAGAG |
| HUPO | 15 | F: GCTTCCTGGAGGGTGTCC |
|  | 16 | R: GGACTCGTTTGTACCCGTTG |

Chemotaxis Assay

LNCaP cells were seeded (poly-lysine pre-coated 24-well plates, density 250,000 cells/well) and grown for one day. Culture medium was exchanged with fresh medium including only 0.15% FBS, and cells were then incubated with PPD/polyIC. After 48 h, samples from the conditioned medium were tested for their capability to stimulate chemotaxis of PBMCs (Transwell plates, microporous polycarbonate membrane, 0.5 µm, Corning, Costar). In detail, conditioned medium was pipetted to the lower wells of the Transwell plate (medium supplemented with only 0.15% FBS) and freshly isolated PBMCs were seeded ($1 \times 10^6$ cell in 100 µl medium/well) in the upper Transwell inserts of each well. After incubation of 4 h at 37° C., medium with migrated PBMCs were analyzed via FACS, scatter-gating to enumerate the lymphocyte subsets. The results are presented as ratio of the number of PBMCs that migrated towards the conditioned medium from the treated cells to the number of PBMCs that migrated towards fresh growth medium.

Example 3—In Vitro and In Vivo Tests

In Vitro Analysis of Bystander Effects Induced by PPD/polyIC Treatment

Co-culture systems were used to analyze PPD/polyIC bystander effects in vitro. Treated PSMA-overexpressing cells were co-cultured with PBMCs alone or with PBMCs and cells not expressing PSMA that are to represent neighboring cancer cells. The bystander effects were evaluated via cell lines that stably express luciferase (LNCaP-Luc/GFP, PC3-Luc/GFP or MCF7-Luc/GFP). Survival of these cells was measured (luciferase activity)(Luciferase Assay System, Promega).

Co-culture system of LNCaP-Luc/GFP-PBMC: LNCaP-Luc/GFP cells were seeded (10,000 cells/well, 96-well plates pre-coated with poly-lysine, triplicate), grown for one day and incubated with PPD/polyIC. After 24 h, freshly isolated PBMCs ($1 \times 10^5$ cells per well) were added to the culture, and survival of the LNCaP-Luc/GFP cells was detected after 24 h (luciferase activity).

Co-culture system of LNCaP-PBMC-PC3-Luc/GFP: LNCaP cells (6,000 cells/well) were seeded (96-well plates, pre-coated with poly-lysine, triplicate), grown for one day and incubated with PPD/polyIC. After 16 h, PC3-Luc/GFP cells (4,000 cells/well) and after further 6 h, freshly isolated PBMCs ($1\times10^5$ per well) were each added to the culture. After 48 h, survival of PC3-Luc/GFP cells was measured (luciferase activity)

Co-culture system of PC3-PSMA-PBMC-MCF7-Luc/GFP: PC3-PSMA cells (2,000 cells/well) were seeded (96-well plates, pre-coated with poly-lysine, triplicate) grown for one day and incubated with PPD/polyIC. After 16 h, MCF7-Luc/GFP cells (4,000 cells/well) and after further 6 h freshly isolated PBMCs were added to the culture ($1\times10^5$ cells per well). After 48 h, survival of the MCF7-Luc/GFP cells was measured (luciferase activity).

Androgen-Resistant Prostate Cancer Xenograft Model with Reconstituted Immune System Androgen-resistant (androgen-independent) prostate cancer cells, PC3-PSMA ($4.6\times10^6$) were injected subcutaneously to NOD-SCID male mice (Harlan Laboratories, Inc.). After 14 days, when the tumors reached 100 mm$^3$, mice were randomly split into four groups (7 mice/group) and two groups were treated with intravenous injections of PPD/polyIC (0.25 mg/kg, N/P ratio 8), while the other two groups are untreated controls. Each in one treated and one untreated group, an immune system was partially reconstituted (intravenous injection of $4\times10^6$ human PBMCs on days 3 and 8). Calculation of tumor volumes: tumor width W2×tumor length L/2.

Example 4—Results of the In Vitro Tests

Specific Binding and Uptake of DUPA Coupled to Dylight680 Via a Specific Peptide Linker into PSMA-Overexpressing Cells This example demonstrated that the PSMA ligand DUPA coupled via a peptide linker to a further compound, such as a fluorescent dye or a polyplex consisting of PEI-PEG/polyIC, selectively targets PSMA-overexpressing cancer cells and delivers the polyplex of the invention to these cells.

DUPA is conjugated to the fluorescent dye Dylight680 (Thermo Scientific) via a specifically designed peptide linker consisting of a hydrocarbon chain of 8-aminooctanoic acid and a short peptide moiety escapes steric hindrance of the PSMA ligand DUPA. The peptide linker used in this example includes the peptide moiety of SEQ ID NO: 1 (Cys-Gly-Trp-Trp-Gly-Phe, cf. FIG. 1A).

Figure 1B:
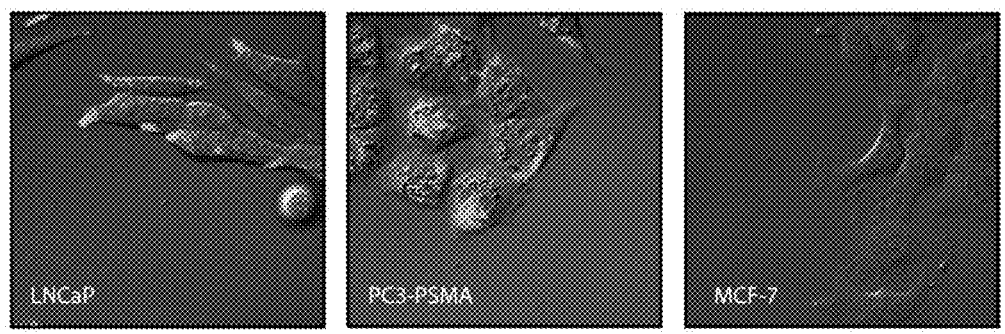

Binding of the DUPA-linker-Dylight680 conjugate to cancer cells was measured via confocal fluorescence microscopy. LNCaP cells, PSMA overexpressing cells PC3-PSMA and PSMA non-overexpressing cells MCF7 were treated with DUPA-linker-Dylight680 for 5 hours. DUPA-linker-Dylight680 successfully bound and entered LNCaP and PC3-PSMA cells, but not MCF7 cells (FIG. 1B).

Binding to PSMA occurs via a binding site which is only accessible via a deep, narrowing gap with two hydrophobic concavities. To render selective binding of DUPA conjugated to a polyplex consisting of PEI-PEG/polyIC or a conjugate consisting of PEI-PEG to PSMA possible, the distance between the PEI-PEG/polyIC polyplex or PEI-PEG conjugate and DUPA was extended by using a certain peptide linker. In this example, DUPA was conjugated to the polyIC-binding moiety PEI-PEG conjugate (PP) via a linker consisting of Cys-Gly-Trp-Trp-Gly-Phe-8-aminooctanoic acid (FIG. 1A), which provides optimal fit to the structure and binding properties of the PSMA binding site and its entry site.

PPD/polyIC Selectively Eradicates Prostate Cancer Cells Overexpressing PSMA

Selective killing of PSMA-overexpressing prostate cancer cells was demonstrated using a polyplex consisting PEI-PEG-DUPA (PPD)/polyIC. To generate PPD/polyIC, the inventors conjugated DUPA via a peptide linker to polyethyleneimine-polyethyleneglycol (PP) and coupled polyIC to the PPD conjugate, as described previously (Joubran S, et al., 2014, op. cit.).

PPD/polyIC was tested for potency and selectivity. PSMA overexpressing cells LNCaP, VCaP and PC3-PSMA and PSMA non-overexpressing cells MCF7 and PC3 were treated for 4 days with PPD/polyIC, which efficiently killed 80-95% of PSMA overexpressing cells LNCaP, VCaP and PC3-PSMA cells, while leaving MCF7 and PC3 cells intact (FIG. 2A).

Figure 2C:
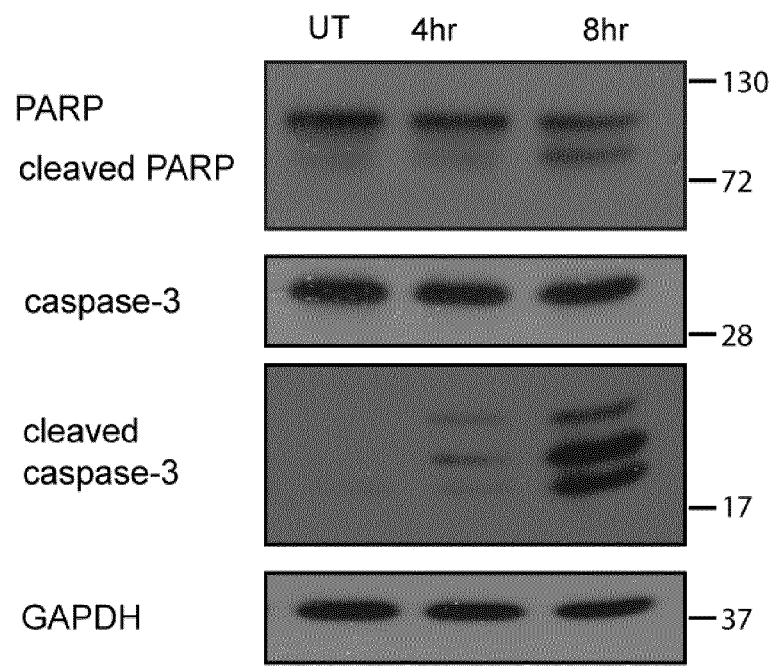

The PPD/polyIC induced death of LNCaP cells became apparent 24 h after starting the treatment with any of the applied polyIC concentrations (0.5, 1 and 2 µg/ml polyIC bound to PPD; cf. FIG. 2B). During the course of the further PPD/polyIC treatment number of killed cells increased further. After 96 h, almost 100% of the LNCaP cells were killed even by the lowest polyIC concentration applied (0.5 µg/ml; FIG. 2B). After 4 h and 8 h of PPD/polyIC treatment, cleavage of caspase 3 and PARP, respectively, became apparent. This cleavage suggests that polyIC induced cell death via apoptosis (FIG. 2C).

These results demonstrate that (i) polyIC coupled to PPD was selectively delivered to PSMA overexpressing cells; (ii) treatment with PPD/polyIC caused apoptosis and induced fast and efficient killing of PSMA overexpressing cells (FIGS. 2A, B, C). In patients with CRPC, fast and efficient cell killing induced by PPD/polyIC treatment enables extinction of tumor cell before resistance against chemotherapy can be developed. Further, high cell marker selectivity of PPD/polyIC has the benefit of minimizing toxic side effects from which cancer patients otherwise has to suffer when polyIC is administered systemically.

Treatment with PPD/polyIC Substantially Increased Cytokine Secretion

Figure 3A:
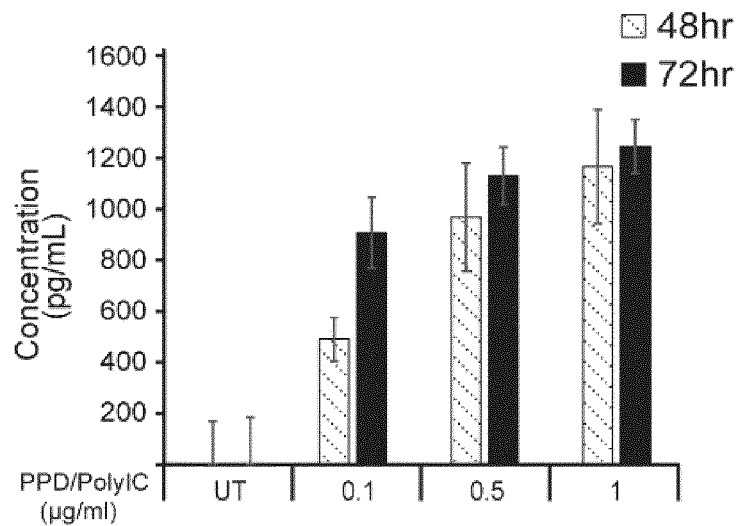
Figure 3A:
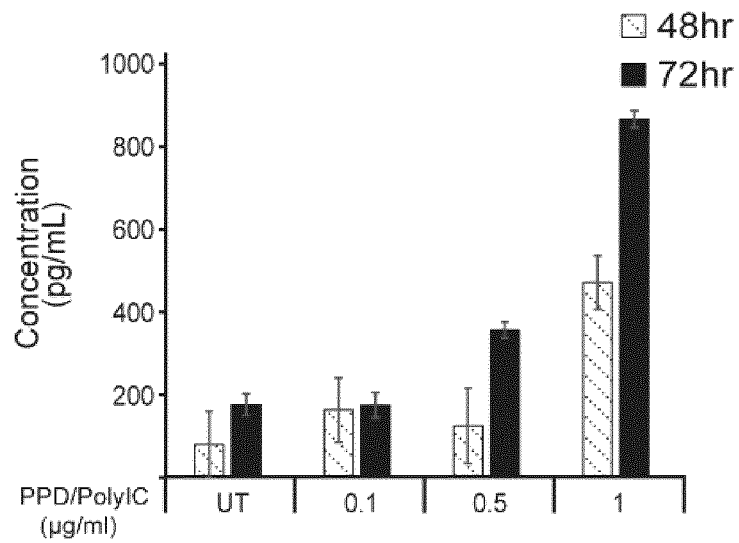
Figure 3B:
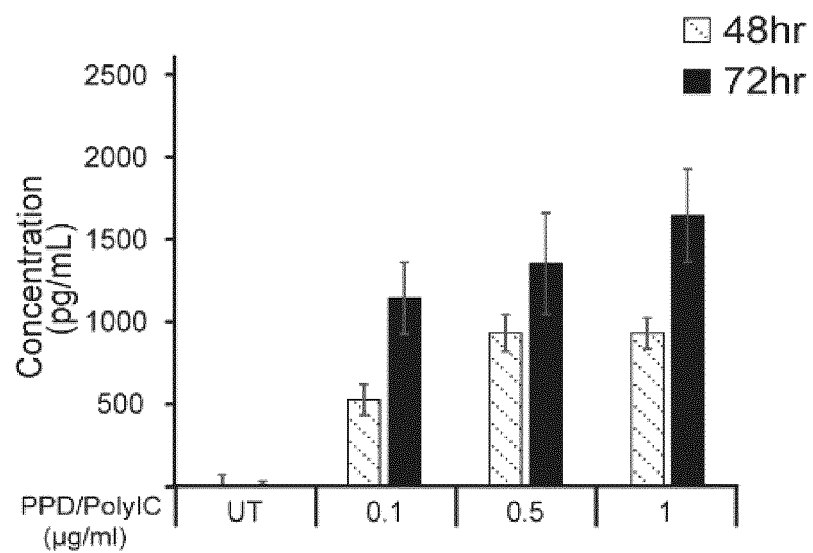
Figure 3B:
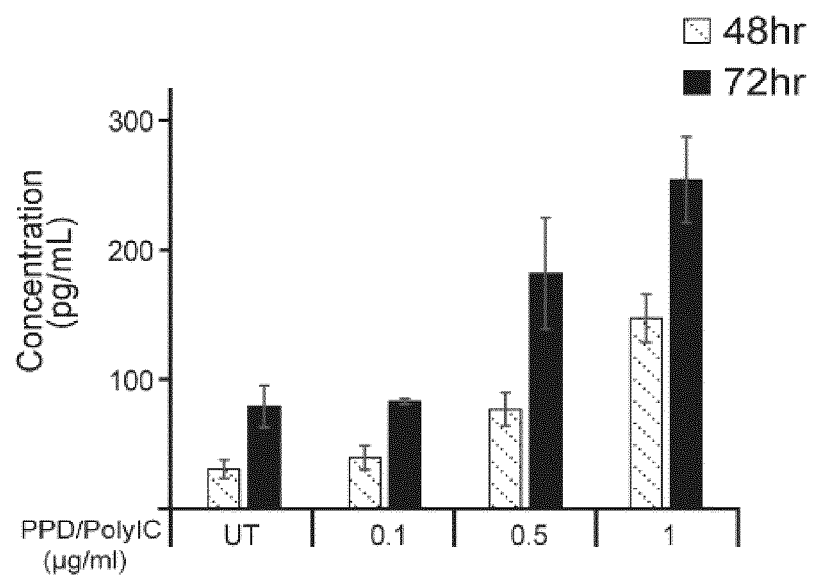
Figure 3C:
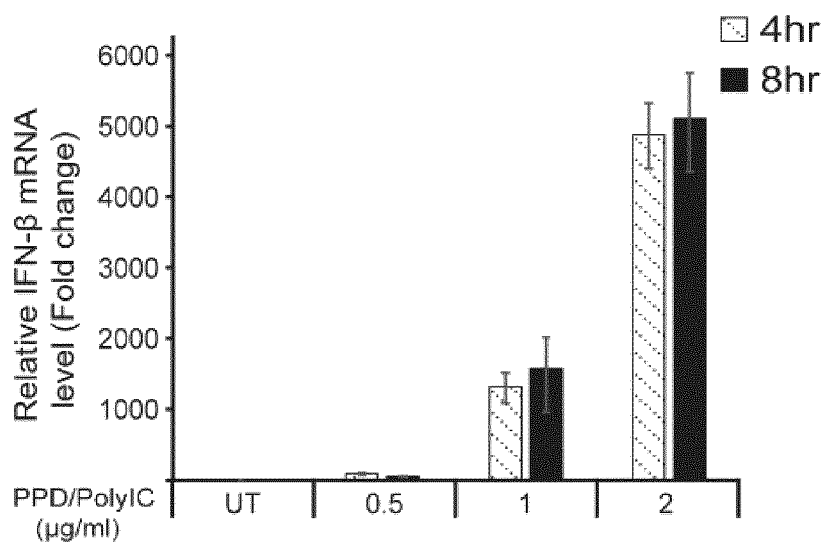
Figure 3C:
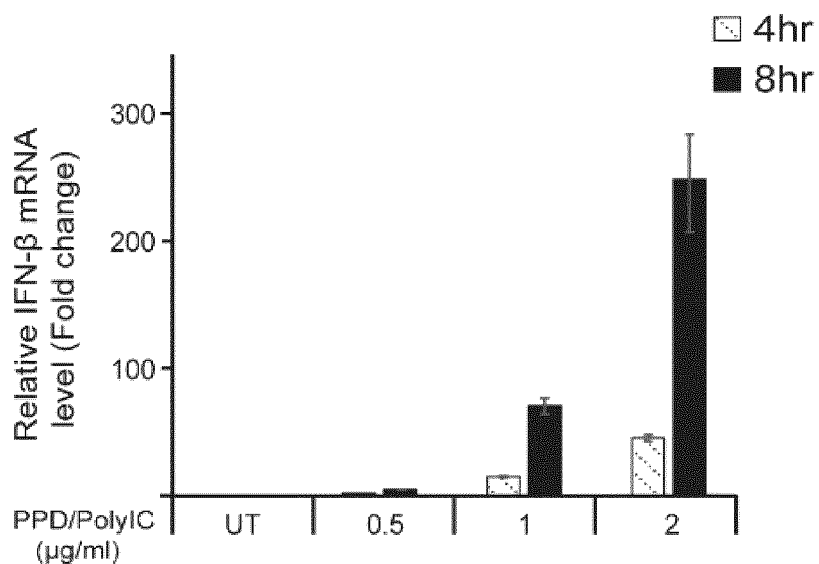

In cells dsRNA, especially polyIC triggered production and release of cytokines. These cytokines stimulated immune cells and recruited them to the infected area. The inventors demonstrated the effects of PPD/polyIC treatment on cytokine production and release in LNCaP and PC3-PSMA cells. PPD/polyIC treatment caused secretion of IP-10 and RANTES, which are both chemotactic cytokines (FIG. 3A,B ELISA). Cytotoxic cytokine IFN-β was measured already 4 h after PPD/polyIC treatment has been initiated (qRT-PCR, FIG. 3C).

Malignant tumors such as CRPC are able to develop mechanisms that impair immunological cancer defense and clearance of cancer cells. The polyplex according to the invention directly kills tumor cells (e.g. via tumor cell apoptosis), but also activates the patient's immune system to act against the cancer cells (e.g. PPD/polyIC triggered production and release of cytokines). Using the polyplex of the invention, also untargeted neighboring cancer cells were killed by bystander effects. PolyIC acts, amongst others, via agonistic binding to Toll-like receptor 3 (TLR3), activation of dsRNA dependent protein kinase (PKR), upregulation of retinoic acid-inducible gene I (RIG-1) as well as melanoma differentiation-associated gene 5 (MDAS) (Levitzki A, Targeting the Immune System to Fight Cancer Using Chemical Receptor Homing Vectors Carrying Polyinosine/Cytosine (PolyIC), Front Oncol 2012, 2:4). These signal proteins simultaneously induce different apoptotic pathways, and also cause the cancer cells to produce and release immunostimulatory cytokines.

Treatment with PPD/polyIC Induced Chemotaxis and PBMC Activation

Figure 4A:
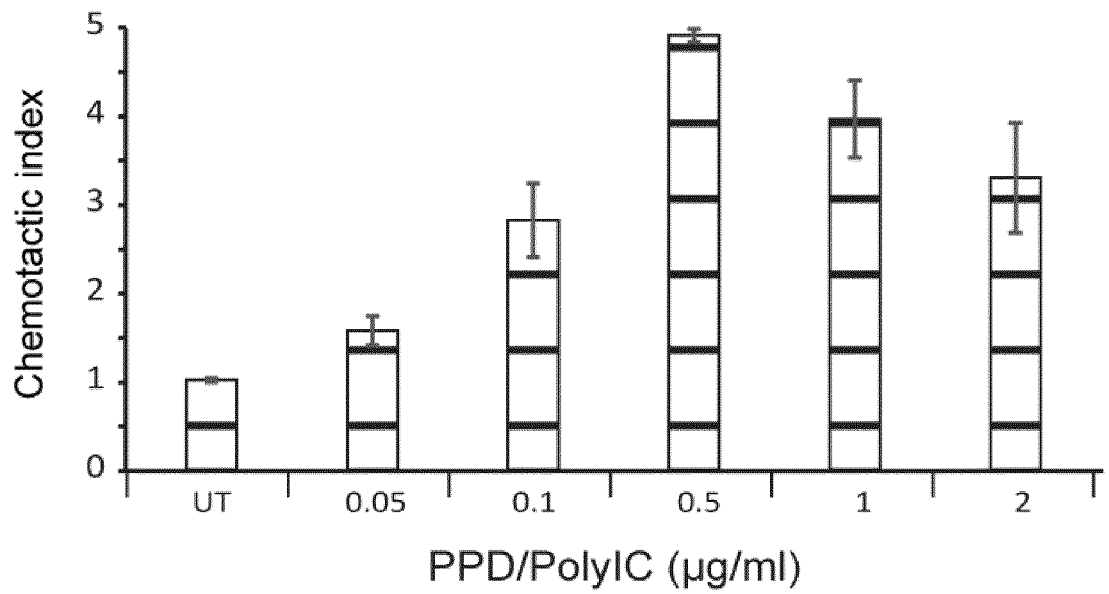
Figure 4B:
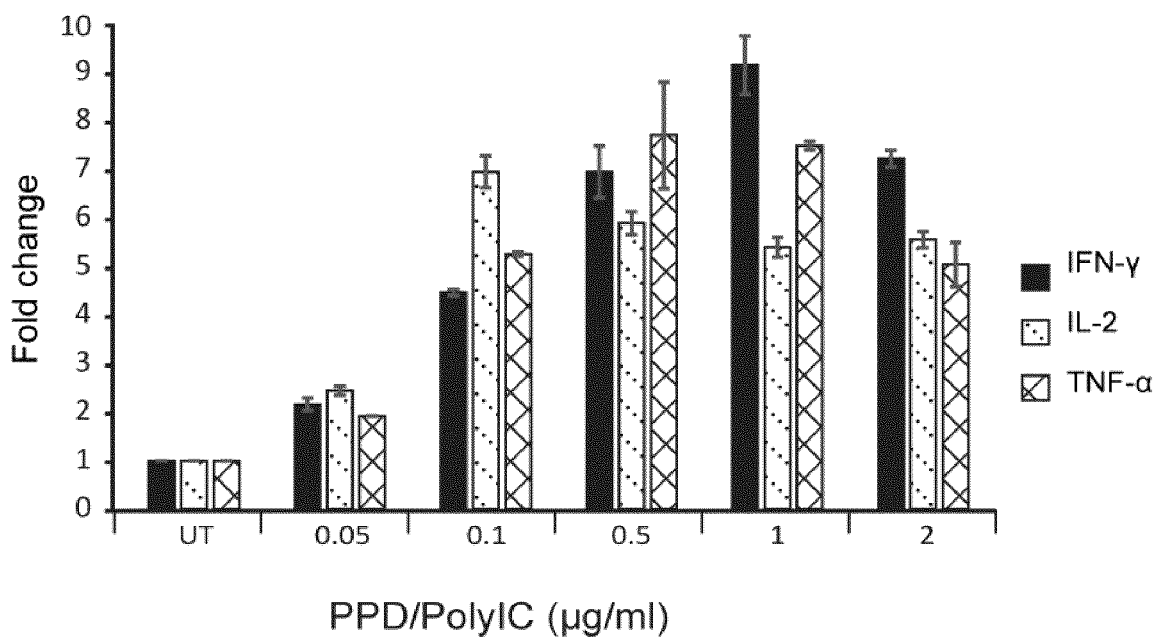

Moreover, it has been demonstrated that the PPD/polyIC polyplex of the invention leads to the recruitment of immune cells (chemotaxis) and PBMC activation. LNCaP cells were treated with PPD/polyIC for 48 hours. Compared to medium from untreated control cells, conditioned medium from these PPD/polyIC treated cells led to an increased chemotaxis of peripheral blood mononuclear cells (PBMC) (5-fold increase; FIG. 4A). The conditioned medium from PPD/polyIC treated cells leads to an increased level of IL-2 and induced the PBMCs to secrete the toxic, pro-inflammatory cytokines IFN-γ and TNFα (FIG. 4B). TNF-α is cytotoxic for certain prostate cancer cell lines PC-3, DU-145, and LNCaP (Sherwood E R et al., 1990, Therapeutic efficacy of recombinant tumor necrosis factor alpha in an experimental model of human prostatic carcinoma, J Biol Response Mod 9(1):44-52), and raised expression of IL-2 indicates that PBMCs were activated by the conditioned medium (Kruse et al., 2001, Characterization of early immunological responses in primary cultures of differentially activated human peripheral mononuclear cells, J Immunol Methods 247(1-2):131-139).

Treatment with PPD/polyIC Induced Bystander Effects

Bystander effects induced by PPD/polyIC treatment were studied in co-culture systems with LNCaP-Luc, PC3-Luc and MCF7-Luc cells, which stably express luciferase (Luc).

Figure 5A:
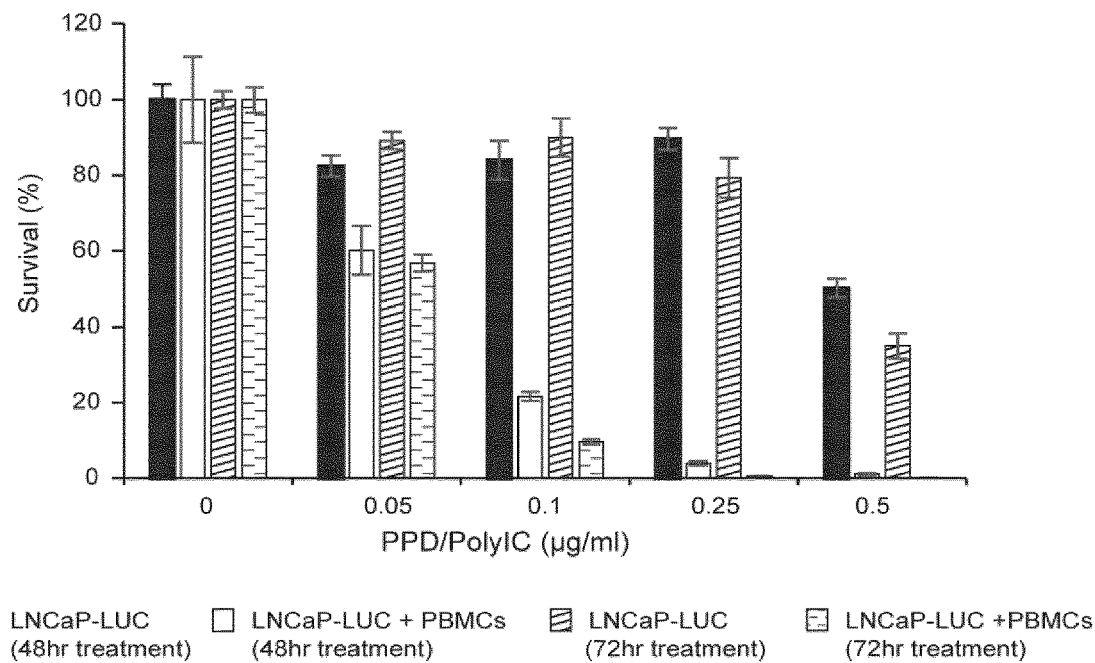

LNCaP-Luc cells were treated with low doses of PPD/polyIC, which cause cell death of up to 50% after 72 hours after initiation of treatment. When PBMCs were added to the pretreated LNCaP-Luc cells for 48 hours, even 100% of the cancer cells were cleared. Control cells that were not treated with PPD/polyIC remain unaffected by PBMCs (FIG. 5A).

Figure 5B:
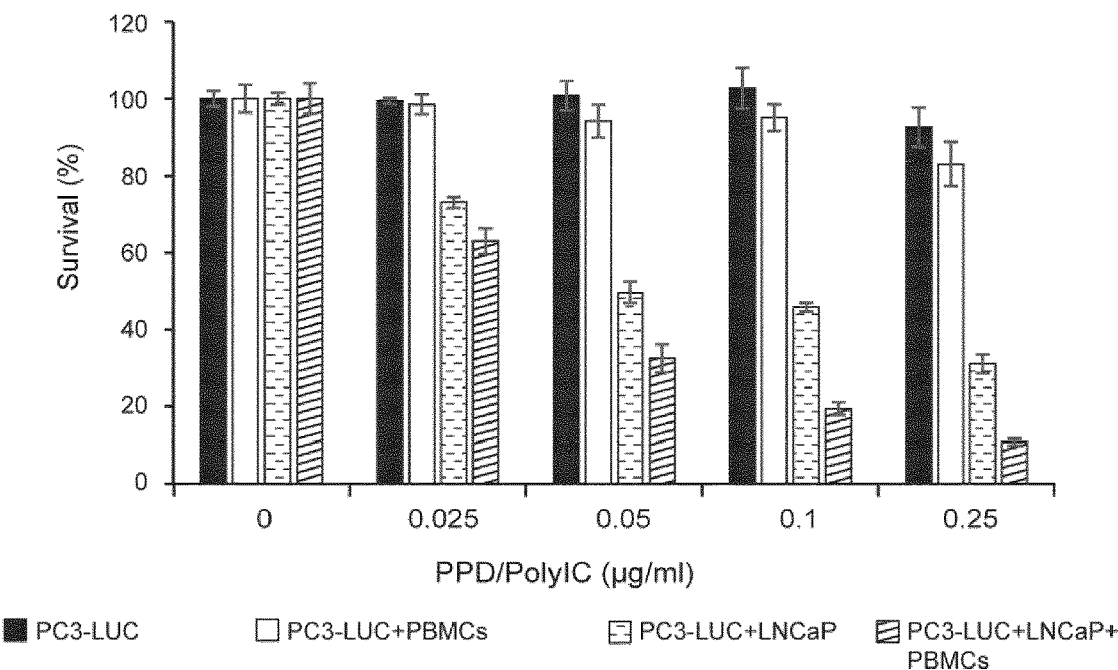
Figure 5C:
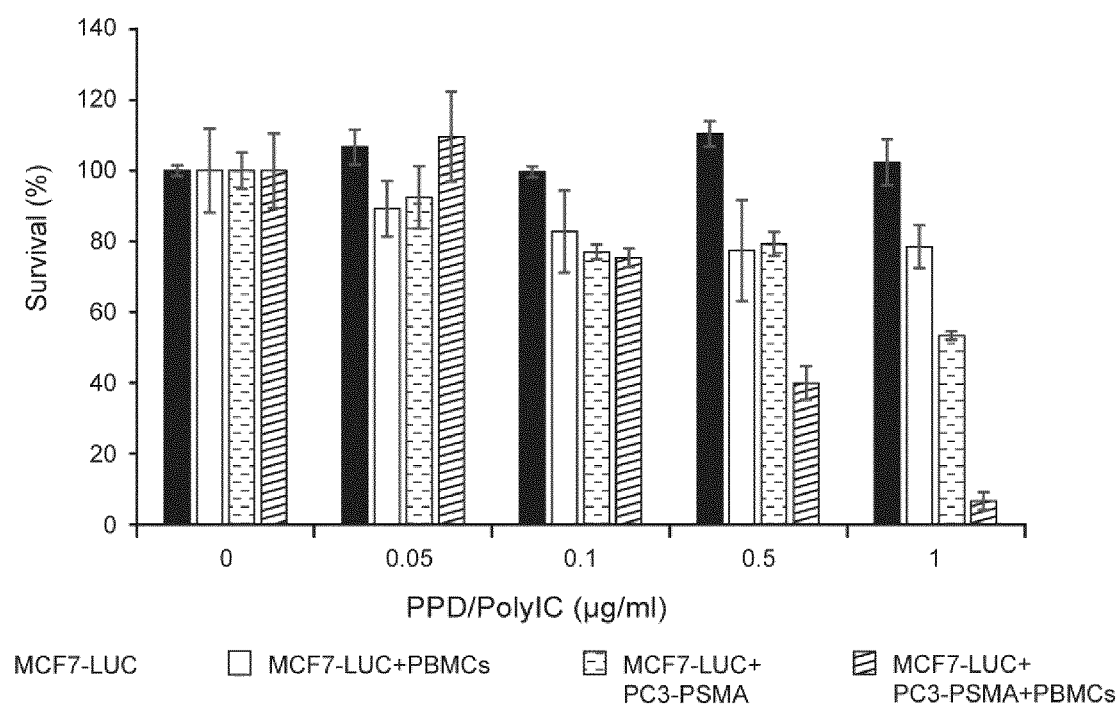

In addition, a direct bystander effect was shown by co-culturing (i) PC3-Luc cells with PPD/polyIC-treated LNCaP cells and (ii) or MCF7-Luc cells with or PPD/polyIC-treated PC3-PSMA cells. Treatment with PPD/polyIC alone had neither in PC3-Luc cells (FIG. 5B) nor in MCF7-Luc cells (FIG. 5C) any effect. Co-culturing PC3-Luc with PPD/polyIC-treated LNCaP cells led to death of up to 70% of the PC3-Luc cells (FIG. 5B), and co-culturing MCF7-Luc with PPD/polyIC-treated PC3-PSMA cells resulted in the death of up to 50% of the MCF7-Luc cells (FIG. 5C). Thus, secretion of cytotoxic cytokines from PPD/polyIC-treated PSMA-overexpressing cells induced the decline of co-cultured cells that are itself not responsive to treatment with PPD/polyIC.

The inventors also examined the combined direct and indirect bystander effects of PPD/polyIC treatment on cells that do not overexpress PSMA. Again, (i) PC3-Luc cells were co-cultured with PPD/polyIC-treated LNCaP, and (ii) MCF7-Luc cells were co-cultured with PPD/polyIC-treated PC3-PSMA cells and to both types of cell cultures PBMCs were added. The combination of PBMCs and PPD/polyIC-treated PSMA-overexpressing cells led to killing of a substantial number of cells that do not overexpress PSMA. When PBMCs were co-cultured with PPD/polyIC-treated PC3-Luc or MCF7-Luc cells, i.e. without PSMA-overexpressing cells, up to 20% of the Luc-expressing cells were killed, probably by activated PBMCs (FIG. 5B, C). The inventors believe that this effect on PC3-Luc or MCF7-Luc cells, which are not able to internalize targeted polyIC, is induced by PPD/polyIC that accumulates in the medium and induces activation of the PBMCs.

These experiments thus show that treatment with PPD/polyIC leads to the death of co-cultured cancer cells that are not themselves targeted by PPD/polyIC. A direct bystander effect was induced by toxic cytokines released from treated targeted cells and led to death of about 70% of neighboring untargeted cancer cells. This effect could be further enhanced by adding PBMCs which induce an immune-cell mediated indirect bystander effect. Compared to application of PPD/polyIC alone, addition of PBMCs resulted in increased levels of cell death using considerably smaller PPD/polyIC doses. This shows that enhancement of anti-cancer immunity can reduce the undesired side effects of systemically administered polyIC.

Example 5—Results of the In Vivo Tests

Systemic Administration of a Combination of PPD/polylC with PBMCs Induces Regression of Prostate Tumor Xenografts Moreover, the effect of PPD/polylC on CRPC was investigated in an animal model for androgen resistant prostate cancer. Male NOD-SCID mice were subcutaneously injected with PC3-PSMA cells, which overexpress human PSMA. Treatment was started when the thus caused tumors had a size of about 100 mm$^3$. To examine the effect of PPD/polyIC treatment on the immune system and combined effects of both, the immune system of the animals were reconstituted in part by administration of human PBMCs. NOD-SCID mice were repeatedly treated with PPD/polylC within a period of 3 weeks and injected twice with PBMCs during PPD/polyIC treatment (FIG. 6A). PPD/polyIC untreated control mice and mice that were treated only with PBMCs developed large tumors and has to be sacrificed 3 weeks after PPD/polyIC treatment was started. In contrast, in PPD/polyIC treated mice, tumor growth was substantially delayed. Moreover, the combination of PPD/polyIC treatment with immune reconstitution (injection of PBMCs) resulted even in a reduction of tumor size. In 4 out of 7 mice that received the PPD/polyIC+PBMCs treatment, tumors disappeared or were below the detection threshold (FIG. 6B). Therefore, the effect of the combined PPD/polyIC+PBMCs treatment was significantly better than the effect of PPD/polyIC administered alone. This suggests that the combination of the direct tumor killing effect of PPD/polyIC itself and the bystander effect elicited in the presence of immune cells results to substantial tumor regression in CRPC.

Taken together, in a xenograft animal model of androgen-resistant prostate cancer, treatment with PPD/polyIC resulted in a strong retardation of tumor growth. The combined treatment with PPD/polyIC and PBMCs reduced size of the tumors or even led to tumor eradication.

To avoid PBMCs induced toxicity, only a small number of cells was administered. The strong effect of such a small number of cells indicates that they were recruited directly to the tumor. The high speed and great potency of this treatment should prevent the development of resistance against this chemotherapy. Moreover, via the bystander effect should also heterogeneous tumors can be efficiently treated and eradicated.

In contrast to the immune-deficient mice, human CRPC patients have an active immune system. Before this background, the above-mentioned results suggest that PSMA-targeted polylC will be even more effective in human CRPC patients than in mice of the in vivo model.

Example 6—Cell Culture

All tissue culture media contained 10% fetal calf serum, penicillin (100 U/ml) and streptomycin (100 mg/1). Cell lines were cultured at 37° C., in 5% $CO_2$. Cells lines were grown in the media indicated in Tab. 2.

TABLE 2

Cell lines and culture media

| Cell line | Culture medium |
|---|---|
| LNCaP cells (Androgen insensitive prostate cancer cell model) | RPMI 1640 medium with 1 mM sodium pyruvate and 10 mM HEPES, pH 7.4 |
| PC3-PSMA cells (PSMA overexpressing cells) | RPMI 1640 medium with 5 mg/1 puromycin |
| VCaP cells (PSMA overexpressing cells) | DMEM (Dulbecco's Modified Eagle Medium) |
| PC3 and DU145 cells | MEM (Minimum Essential Medium) with 1% non-essential amino acids, 1% MEM vitamin mixture, 1 mM sodium pyruvate and 10 mM Hepes pH 7.4 |
| MCF7 cells | RPMI 1640 medium |

Lentivirus with Luc/GFP was used for infecting PC3 and LNCaP cells according to Zigler et al., 2016, whereby PC3-Luc/GFP and LNCaP-Luc/GFP was produced (Zigler et al., HER2-Targeted Polyinosine/Polycytosine Therapy Inhibits Tumor Growth and Modulates the Tumor Immune Microenvironment, Cancer Immunol Res 2016, 4(8):688-697). According to Shir A, et al., 2010, human PBMCs were isolated from blood buffy coats by Ficoll-Paque PLUS (GE Healthcare) density-gradient centrifugation and maintained (Shir A, et al., EGFR-homing dsRNA activates cancer-targeted immune response and eliminates disseminated EGFR-overexpressing tumors in mice. Clin Cancer Res 2010, 17(5):1033-1043).

The invention claimed is:

1. A method of treating castration resistant prostate cancer (CRPC) comprising administering to a patient in need thereof, an effective amount of a polyplex comprising a double stranded RNA (dsRNA) and a polymeric conjugate,
wherein said polymeric conjugate consists of a linear polyethyleneimine (LPEI), one or more polyethylene glycol (PEG) moieties, one or more linkers and one or more targeting moieties, wherein said LPEI is covalently bound to one or more PEG moieties and each of said one or more PEG moieties is conjugated via one of said one or more linkers to one of said one or more targeting moieties,
wherein each of said one or more targeting moieties is capable of binding to a cancer antigen, and wherein said cancer antigen is prostate surface membrane antigen (PSMA).

2. The method according to claim 1, wherein said dsRNA is polyinosinic-polycytidylic acid double stranded RNA (polyIC).

3. The method according to claim 1, wherein said LPEI is covalently bound to one PEG moiety (LPEI-PEG 1:1) or to three PEG moieties (LPEI-PEG 1:3).

4. The method according to claim 1, wherein said linker is a peptide moiety and wherein said peptide moiety consists of 3 to 7 amino acid residues.

5. The method according to claim 4, wherein said peptide moiety comprises the amino acid residue —(NH—$(CH_2)_7$—CO)—.

6. The method according to claim 5, wherein said peptide moiety is:

(SEQ ID NO: 1)
-(NH-$(CH_2)_7$-CO)-Phe-Gly-Trp-Trp-Gly-Cys- or (SEQ ID NO: 2)
-(NH-$(CH_2)_7$-CO)-Phe-Phe-(NH-$CH_2$-CH($NH_2$)-CO)-
Asp-Cys-.

7. The method according to claim 1, wherein said polymeric conjugate is selected from formula (a), (b), (c) or (d):

(a)  T-(NH—$(CH_2)_7$—CO)-Phe-Phe-(NH—$CH_2$—CH($NH_2$)—CO)-Asp-Cys-PEG-LPEI (SEQ ID NO:17);

(b)  T-(NH—$(CH_2)_7$—CO)-Phe-Gly-Trp-Trp-Gly-Cys-PEG-LPEI (SEQ ID NO:18);

(c)  [T-(NH—$(CH_2)_7$—CO)-Phe-Phe-(NH—$CH_2$—CH($NH_2$)—CO)-Asp-Cys-PEG]3-LPEI (SEQ ID NO:31); or (d)  [T-(NH—$(CH_2)_7$—CO)-Phe-Gly-Trp-Trp-Gly-Cys-PEG]3-LPEI (SEQ ID NO: 32);

and wherein said T represents said targeting moiety.

8. The method according to claim 1, wherein said polymeric conjugate is selected from the group consisting of formula (i), (ii), (iii) and (iv):

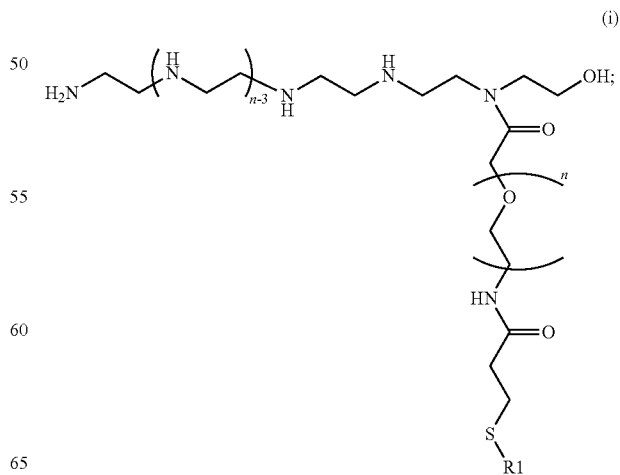

wherein R1 is
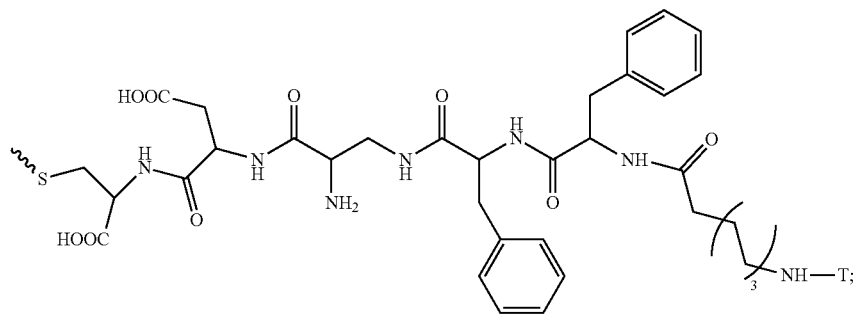
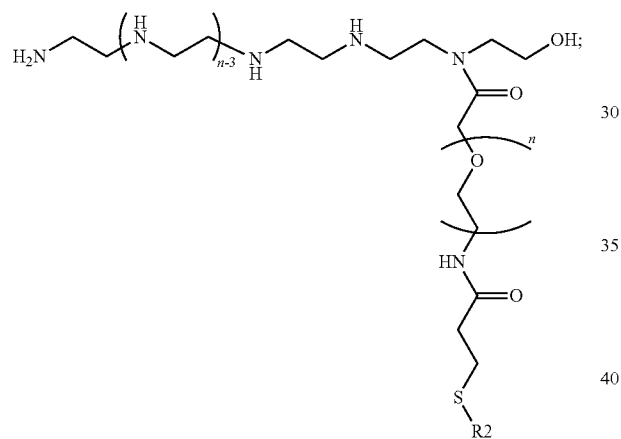
wherein R2 is
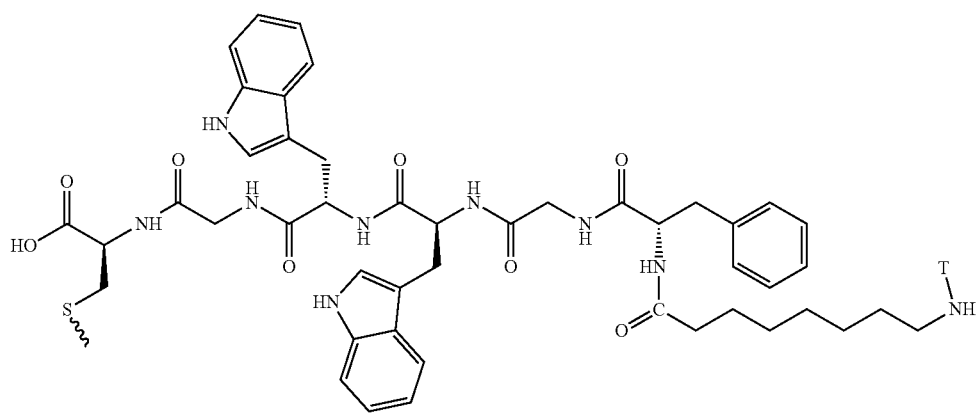

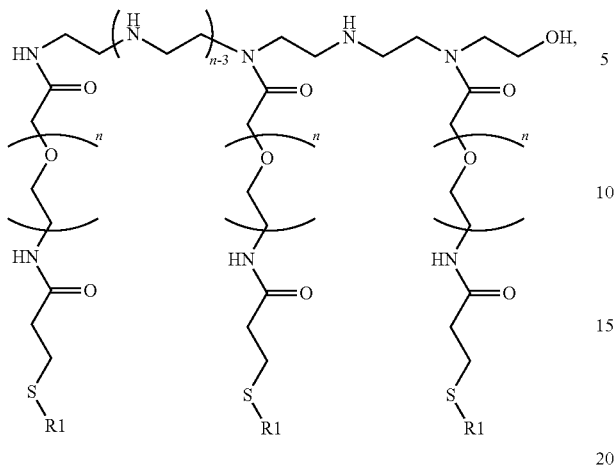
(iii)
wherein R1 is
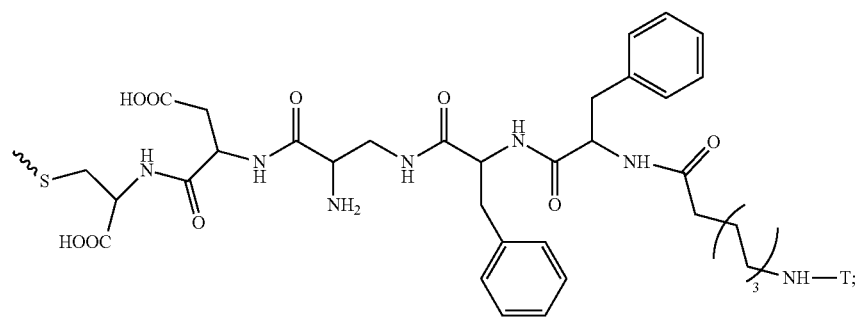
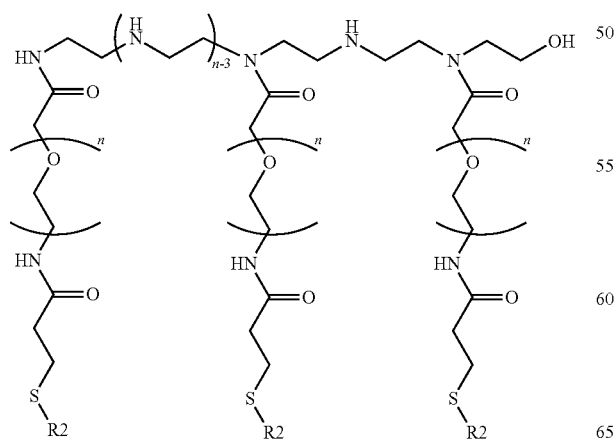
(iv)

wherein R2 is

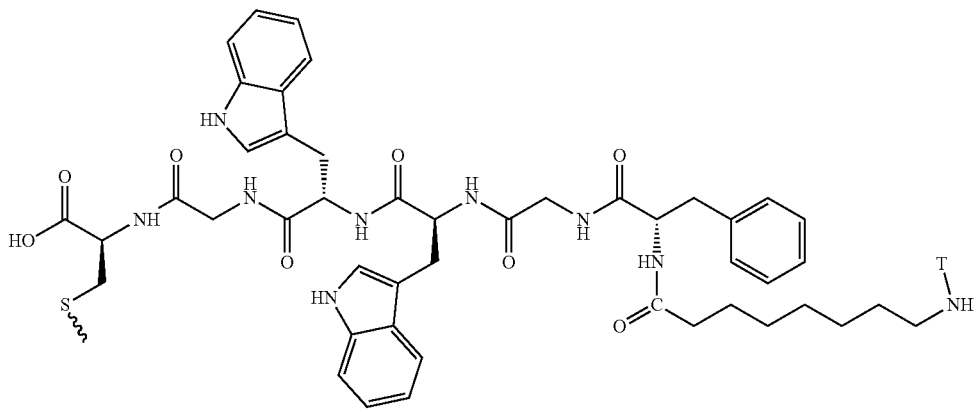

wherein said T represents said targeting moiety;
and wherein n is 40-45.

9. The method according to claim 1, wherein said targeting moiety is HOOC(CH₂)₂—CH(COOH)—NH—CO—NH—CH(COOH)—(CH₂)₂—CO— (DUPA moiety).

10. The method according to claim 1, wherein CRPC is non-metastatic CRPC or metastatic CRPC.

11. The method according to claim 1, wherein said CRPC is androgen receptor (AR) independent CRPC.

12. The method according to claim 11, wherein said androgen receptor (AR) independent CRPC is neuroendocrine prostate cancer.

13. The method according to claim 1, wherein said polyplex is used in combination with immune cells.

14. The method according to claim 13, wherein said immune cells are selected from the group consisting of tumor-infiltrating T-cells (T-TILs), tumor specific engineered T-cells and peripheral blood mononuclear cells (PBMCs).

15. A method of treating castration resistant prostate cancer (CRPC) comprising administering to a patient in need thereof, an effective amount of a pharmaceutical composition, wherein said pharmaceutical composition comprises a pharmaceutically acceptable carrier and a polyplex comprising a double stranded RNA (dsRNA) and a polymeric conjugate, wherein said polymeric conjugate consists of a linear polyethyleneimine (LPEI), one or more polyethylene glycol (PEG) moieties, one or more linkers and one or more targeting moieties,
  wherein said LPEI is covalently bound to one or more PEG moieties and each of said one or more PEG moieties is conjugated via one of said one or more linkers to one of said one or more targeting moieties,
  wherein each of said one or more targeting moieties is capable of binding to a cancer antigen, and
  wherein said cancer antigen is prostate surface membrane antigen (PSMA).

16. The method according to claim 1, wherein CRPC is metastatic CRPC.

17. The method according to claim 1, wherein said CRPC is androgen receptor (AR) dependent.

18. The method according to claim 5, wherein said peptide moiety is
  —(NH—(CH₂)₇—CO)-Phe-Gly-Trp-Trp-Gly-Cys- (SEQ ID NO: 1).

19. The method according to claim 1, wherein said polymeric conjugate is formula
  (b)  T-(NH—(CH₂)₇—CO)-Phe-Gly-Trp-Trp-Gly-Cys-PEG-LPEI (SEQ ID NO:18),
wherein said T represents said targeting moiety.

20. The method according to claim 1, wherein said polymeric conjugate is of formula (ii):

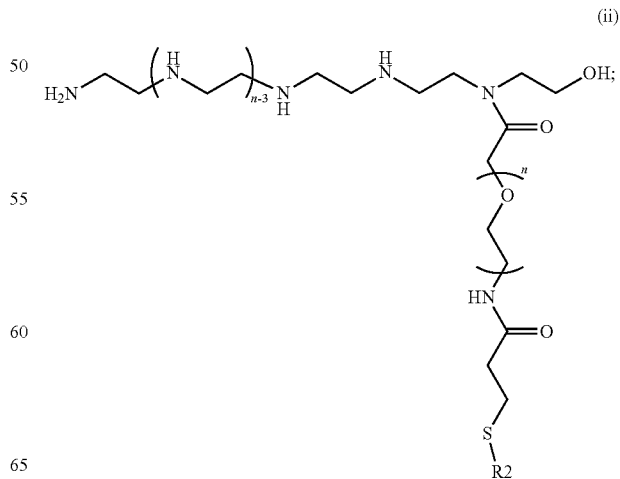

wherein R2 is
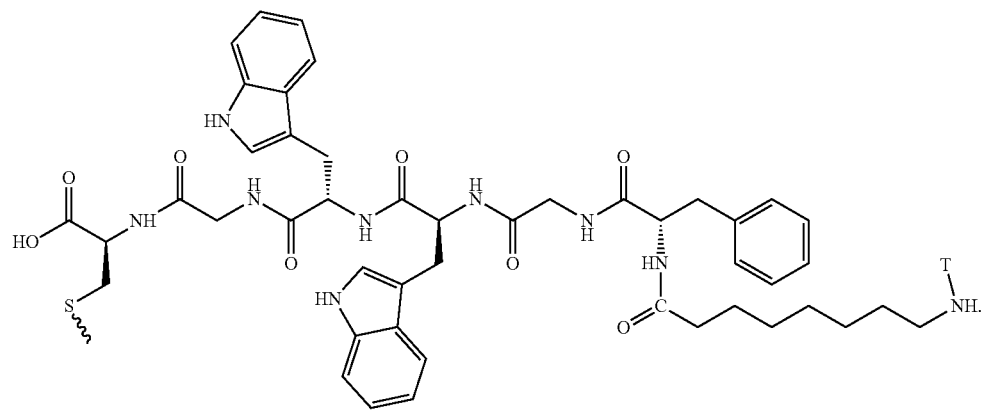
* * * * *

SEQUENCE LISTING

```
<160> NUMBER OF SEQ ID NOS: 30

<210> SEQ ID NO 1
<211> LENGTH: 7
<212> TYPE: PRT
<213> ORGANISM: Artificial Sequence
<220> FEATURE:
<223> OTHER INFORMATION: Peptide Linker 1
<220> FEATURE:
<221> NAME/KEY: MOD_RES
<222> LOCATION: (1)..(1)
<223> OTHER INFORMATION: 8-aminooctanoic acid

<400> SEQUENCE: 1

Xaa Phe Gly Trp Trp Gly Cys
1               5

<210> SEQ ID NO 2
<211> LENGTH: 6
<212> TYPE: PRT
<213> ORGANISM: Artificial Sequence
<220> FEATURE:
<223> OTHER INFORMATION: Peptide Linker 2
<220> FEATURE:
<221> NAME/KEY: MOD_RES
<222> LOCATION: (1)..(1)
<223> OTHER INFORMATION: 8-aminooctanoic acid
<220> FEATURE:
<221> NAME/KEY: MOD_RES
<222> LOCATION: (4)..(4)
<223> OTHER INFORMATION: Dpr

<400> SEQUENCE: 2

Xaa Phe Phe Xaa Asp Cys
1               5

<210> SEQ ID NO 3
<211> LENGTH: 7
<212> TYPE: PRT
<213> ORGANISM: Artificial Sequence
<220> FEATURE:
<223> OTHER INFORMATION: Peptide Linker 1-PEG-PEI (1:1), (3:1)
<220> FEATURE:
```

```
<221> NAME/KEY: MOD_RES
<222> LOCATION: (1)..(1)
<223> OTHER INFORMATION: 8-aminooctanoic acid
<220> FEATURE:
<221> NAME/KEY: BINDING
<222> LOCATION: (4)..(4)
<223> OTHER INFORMATION: PEG

<400> SEQUENCE: 3

Xaa Phe Gly Trp Trp Gly Cys
1               5

<210> SEQ ID NO 4
<211> LENGTH: 6
<212> TYPE: PRT
<213> ORGANISM: Artificial Sequence
<220> FEATURE:
<223> OTHER INFORMATION: Peptide Linker PEG
<220> FEATURE:
<221> NAME/KEY: MOD_RES
<222> LOCATION: (1)..(1)
<223> OTHER INFORMATION: 8-aminooctanoic acid
<220> FEATURE:
<221> NAME/KEY: MOD_RES
<222> LOCATION: (4)..(4)
<223> OTHER INFORMATION: Dpr
<220> FEATURE:
<221> NAME/KEY: BINDING
<222> LOCATION: (4)..(4)
<223> OTHER INFORMATION: PEG

<400> SEQUENCE: 4

Xaa Phe Phe Xaa Asp Cys
1               5

<210> SEQ ID NO 5
<211> LENGTH: 22
<212> TYPE: DNA
<213> ORGANISM: Artificial Sequence
<220> FEATURE:
<223> OTHER INFORMATION: IFN-beta forward primer

<400> SEQUENCE: 5
atgaccaaca agtgtctcct cc                                                  22

<210> SEQ ID NO 6
<211> LENGTH: 22
<212> TYPE: DNA
<213> ORGANISM: Artificial Sequence
<220> FEATURE:
<223> OTHER INFORMATION: IFN-beta reverse primer

<400> SEQUENCE: 6
gctcatggaa agagctgtag tg                                                  22

<210> SEQ ID NO 7
<211> LENGTH: 18
<212> TYPE: DNA
<213> ORGANISM: Artificial Sequence
<220> FEATURE:
<223> OTHER INFORMATION: GAPDH forward primer

<400> SEQUENCE: 7
gagccacatc gctcagac                                                       18

<210> SEQ ID NO 8
<211> LENGTH: 19
<212> TYPE: DNA
<213> ORGANISM: Artificial Sequence
```

```
<220> FEATURE:
<223> OTHER INFORMATION: GAPDH reverse primer

<400> SEQUENCE: 8
cttctcatgg ttcacaccc                                              19

<210> SEQ ID NO 9
<211> LENGTH: 22
<212> TYPE: DNA
<213> ORGANISM: Artificial Sequence
<220> FEATURE:
<223> OTHER INFORMATION: IFN-gamma forward primer

<400> SEQUENCE: 9
gctgttactg ccaggaccca ta                                          22

<210> SEQ ID NO 10
<211> LENGTH: 22
<212> TYPE: DNA
<213> ORGANISM: Artificial Sequence
<220> FEATURE:
<223> OTHER INFORMATION: INF-gamma reverse primer

<400> SEQUENCE: 10
tccgctacat ctgaatgacc tg                                          22

<210> SEQ ID NO 11
<211> LENGTH: 23
<212> TYPE: DNA
<213> ORGANISM: Artificial Sequence
<220> FEATURE:
<223> OTHER INFORMATION: IL-2 forward primer

<400> SEQUENCE: 11
agacccaggg acttaatcag caa                                         23

<210> SEQ ID NO 12
<211> LENGTH: 21
<212> TYPE: DNA
<213> ORGANISM: Artificial Sequence
<220> FEATURE:
<223> OTHER INFORMATION: IL-2 reverse primer

<400> SEQUENCE: 12
caatggttgc tgtctcatca g                                           21

<210> SEQ ID NO 13
<211> LENGTH: 22
<212> TYPE: DNA
<213> ORGANISM: Artificial Sequence
<220> FEATURE:
<223> OTHER INFORMATION: TNF-alpha forward primer

<400> SEQUENCE: 13
gtgcttgttc ctcagcctct tc                                          22

<210> SEQ ID NO 14
<211> LENGTH: 22
<212> TYPE: DNA
<213> ORGANISM: Artificial Sequence
<220> FEATURE:
<223> OTHER INFORMATION: TNF-alpha reverse primer

<400> SEQUENCE: 14
ggccagaggg ctgattagag ag                                          22
```

```
<210> SEQ ID NO 15
<211> LENGTH: 18
<212> TYPE: DNA
<213> ORGANISM: Artificial Sequence
<220> FEATURE:
<223> OTHER INFORMATION: HUPO forward primer

<400> SEQUENCE: 15
gcttcctgga gggtgtcc                                                 18

<210> SEQ ID NO 16
<211> LENGTH: 20
<212> TYPE: DNA
<213> ORGANISM: Artificial Sequence
<220> FEATURE:
<223> OTHER INFORMATION: HUPO reverse primer

<400> SEQUENCE: 16
ggactcgttt gtacccgttg                                               20

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: BINDING
<222> LOCATION: (1)..(1)
<223> OTHER INFORMATION: binding to targeting moiety
<220> FEATURE:
<221> NAME/KEY: MOD_RES
<222> LOCATION: (1)..(1)
<223> OTHER INFORMATION: 8-aminooctanoic acid
<220> FEATURE:
<221> NAME/KEY: MOD_RES
<222> LOCATION: (4)..(4)
<223> OTHER INFORMATION: Dpr
<220> FEATURE:
<221> NAME/KEY: BINDING
<222> LOCATION: (6)..(6)
<223> OTHER INFORMATION: binding to -PEG-LPEI moiety

<400> SEQUENCE: 17

Xaa Phe Phe Xaa Asp Cys
1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 8-aminooctanoic
<220> FEATURE:
<221> NAME/KEY: BINDING
<222> LOCATION: (1)..(1)
<223> OTHER INFORMATION: binding to targeting moiety
<220> FEATURE:
<221> NAME/KEY: BINDING
<222> LOCATION: (6)..(6)
<223> OTHER INFORMATION: binding to -PEG-LPEI

<400> SEQUENCE: 18

Xaa Phe Gly Trp Trp Gly Cys
1               5
```

```
<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 8-aminooctanoic acid
<220> FEATURE:
<221> NAME/KEY: BINDING
<222> LOCATION: (1)..(1)
<223> OTHER INFORMATION: binding to targeting moiety
<220> FEATURE:
<221> NAME/KEY: MOD_RES
<222> LOCATION: (4)..(4)
<223> OTHER INFORMATION: Dpr
<220> FEATURE:
<221> NAME/KEY: BINDING
<222> LOCATION: (6)..(6)
<223> OTHER INFORMATION: binding to PEG
<220> FEATURE:
<221> NAME/KEY: BINDING
<222> LOCATION: (6)..(6)
<223> OTHER INFORMATION: binding to PEG moiety

<400> SEQUENCE: 19

Xaa Phe Phe Xaa Asp Cys
1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 8-aminooctanoic
<220> FEATURE:
<221> NAME/KEY: BINDING
<222> LOCATION: (1)..(1)
<223> OTHER INFORMATION: binding to targeting moiety
<220> FEATURE:
<221> NAME/KEY: BINDING
<222> LOCATION: (6)..(6)
<223> OTHER INFORMATION: binding to PEG
<220> FEATURE:
<221> NAME/KEY: BINDING
<222> LOCATION: (6)..(6)
<223> OTHER INFORMATION: binding to PEG moiety

<400> SEQUENCE: 20

Xaa Phe Gly Trp Trp Gly Cys
1               5

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 8-aminooctanoic acid
<220> FEATURE:
<221> NAME/KEY: BINDING
```

-continued

```
<222> LOCATION: (1)..(1)
<223> OTHER INFORMATION: binding to targeting moiety
<220> FEATURE:
<221> NAME/KEY: MOD_RES
<222> LOCATION: (4)..(4)
<223> OTHER INFORMATION: Dpr
<220> FEATURE:
<221> NAME/KEY: BINDING
<222> LOCATION: (6)..(6)
<223> OTHER INFORMATION: binding to -PEG-LPEI22 moiety

<400> SEQUENCE: 21

Xaa Phe Phe Xaa Asp Cys
1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: BINDING
<222> LOCATION: (1)..(1)
<223> OTHER INFORMATION: binding to targeting moiety
<220> FEATURE:
<221> NAME/KEY: MOD_RES
<222> LOCATION: (1)..(1)
<223> OTHER INFORMATION: 8-aminooctanoic acid
<220> FEATURE:
<221> NAME/KEY: BINDING
<222> LOCATION: (6)..(6)
<223> OTHER INFORMATION: binding to -PEG-LPEI22 moiety

<400> SEQUENCE: 22

Xaa Phe Gly Trp Trp Gly Cys
1               5

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 8-aminooctanoic acid
<220> FEATURE:
<221> NAME/KEY: BINDING
<222> LOCATION: (1)..(1)
<223> OTHER INFORMATION: binding to targeting moiety
<220> FEATURE:
<221> NAME/KEY: MOD_RES
<222> LOCATION: (4)..(4)
<223> OTHER INFORMATION: Dpr
<220> FEATURE:
<221> NAME/KEY: BINDING
<222> LOCATION: (6)..(6)
<223> OTHER INFORMATION: binding to -PEG2K-LPEI moiety

<400> SEQUENCE: 23

Xaa Phe Phe Xaa Asp Cys
1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
```

-continued

```
      peptide
<220> FEATURE:
<221> NAME/KEY: MOD_RES
<222> LOCATION: (1)..(1)
<223> OTHER INFORMATION: 8-aminooctanoic acid
<220> FEATURE:
<221> NAME/KEY: BINDING
<222> LOCATION: (1)..(1)
<223> OTHER INFORMATION: binding to targeting moiety
<220> FEATURE:
<221> NAME/KEY: BINDING
<222> LOCATION: (6)..(6)
<223> OTHER INFORMATION: binding to -PEG2K-LPEI moiety

<400> SEQUENCE: 24

Xaa Phe Gly Trp Trp Gly Cys
1               5

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 8-aminooctanoic acid
<220> FEATURE:
<221> NAME/KEY: BINDING
<222> LOCATION: (1)..(1)
<223> OTHER INFORMATION: binding to targeting moiety
<220> FEATURE:
<221> NAME/KEY: MOD_RES
<222> LOCATION: (4)..(4)
<223> OTHER INFORMATION: Dpr
<220> FEATURE:
<221> NAME/KEY: BINDING
<222> LOCATION: (6)..(6)
<223> OTHER INFORMATION: binding to -PEG2K moiety

<400> SEQUENCE: 25

Xaa Phe Phe Xaa Asp Cys
1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 8-aminooctanoic acid
<220> FEATURE:
<221> NAME/KEY: BINDING
<222> LOCATION: (1)..(1)
<223> OTHER INFORMATION: binding to targeting moiety
<220> FEATURE:
<221> NAME/KEY: BINDING
<222> LOCATION: (6)..(6)
<223> OTHER INFORMATION: binding to -PEG2K moiety

<400> SEQUENCE: 26

Xaa Phe Gly Trp Trp Gly Cys
1               5

<210> SEQ ID NO 27
<211> LENGTH: 6
<212> TYPE: PRT
```

-continued

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 8-aminooctanoic acid
<220> FEATURE:
<221> NAME/KEY: BINDING
<222> LOCATION: (1)..(1)
<223> OTHER INFORMATION: binding to targeting moiety
<220> FEATURE:
<221> NAME/KEY: MOD_RES
<222> LOCATION: (4)..(4)
<223> OTHER INFORMATION: Dpr
<220> FEATURE:
<221> NAME/KEY: BINDING
<222> LOCATION: (6)..(6)
<223> OTHER INFORMATION: binding to -PEG2K-LPEI22 moiety

<400> SEQUENCE: 27

Xaa Phe Phe Xaa Asp Cys
1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 8-aminooctanoic acid
<220> FEATURE:
<221> NAME/KEY: BINDING
<222> LOCATION: (1)..(1)
<223> OTHER INFORMATION: binding to targeting moiety
<220> FEATURE:
<221> NAME/KEY: BINDING
<222> LOCATION: (6)..(6)
<223> OTHER INFORMATION: binding to -PEG2K-LPEI22 moiety

<400> SEQUENCE: 28

Xaa Phe Gly Trp Trp Gly Cys
1               5

<210> SEQ ID NO 29
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: BINDING
<222> LOCATION: (1)..(1)
<223> OTHER INFORMATION: binding to targeting moiety
<220> FEATURE:
<221> NAME/KEY: MOD_RES
<222> LOCATION: (1)..(1)
<223> OTHER INFORMATION: 8-aminooctanoic acid
<220> FEATURE:
<221> NAME/KEY: MOD_RES
<222> LOCATION: (4)..(4)
<223> OTHER INFORMATION: Dpr
```

```
<400> SEQUENCE: 29

Xaa Phe Phe Xaa Asp Cys
1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 8-aminooctanoic acid
<220> FEATURE:
<221> NAME/KEY: BINDING
<222> LOCATION: (1)..(1)
<223> OTHER INFORMATION: binding to targeting moiety

<400> SEQUENCE: 30

Xaa Phe Gly Trp Trp Gly Cys
1               5
```